US008466176B2

(12) United States Patent
Beier et al.

(10) Patent No.: US 8,466,176 B2
(45) Date of Patent: Jun. 18, 2013

(54) FUNGICIDE HYDROXIMOYL-TETRAZOLE DERIVATIVES

(75) Inventors: Christian Beier, Saint Genis-Laval (FR); Jürgen Benting, Leichlingen (DE); David Bernier, Lyons (FR); Isabelle Christian, Lyons (FR); Pierre-Yves Coqueron, Lyons (FR); Philippe Desbordes, Lyons (FR); Christophe Dubost, Lyons (FR); Pierre Genix, Lyons (FR); Benoît Hartmann, Sainte-Foy-les-Lyon (FR); Andrew Pettinger, Lyons (FR); Daniela Portz, Vettweiss (DE); Arnd Voerste, Köln (DE); Ulrike Wachendorff-Neumann, Neuwied (DE)

(73) Assignee: Bayer Cropscience AG (DE)

( * ) Notice: Subject to any disclaimer, the term of this patent is extended or adjusted under 35 U.S.C. 154(b) by 167 days.

(21) Appl. No.: 12/933,276

(22) PCT Filed: Mar. 18, 2009

(86) PCT No.: PCT/EP2009/053208
§ 371 (c)(1),
(2), (4) Date: Jan. 6, 2011

(87) PCT Pub. No.: WO2009/115557
PCT Pub. Date: Sep. 24, 2009

(65) Prior Publication Data
US 2011/0105566 A1 May 5, 2011

(30) Foreign Application Priority Data

Mar. 19, 2008 (EP) .................................... 08356047

(51) Int. Cl.
*C07D 401/02* (2006.01)
*A01N 43/78* (2006.01)

(52) U.S. Cl.
USPC ..... 514/340; 514/365; 546/268.4; 546/269.7; 548/205

(58) Field of Classification Search
None
See application file for complete search history.

(56) References Cited

U.S. PATENT DOCUMENTS

| 4,933,355 | A | 6/1990 | Yoshioka et al. |
| 5,395,845 | A | 3/1995 | Benoit et al. |
| 5,455,351 | A | 10/1995 | Kempf et al. |
| 6,472,386 | B1 | 10/2002 | Kodama |

FOREIGN PATENT DOCUMENTS

| EP | 0202157 A1 | 11/1986 |
| EP | 0556123 A1 | 8/1993 |
| EP | 1426371 A1 | 6/2004 |
| JP | 2004131392 | 4/2004 |
| JP | 2004131416 | 4/2004 |
| WO | WO 03/013247 A1 | 2/2003 |
| WO | WO 03/050087 A2 | 6/2003 |
| WO | WO 2005/016914 A1 | 2/2005 |
| WO | WO 2005/097784 | 10/2005 |
| WO | WO 2005/105778 A2 | 11/2005 |
| WO | WO 2008/006875 A1 | 1/2008 |
| WO | WO 2008/140099 A1 | 11/2008 |
| WO | WO 2009/020191 A1 | 2/2009 |

OTHER PUBLICATIONS

International Search Report dated Oct. 6, 2009, issued in corresponding International Application No. PCT/EP2009/053208.
Bailey, D.M. et al.: Effect of 2-Anilino Pyridines on Protein Synthesis, Journal of Medicinal Chemistry, vol. 14, No. 5, pp. 439-443, XP002540326, ISSN: 0022-2623, 1971.
Database CA [Online] Chemical Abstracts Service, Hill, B et al: Aromatic ring opening of used thiophenes via organolitihum addition to sulfur, XP002540327, retrieved from STN Database accession No. 1998:229500, abstract of Synlett, (4), 407-410, Coden: Synles; ISSN: 0936-5214, 1998.
Database Beilstein [Online], Beilstein Institute for Organic Chemistry, Frankfurt-Main, DE; XP002540328; Database accession No. 5404048 (BRN), abstract of Silberg, A., et al.: Chemische Berichte, vol. 102, No. 2, 1969.
Database Beilstein [Online}, Beilstein Institute for Organic Chemistry, Frankfurt-Main, DE; XP002540329; Database accession No. 960244, 5064647, 5065767, 5092198, 5109055 (BRN), abstract of Simiti, I., et al., Acta Chimica Hungarica, vol. 115, No. 3, pp. 299-304, 1984.
Database Beilstein [Online] Beilstein Institute for Ogranic Chemistry, Frankfurt-Main, DE; XP002540330, Database accession No. 4324141 (BRN), abstract of Likhate, M.A. et al., Journal of the Indian Chemical Society, vol. 67 pp. 609-610, 1990.
Database Beilstein [Online] Beilstein Institute for Organic Chemistry, Frankfurt-Main, DE; XP002540331 Database Accession No. 7251011 (BRN), abstract of Parker, J.A. et al. Journal of Heterocyclic Chemistry, vol. 32, pp. 705-076, 1995.

(Continued)

Primary Examiner — Zinna Northington Davis
(74) Attorney, Agent, or Firm — Ostrolenk Faber LLP

(57) ABSTRACT

The present invention relates to hydroximoyl-tetrazole derivatives, their process of preparation, preparation intermediate compounds, their use as fungicide active agents, particularly in the form of fungicide compositions and methods for the control of phytopathogenic fungi, notably of plants, using these compounds or compositions.

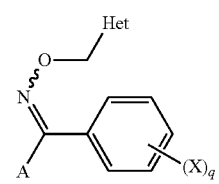

(I)

8 Claims, No Drawings

OTHER PUBLICATIONS

Database Beilstein [Online], Beilstein Institute for Organic Chemistry Frankfurt-Main, DE; XP002540332, Database accession No. 1120103, 1132426 (BRN), abstract of Silberg, F. et al., Studia Universitatis Babes-Bolyai, Chemia, vol. 13, pp. 47-51, 1968.

Database Beilstein, Beilstein Institute for Organic Chemistry, Frankfurt-Main, DE; XP002540333, Database accession No. 1001915, 178966, 996027, 989881, 791220, 960244 (BRN), abstract of Simiti, I., et al., Chemische Berichte, vol. 95, pp. 2672-2679, 1962.

U.S. Appl. No. 12/922,672, filed Sep. 14, 2010 by Christian Beier et al. entitled *Fungicide Hydroximoyl-Tetrazole Derivatives*.

U.S. Appl. No. 12/922,840, filed Sep. 15, 2010 by Christian Beier et al. entitled *Fungicide Hydroximoyl-Tetrazole Derivatives*.

US 8,466,176 B2

FUNGICIDE HYDROXIMOYL-TETRAZOLE DERIVATIVES

CROSS REFERENCE TO RELATED APPLICATION(S)

The present application is a 35 U.S.C. §371 national phase conversion of PCT/EP2009/053208 filed Mar. 18, 2009, which claims priority of European Application No. 08356047.4 filed Mar. 19, 2008.

The present invention relates to hydroximoyl-tetrazole derivatives, their process of preparation, preparation intermediate compounds, their use as fungicide active agents, particularly in the form of fungicide compositions and methods for the control of phytopathogenic fungi, notably of plants, using these compounds or compositions.

In European patent application no 1426371, there are disclosed some tetrazolyloxime derivatives to of the following chemical structure:

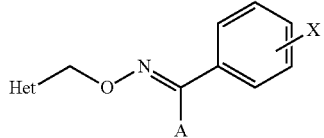

wherein A represents a tetrazolyl group, Het represents either a particular pyridinyl group or a particular thiazolyl group.

In Japanese patent application no 2004-131392, there are disclosed some tetrazolyloxime derivatives of the following chemical structure:

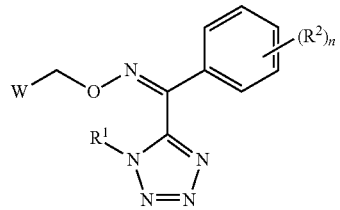

wherein W can be selected in a list of 15 various heterocycle groups.

The compounds disclosed in these two documents do not prove to provide a comparable utility than the compounds according to the invention.

It is always of high-interest in agriculture to use novel pesticide compounds in order to avoid or to control the development of resistant strains to the active ingredients. It is also of high-interest to use novel compounds being more active than those already known, with the aim of decreasing the amounts of active compound to be used, whilst at the same time maintaining effectiveness at least equivalent to the already known compounds. We have now found a new family of compounds which possess the above mentioned effects or advantages.

Accordingly, the present invention provides hydroximoyl-tetrazole derivatives of formula (I):

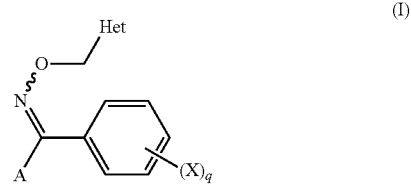

wherein
A represents a tetrazoyl group of formula ($A^1$) or ($A^2$):

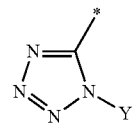

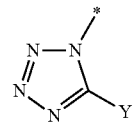

wherein Y represents an alkyl group;
X independently represents a hydrogen atom, a halogen atom, a nitro group, a hydroxy group, a cyano group, hydroxycarbonyl, $C_1$-$C_8$-alkoxycarbonyl, an amino group, a sulphenyl group, a formyl group, a substituted or non-substituted carbaldehyde O—($C_1$-$C_8$-alkyl) oxime, a formyloxy group, a formylamino group, a carbamoyl group, a N-hydroxycarbamoyl group, a pentafluoro-$\lambda^6$-sulphenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_8$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted substituted or non-substituted (di-$C_1$-$C_8$-alkyl-carbamothioyl)-oxy, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms, substituted or non-substituted tri($C_1$-$C_8$-alkyl)silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy, substituted or non-substituted [(arylcarbonyl)amino]-[$C_1$-$C_8$]-alkyl, substituted or non-substituted [{$C_1$-$C_8$-alkyl($C_1$-$C_8$-alkylcarbonyl)amino}]-[$C_1$-$C_8$]-alkyl, substituted or non-substituted [{$C_1$-$C_8$-alkyl(arylcarbonyl)amino}]-[$C_1$-$C_8$]-alkyl, substituted or non-substituted [($C_1$-$C_8$-alkylcarbonyl)amino]-[$C_1$-$C_8$]-alkyl, substituted or non-substituted heterocyclyl, substituted or non-substituted heterocyclyloxy;

q represents 1, 2, 3, 4 or 5, provided that if q represents 2, 3, 4 or 5 then X represents a hydrogen atom or a halogen atom;

Het represents (Het$^1$), (Het$^2$), (Het$^3$) or (Het$^4$):

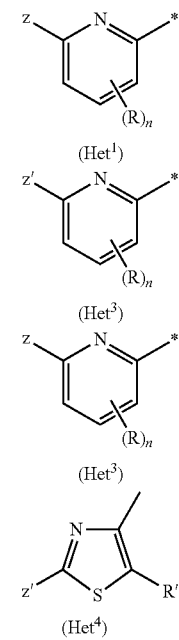

wherein
Z represents a halogen atom, a nitro group, a hydroxy group, a cyano group, a sulphenyl group, a formyl group, a substituted or non-substituted carbaldehyde O—($C_1$-$C_8$-alkyl)oxime, substituted or non-substituted ($C_1$-$C_8$-alkyl hydrazinylidene)-$C_1$-$C_8$-alkyl, hydroxycarbonyl, substituted or non-substituted $C_1$-$C_8$-alkoxycarbonyl, substituted or non-substituted ($C_1$-$C_8$-alkyl carbonyl)-$C_1$-$C_8$-alkyl, substituted or non-substituted ($C_1$-$C_8$-alkoxycarbonyl)-$C_1$-$C_8$-alkyl, a formyloxy group, a carbamoyl group, a N-hydroxycarbamoyl group, a substituted or non-substituted N-hydroxy-($C_1$-$C_8$-alkyl)-amino group, a pentafluoro-$\lambda^6$-sulphenyl group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_6$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_1$-$C_3$-halogenocycloalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylsulphenylcarbonylamino, substituted or non-substituted $C_1$-$C_8$-halogenoalkylsulphenylcarbonylamino having 1 to 5 halogen atoms, substituted or non-substituted arylsulphenylcarbonylamino, substituted or non-substituted $C_1$-$C_8$-alkylsulphenylthioylamino, substituted or non-substituted $C_1$-$C_8$-halogenoalkylsulphenylthioylamino having 1 to 5 halogen atoms, substituted or non-substituted arylsulphenylthioylamino, substituted or non-substituted N-formyl-$C_1$-$C_8$-alkylcarbonylamino, substituted or non-substituted N-formyl-$C_1$-$C_8$-alkoxycarbonylamino, substituted or non-substituted di-$C_1$-$C_8$-alkylcarbonylamino, substituted or non-substituted N—$C_1$-$C_8$-alkylcarbonyl-$C_1$-$C_8$-alkoxycarbonylamino, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted or non-substituted (di-$C_1$-$C_8$-alkyl-carbamothioyl)-oxy, substituted or non-substituted ($C_1$-$C_8$-alkyl-carbamothioyl)-amino, substituted or non-substituted substituted or non-substituted (di-$C_1$-$C_8$-alkyl-carbamothioyl)-amino, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylsulphinyl, substituted or non-substituted $C_1$-$C_8$-halogenoalkylsulphinyl having 1 to 5 halogen atoms, substituted or non-substituted $C_1$-$C_8$-alkylsulphonyl, substituted or non-substituted $C_1$-$C_8$-halogenoalkylsulphonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted phenoxy, substituted or non-substituted phenylsulphenyl, substituted or non-substituted aryl, substituted or non-substituted heterocyclyl, substituted or non-substituted aryl-[$C_1$-$C_8$]-alkyl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy, Z' represents substituted or non-substituted $C_1$-$C_8$-alkylamino, substituted or non-substituted $C_3$-$C_{10}$-cycloalkenylamino, substituted or non-substituted $C_8$-$C_{12}$-fused bicycloalkylamino, substituted or non-substituted $C_8$-$C_{12}$-fused bicycloalkenylamino, substituted or non-substituted di-$C_1$-$C_8$-alkylamino, substituted or non-substituted phenylamino, substituted or non-substituted (N—$C_1$-$C_8$-alkyl)-formylamino, substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$- alkylcarbonylamino, substituted or non-substituted (N—C$_3$-C$_{10}$-bicycloalkenyl)-C$_1$-C$_8$-alkoxycarbonylamino, substituted or non-substituted (N-phenyl)-formylamino, substituted or non-substituted (N-phenyl)-C$_1$-C$_8$-alkylcarbonylamino, substituted or non-substituted (N-phenyl)-C$_1$-C$_8$-alkoxycarbonylamino;

provided that if X represents a hydrogen atom, a halogen atom, a nitro group, a cyano group, substituted or non-substituted C$_1$-C$_8$-alkyl, substituted or non-substituted C$_1$-C$_8$-alkoxy, substituted or non-substituted C$_1$-C$_8$-alkylsulphonyl, substituted or non-substituted aryl, then if Z' represents a substituted C$_1$-C$_8$-alkylamino, substituted (N—C$_1$-C$_8$-alkyl)-formylamino, substituted (N—C$_1$-C$_8$-alkyl)-C$_1$-C$_8$-alkylcarbonylamino or substituted (N—C$_1$-C$_8$-alkyl)-C$_1$-C$_8$-alkoxycarbonylamino, then the substituent is chosen in the list consisting of a pentafluoro-$\lambda^6$-sulphenyl group, a substituted or non-substituted carbaldehyde O—(C$_1$-C$_8$-alkyl)oxime, a (hydroxyimino)-C$_1$-C$_6$-alkyl group, a tri(C$_1$-C$_8$-alkyl)silyl-C$_1$-C$_8$-alkyl, C$_3$-C$_8$-cycloalkyl, tri(C$_1$-C$_8$-alkyl)silyl, tri(C$_1$-C$_8$-alkyl)silyl-C$_3$-C$_8$-cycloalkyl, a C$_1$-C$_8$-halogenocycloalkyl having 1 to 5 halogen atoms, C$_3$-C$_8$-cycloalkoxy, a C$_2$-C$_8$-halogenoalkenyloxy having 1 to 5 halogen atoms, a C$_3$-C$_8$-halogenoalkynyloxy having 1 to 5 halogen atoms, a (C$_1$-C$_6$-alkoxyimno)-C$_1$-C$_6$-alkyl, a (C$_1$-C$_6$-alkenyloxyimino)-C$_1$-C$_6$-alkyl, a (C$_1$-C$_6$-alkynyloxyimino)-C$_1$-C$_6$-alkyl, and (benzyloxyimino)-C$_1$-C$_6$-alkyl;

R independently represents a hydrogen atom, a halogen atom, a cyano group, an amino group, a substituted or non-substituted carbaldehyde O—(C$_1$-C$_8$-alkyl)oxime, a formyloxy group, a formylamino group, a carbamoyl group, a N-hydroxycarbamoyl group, a pentafluoro-$\lambda^6$-sulphenyl group, a formylamino group, substituted or non-substituted C$_1$-C$_8$-alkoxyamino group, substituted or non-substituted N—C$_1$-C$_8$-alkyl-(C$_1$-C$_8$-alkoxyamino group, substituted or non-substituted (C$_1$-C$_8$-alkylamino)-amino group, substituted or non-substituted N—C$_1$-C$_8$-alkyl-(C$_1$-C$_8$-alkylamino)-amino group, a substituted or non-substituted (hydroxyimino)-C$_1$-C$_6$-alkyl group, substituted or non-substituted C$_1$-C$_8$-alkyl, substituted or non-substituted C$_3$-C$_8$-cycloalkyl, substituted or non-substituted C$_1$-C$_8$-halogenoalkyl having 1 to 5 halogen atoms, substituted or non-substituted C$_1$-C$_8$-halogenocycloalkyl having 1 to 5 halogen atoms, a substituted or non-substituted C$_2$-C$_8$-alkenyl, substituted or non-substituted C$_2$-C$_8$-alkynyl, substituted or non-substituted C$_1$-C$_8$-alkylamino, substituted or non-substituted di-C$_1$-C$_8$-alkylamino, substituted or non-substituted C$_1$-C$_8$-alkoxy, substituted or non-substituted C$_1$-C$_8$-halogenoalkoxy having 1 to 5 halogen atoms, substituted or non-substituted C$_1$-C$_8$-alkylsulphenyl, substituted or non-substituted C$_1$-C$_8$-halogenoalkylsulphenyl having 1 to 5 halogen atoms, substituted or non-substituted C$_2$-C$_8$-alkenyloxy, substituted or non-substituted C$_2$-C$_8$-halogenoalkenyloxy having 1 to 5 halogen atoms, substituted or non-substituted C$_3$-C$_8$-alkynyloxy, substituted or non-substituted C$_3$-C$_8$-halogenoalkynyloxy having 1 to 5 halogen atoms, substituted or non-substituted C$_1$-C$_8$-alkylcarbamoyl, substituted or non-substituted di-C$_1$-C$_8$-alkylcarbamoyl, substituted or non-substituted N—C$_1$-C$_8$-alkyloxycarbamoyl, substituted or non-substituted C$_1$-C$_8$-alkoxycarbamoyl, substituted or non-substituted N—C$_1$-C$_8$-alkyl-C$_1$-C$_8$-alkoxycarbamoyl, substituted or non-substituted C$_1$-C$_8$-alkoxycarbonyl, substituted or non-substituted C$_1$-C$_8$-halogenoalkoxycarbonyl having 1 to 5 halogen atoms, substituted or non-substituted C$_1$-C$_8$-alkylcarbonyloxy, substituted or non-substituted C$_1$-C$_8$-halogenoalkylcarbonyloxy having 1 to 5 halogen atoms, substituted or non-substituted C$_1$-C$_8$-alkylcarbonylamino, substituted or non-substituted C$_1$-C$_8$-halogenoalkylcarbonylamino having 1 to 5 halogen atoms, substituted or non-substituted C$_1$-C$_8$-alkoxycarbonylamino, substituted or non-substituted C$_1$-C$_8$-halogenoalkoxycarbonylamino having 1 to 5 halogen atoms, substituted or non-substituted C$_1$-C$_8$-alkylcarbamoylamino, substituted or non-substituted C$_1$-C$_8$-halogenoalkylcarbamoylamino having 1 to 5 halogen atoms, substituted or non-substituted di-C$_1$-C$_8$-alkylcarbamoylamino, substituted or non-substituted di-C$_1$-C$_8$-halogenoalkylcarbamoylamino having 1 to 5 halogen atoms, substituted or non-substituted N—C$_1$-C$_8$-alkyl-(C$_1$-C$_8$-alkylcarbamoyl)amino, substituted or non-substituted N—C$_1$-C$_8$-alkyl-(C$_1$-C$_8$-halogenoalkylcarbamoyl)amino having 1 to 5 halogen atoms, substituted or non-substituted N—C$_1$-C$_8$-alkyl-(di-C$_1$-C$_8$-alkylcarbamoyl)amino, substituted or non-substituted N—C$_1$-C$_8$-alkyl-(di-C$_1$-C$_8$-halogenoalkylcarbamoyl)amino having 1 to 5 halogen atoms, substituted or non-substituted C$_1$-C$_8$-alkylaminocarbonyloxy, substituted or non-substituted di-C$_1$-C$_8$-alkylaminocarbonyloxy, substituted or non-substituted C$_1$-C$_8$-alkylcarbamothioyl, substituted or non-substituted di-C$_1$-C$_8$-alkylcarbamothioyl, substituted or non-substituted N—C$_1$-C$_8$-alkyloxycarbamothioyl, substituted or non-substituted C$_1$-C$_8$-alkoxycarbamothioyl, substituted or non-substituted N—C$_1$-C$_8$-alkyl-C$_1$-C$_8$-alkoxycarbamothioyl, substituted or non-substituted C$_1$-C$_8$alkylthioylamino, substituted or non-substituted C$_1$-C$_8$-halogenoalkylthioylamino having 1 to 5 halogen atoms, substituted or non-substituted C$_1$-C$_8$-alkylsulphenyl, substituted or non-substituted C$_1$-C$_8$-alkylaminosulfamoyl, substituted or non-substituted di-C$_1$-C$_8$-alkylaminosulfamoyl, substituted or non-substituted (C$_1$-C$_6$-alkoxyimino)-C$_1$-C$_6$-alkyl, substituted or non-substituted (C$_1$-C$_6$-alkenyloxyimino)-C$_1$-C$_6$-alkyl, substituted or non-substituted (C$_1$-C$_6$-alkynyloxyimino)-C$_1$-C$_6$-alkyl, substituted or non-substituted (benzyloxyimino)-C$_1$-C$_6$-alkyl, substituted or non-substituted benzyloxy, substituted or non-substituted benzylsulphenyl, substituted or non-substituted benzylamino, substituted or non-substituted phenoxy, substituted or non-substituted phenylsulphenyl, substituted or non-substituted phenylamino, substituted or non-substituted aryl, substituted or non-substituted heterocyclyl, substituted or non-substituted aryl-[C$_1$-C$_8$]-alkyl, substituted or non-substituted tri(C$_1$-C$_8$-alkyl)-silyloxy, substituted or non-substituted C$_1$-C$_8$-alkylsulfenylamino, substituted or non-substituted C$_1$-C$_8$-halogenoalkylsulphinylamino having 1 to 5 halogen atoms, substituted or non-substituted C$_1$-C$_8$-alkylsulphonyl amino, substituted or non-substituted C$_1$-C$_8$-halogenoalkylsulphonylamino having 1 to 5 halogen atoms, substituted or non-substituted C$_1$-C$_8$-alkoxysulphonylamino, substituted or non-substituted C$_1$-C$_8$-halogenoxysulphonylamino having 1 to 5 halogen atoms, substituted or non-substituted tri(C$_1$-C$_8$-alkyl)-silyl, substituted or non-substituted (C$_1$-C$_6$-alkylideneamino)oxy, substituted or non-substituted (C$_1$-C$_6$-alkenylideneamino)oxy, substituted or non-substituted (C$_1$-C$_6$-alkynylideneamino)oxy, substituted or non-substituted (benzylideneamino)oxy;

n represents 0, 1, 2 or 3;

R' represents a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted aryl, substituted or non-substituted heterocyclyl;

as well as salts, N-oxides, metallic complexes and metalloidic complexes thereof.

Any of the compounds according to the invention can exist as one or more stereoisomers depending on the number of stereogenic units (as defined by the IUPAC rules) in the compound. The invention thus relates equally to all the stereoisomers and to the mixtures of all the possible stereoisomers, in all proportions. The stereoisomers can be separated according to the methods which are known per se by the man ordinary skilled in the art. Notably, the stereostructure of the oxime moiety present in the tetrazolyloxime derivative of formula (I) includes (E) or (Z) isomers and these stereoisomers form part of the present invention.

According to the invention, the following generic terms are generally used with the following meanings:

halogen means fluorine, chlorine, bromine or iodine;
heteroatom can be nitrogen, oxygen or sulphur;
unless indicated otherwise, a group or a substituent that is substituted according to the invention can be substituted by one or more of the following groups or atoms: a halogen atom, a nitro group, a hydroxy group, a cyano group, an amino group, a sulphenyl group, a pentafluoro-$\lambda^6$-sulphenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a formylamino group, a (hydroxyimino)-$C_1$-$C_6$-alkyl group, a $C_1$-$C_8$-alkyl, a tri($C_1$-$C_8$-alkyl)silyl, a tri($C_1$-$C_8$-alkyl)silyl-$C_1$-$C_8$-alkyl, $C_3$-$C_8$-cycloalkyl, tri($C_1$-$C_8$-alkyl)silyl-$C_3$-$C_8$-cycloalkyl, a $C_1$-$C_8$-halogenoalkyl having 1 to 5 halogen atoms, a $C_3$-$C_8$-halogenocycloalkyl having 1 to 5 halogen atoms, a $C_2$-$C_8$-alkenyl, a $C_3$-$C_8$-cycloalkenyl a $C_2$-$C_8$-alkynyl, a $C_2$-$C_8$-alkenyloxy, a $C_2$-$C_8$-alkynyloxy, a $C_1$-$C_8$-alkylamino, a di-$C_1$-$C_8$-alkylamino, a $C_1$-$C_8$-alkoxy, a $C_1$-$C_8$-halogenoalkoxy having 1 to 5 halogen atoms, a $C_1$-$C_8$-alkylsulphenyl, a $C_1$-$C_8$-halogenoalkylsulphenyl having 1 to 5 halogen atoms, a $C_2$-$C_8$-alkenyloxy, a $C_2$-$C_8$-halogenoalkenyloxy having 1 to 5 halogen atoms, a $C_3$-$C_8$-alkynyloxy, a $C_3$-$C_8$-halogenoalkynyloxy having 1 to 5 halogen atoms, a $C_1$-$C_8$-alkylcarbonyl, a $C_1$-$C_8$-halogenoalkylcarbonyl having 1 to 5 halogen atoms, a $C_1$-$C_8$-alkylcarbamoyl, a di-$C_1$-$C_8$alkylcarbamoyl, a N—$C_1$-$C_8$-alkyloxycarbamoyl, a $C_1$-$C_8$-alkoxycarbamoyl, a N—$C_1$-$C_8$-alkyl-$C_1$-$C_8$-alkoxycarbamoyl, a $C_1$-$C_8$-alkoxycarbonyl, a $C_1$-$C_8$-halogenoalkoxycarbonyl having 1 to 5 halogen atoms, a $C_1$-$C_8$-alkylcarbonyloxy, a $C_1$-$C_8$-halogenoalkylcarbonyloxy having 1 to 5 halogen atoms, a $C_1$-$C_8$-alkylcarbonylamino, a $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, a $C_1$-$C_8$-alkylaminocarbonyloxy, a di-$C_1$-$C_8$-alkylaminocarbonyloxy, a $C_1$-$C_8$-alkyloxycarbonyloxy, a $C_1$-$C_8$-alkylsulphenyl, a $C_1$-$C_8$-halogenoalkylsulphenyl having 1 to 5 halogen atoms, a $C_1$-$C_8$-alkylsulphinyl, a $C_1$-$C_8$-halogenoalkylsulphinyl having 1 to 5 halogen atoms, a $C_1$-$C_8$-alkylsulphonyl, a $C_1$-$C_8$-halogenoalkylsulphonyl having 1 to 5 halogen atoms, a $C_1$-$C_8$-alkylaminosulfamoyl, a di-$C_1$-$C_8$-alkylaminosulfamoyl, a ($C_1$-$C_6$-alkoxyimino)-$C_1$-$C_6$-alkyl, a ($C_1$-$C_6$-alkenyloxyimino)-$C_1$-$C_6$-alkyl, a ($C_1$-$C_6$-alkynyloxyimino)-$C_1$-$C_6$-alkyl, (benzyloxyimino)-$C_1$-$C_6$-alkyl, $C_1$-$C_8$-alkoxyalkyl, $C_1$-$C_8$-halogenoalkoxyalkyl having 1 to 5 halogen atoms, aryl, heterocyclyl, benzyloxy, benzylsulphenyl, benzylamino, phenoxy, phenylsulphenyl or phenylamino;

the term "aryl" means phenyl or naphthyl;

The term "heterocyclyl" means saturated or unsaturated 4-, 5-, 6- or 7-membered ring comprising up to 4 heteroatoms selected in the list consisting of N, O, S.

In the tetrazoyl group of formula ($A^1$) or ($A^2$), Y represents an alkyl group. Among these alkyl groups, an alkyl group having 1 to 3 carbon atoms such as a methyl group, an ethyl group, a n-propyl group or an isopropyl group is preferred. Among these alkyl groups, a methyl group or an ethyl group is particularly preferred.

Preferred compounds of formula (I) according to the invention are those wherein X represents a hydrogen atom; a chlorine atom; a fluorine atom; an alkyl group having 1 to 4 carbon atoms, for example a methyl group, an ethyl group, a n-propyl group, an isopropyl group, a n-butyl group, an isobutyl group, a sec-butyl group and a tert-butyl group, in particular a methyl group or a tert-butyl group; an alkoxy group having 1 to 3 carbon atoms, for example a methoxy group, an ethoxy group, a propoxy group and an isopropoxy group, in particular, a methoxy group or an ethoxy group; or a phenyl group, a 4-methylphenyl group and a 4-chlorophenyl group, in particular a phenyl; or a substituted or non-substituted $C_1$-$C_8$-alkylsulphenyl, for example a methylsulphenyl group.

Other preferred compounds of formula (I) according to the invention are those wherein q represents 1 or 2. More preferably, q represents 1.

Other preferred compounds of formula (I) according to the invention are those wherein Z represents a halogen atom, a cyano group, a substituted or non-substituted carbaldehyde O—($C_1$-$C_8$-alkyl)oxime, substituted or non-substituted $C_1$-$C_8$-alkoxyamino group, substituted or non-substituted N—$C_1$-$C_8$-alkyl-($C_1$-$C_8$-alkoxy)-amino group, a substituted or non-substituted $C_2$-$C_8$-alkenyl, substituted or non-substituted $C_2$-$C_8$-alkynyl, substituted or non-substituted $C_1$-$C_8$-alkylsulphenylcarbonylamino, substituted or non-substituted $C_1$-$C_8$-halogenoalkylsulphenylcarbonylamino having 1 to 5 halogen atoms, substituted or non-substituted arylsulphenylcarbonylamino, substituted or non-substituted $C_1$-$C_8$-alkylthioylamino, substituted or non-substituted $C_1$-$C_8$-halogenoalkylthioylamino having 1 to 5 halogen atoms, substituted or non-substituted $C_1$-$C_8$-alkylsulfenylamino, substituted or non-substituted $C_1$-$C_8$-halogenoalkylsulphinylamino having 1 to 5 halogen atoms, substituted or non-substituted $C_1$-$C_8$-alkylsulphonylamino, substituted or non-substituted $C_1$-$C_8$-halogenoalkylsulphonylamino having 1 to 5 halogen atoms, substituted or non-substituted $C_1$-$C_8$-alkoxysulphonylamino, substituted or non-substituted $C_1$-$C_8$-halogenoxysulphonylamino having 1 to 5 halogen atoms.

Other more preferred compounds of formula (I) according to the invention are those wherein Z represents substituted or non-substituted $C_1$-$C_8$-alkoxyamino group, a substituted or non-substituted $C_2$-$C_8$-alkenyl, substituted or non-substituted $C_2$-$C_8$-alkynyl, substituted or non-substituted $C_1$-$C_8$-alkylthioylamino.

Other preferred compounds of formula (I) according to the invention are those wherein Z' substituted or non-substituted $C_1$-$C_8$-alkylamino, substituted or non-substituted $C_3$-$C_{10}$-cycloalkenylamino, substituted or non-substituted (N—$C_1$-$C_8$-alkyl)-formylamino, substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino. Other more preferred compounds of formula (I) according to the invention are those wherein Z' represents a substituted or non-substituted $C_1$-$C_8$-alkylamino, substituted or non-substituted (N—$C_1$-$C_8$-alkyl)-formylamino, substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino.

Other even more preferred compounds of formula (I) according to the invention are those wherein Z' represents a non-substituted $C_1$-$C_8$-alkylamino, a substituted $C_1$-$C_8$-alkylamino and the substituent is chosen in the list consisting of a tri($C_1$-$C_8$-alkyl)silyl-$C_1$-$C_8$-alkyl, $C_3$-$C_8$-cycloalkyl, tri($C_1$-$C_8$-alkyl)silyl, tri($C_1$-$C_8$-alkyl)silyl-$C_3$-$C_8$-cycloalkyl, a $C_1$-$C_8$-halogenocycloalkyl having 1 to 5 halogen atoms, $C_3$-$C_8$-cycloalkoxy, a $C_2$-$C_8$-halogenoalkenyloxy having 1 to 5 halogen atoms.

Other preferred compounds of formula (I) according to the invention are those wherein R independently represents a hydrogen atom, a halogen atom, a cyano group, a substituted or non-substituted carbaldehyde O—($C_1$-$C_8$-alkyl)oxime, a formylamino group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_2$-$C_8$-alkynyl, substituted or non-substituted $C_1$-$C_8$-alkoxy, substituted or non-substituted $C_3$-$C_8$-alkynyloxy.

Other preferred compounds of formula (I) according to the invention are those wherein n represents 0 or 1.

Other preferred compounds of formula (I) according to the invention are those wherein R' represents a hydrogen atom, a halogen atom, a cyano group, substituted or non-substituted $C_1$-$C_8$-alkyl, substituted or non-substituted $C_1$-$C_8$-halogenoalkyl having 1 to 5 halogen atoms.

The above mentioned preferences with regard to the substituents of the compounds of formula (I) according to the invention can be combined in various manners. These combinations of preferred features thus provide sub-classes of compounds according to the invention. Examples of such sub-classes of preferred compounds according to the invention can combine:

preferred features of A with preferred features of one or more of Het, X and q;
preferred features of Het with preferred features of one or more of A, X and q;
preferred features of X with preferred features of one or more of A, Het and q;
preferred features of q with preferred features of one or more of A, Het and X.

In these combinations of preferred features of the substituents of the compounds according to the invention, the said preferred features can also be selected among the more preferred features of each of A, Het, X and q; so as to form most preferred subclasses of compounds according to the invention.

The preferred features of the other substituents of the compounds according to the invention can also be part of such sub-classes of preferred compounds according to the invention, notably the groups of substituents Y, Z, Z' R, n and R'.

The present invention also relates to a process for the preparation of compounds of formula (I), Thus, according to a further aspect of the present invention, there is provided a process P1 for the preparation of compounds of formula (I), as herein-defined, as illustrated by the following reaction schemes.

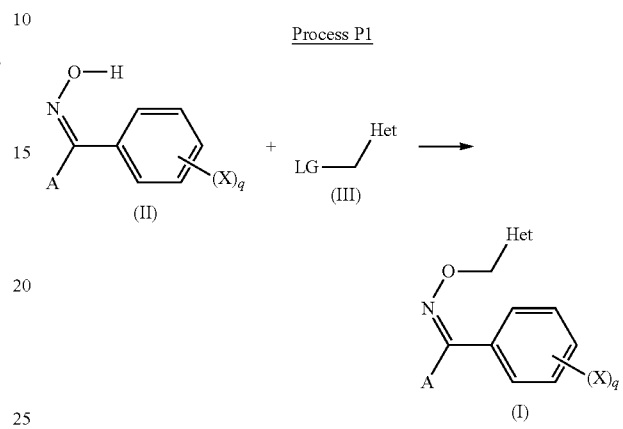

Process P1 wherein A, Het, X, q and Z are as herein-defined and LG represents a leaving group. Suitable leaving groups can be selected in the list consisting of a halogen atom, other customary nucleofugal groups such as triflate, mesylate or tosylate, or a hydroxyl group in the presence of an activating agent such as a combination of a dialkylazodicarboxylate and triphenylphosphine.

According to the invention, there is provided a further process P2 for the preparation of compounds of formula (Ib) from compounds of formula (Ia), by a reaction of alkylation, according to known methods. In such a case there is provided a process P2 according to the invention and such a process P2 can be illustrated by the following reaction scheme:

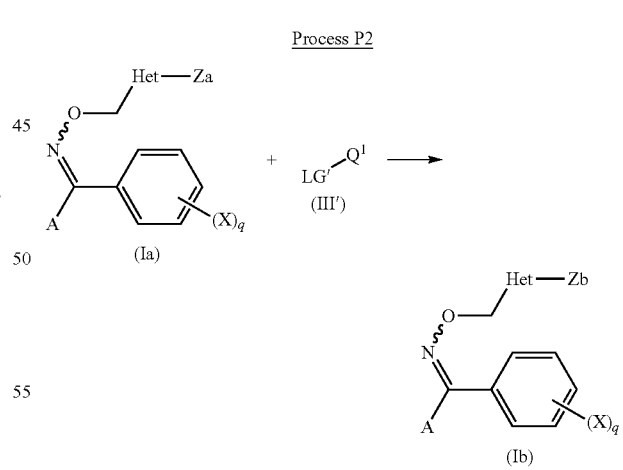

Process P2 wherein
A, Het, X and q are as herein-defined;
LG' represents a leaving group;
$Q^1$ optionally represents substituted or non-substituted $C_1$-$C_8$-alkyl, substituted or non-substituted $C_1$-$C_8$-halogenoalkyl having 1 to 5 halogen atoms, $C_3$-$C_{10}$-cycloalkenyl, $C_3$-$C_{10}$-fused bicycloalkyl, $C_8$-$C_{12}$-fused bicycloalkenyl;

Za represents a hydroxy group, a hydrazino group, a sulphenyl group, carbaldehyde hydroxyl-oxime, hydroxycarbonyl, a carbamoyl group, a N-hydroxycarbamoyl group, a substituted or non-substituted N-hydroxy-($C_1$-$C_8$-alkyl)-amino group, substituted or non-substituted $C_1$-$C_8$-alkoxyamino group, substituted or non-substituted ($C_1$-$C_8$-alkylamino)-amino group, substituted or non-substituted $C_1$-$C_8$-alkylamino, substituted or non-substituted $C_3$-$C_{10}$-cycloalkenylamino, substituted or non-substituted $C_8$-$C_{12}$-fused bicycloalkylamino, substituted or non-substituted $C_8$-$C_{12}$-fused bicycloalkenylamino, substituted or non-substituted phenylamino, an amino group, a formylamino group, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms:

Zb represents substituted or non-substituted a substituted or non-substituted carbaldehyde O—($C_1$-$C_8$-alkyl) oxime, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted $C_1$-$C_8$-alkylamino, substituted or non-substituted $C_3$-$C_{10}$-cycloalkenylamino, substituted or non-substituted $C_8$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted (N—$C_1$-$C_8$-alkyl)-formylamino, substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted $C_1$-$C_8$-alkoxycarbonyl.

Suitable leaving groups can be selected in the list consisting of a halogen atom or other customary nucleofugal groups such as alcoolate, hydroxide, alkylcarboxylate, alkylsulfonate or cyanide.

According to the invention, there is provided a further process P3 for the preparation of compounds of formula (Ic) from compounds of formula (Ia), by a reaction of acylation, alkoxycarbonylation, alkylsulphenylcarbonylation, alkylaminocarbonylation and alkylaminothiocarbonylation, according to known methods. In such a case there is provided a process P3 according to the invention and such a process P3 can be illustrated by the following reaction schemes:

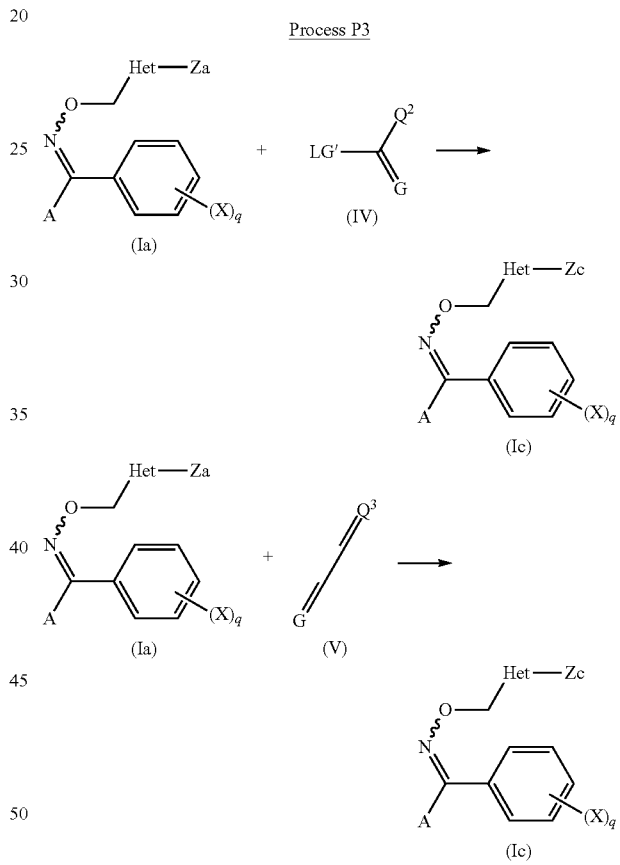

wherein
A, Het, X and q are as herein-defined;
LG' represents a leaving group;
$Q^2$ optionally represents a hydrogen atom, substituted or non-substituted $C_1$-$C_8$-alkyl, substituted or non-substituted $C_1$-$C_8$-halogenoalkyl having 1 to 5 halogen atoms, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted arylsulphenyl;

Q³ represents a substituted or non-substituted C₁-C₈-alkylamino;

Za represents a hydroxy group, a hydrazino group, a sulphenyl group, a substituted or non-substituted N-hydroxy-(C₁-C₈-alkyl)-amino group, substituted or non-substituted C₁-C₈-alkoxyamino group, substituted or non-substituted (C₁-C₈-alkylamino)-amino group, substituted or non-substituted C₁-C₈-alkylamino, substituted or non-substituted C₃-C₁₀-cycloalkenylamino, substituted or non-substituted C₈-C₁₂-fused bicycloalkylamino, substituted or non-substituted C₈-C₁₂-fused bicycloalkenylamino, substituted or non-substituted phenylamino, an amino group, a formylamino group, substituted or non-substituted C₁-C₈-alkylcarbonylamino, substituted or non-substituted C₁-C₈-halogenoalkylcarbonylamino having 1 to 5 halogen atoms, substituted or non-substituted C₁-C₈-alkoxycarbonylamino, substituted or non-substituted C₁-C₈-halogenoalkoxycarbonylamino having 1 to 5 halogen atoms, substituted or non-substituted C₁-C₈-alkylcarbamoylamino, substituted or non-substituted C₁-C₈-halogenoalkylcarbamoylamino having 1 to 5 halogen atoms;

G represents an oxygen atom or a sulphur atom,

Zc represents a formyloxy group, substituted or non-substituted C₁-C₈-alkylcarbonyloxy, substituted or non-substituted C₁-C₈-halogenoalkylcarbonyloxy having 1 to 5 halogen atoms, substituted or non-substituted C₁-C₈-alkylsulphenylcarbonylamino, substituted or non-substituted C₁-C₈-halogenoalkylsulphenylcarbonylamino having 1 to 5 halogen atoms, substituted or non-substituted arylsulphenylcarbonylamino, substituted or non-substituted N-formyl-C₁-C₈-alkylcarbonylamino, substituted or non-substituted N-formyl-C₁-C₈-alkoxycarbonylamino, substituted or non-substituted di-C₁-C₈-alkylcarbonylamino, substituted or non-substituted N—C₁-C₈-alkylcarbonyl-C₁-C₈-alkoxycarbonylamino, substituted or non-substituted C₁-C₈-alkylaminocarbonyloxy, substituted or non-substituted di-C₁-C₈-alkylaminocarbonyloxy, substituted or non-substituted C₁-C₈-alkylcarbamothioyl, substituted or non-substituted di-C₁-C₈-alkylcarbamothioyl, substituted or non-substituted N—C₁-C₈-alkyloxycarbamothioyl, substituted or non-substituted C₁-C₈-alkoxycarbamothioyl, substituted or non-substituted N—C₁-C₈-alkyl-C₁-C₈-alkoxycarbamothioyl, substituted or non-substituted (N—C₁-C₈-alkyl)-C₁-C₈-alkylcarbonylamino, substituted or non-substituted (N—C₁-C₈-alkyl)-C₁-C₈-alkoxycarbonylamino, substituted or non-substituted (N—C₃-C₁₀-cycloakenyl)-formylamino, substituted or non-substituted (N—C₃-C₁₀-cycloalkenyl)-C₁-C₈-alkylcarbonylamino, substituted or non-substituted (N—C₃-C₁₀-cycloalkenyl)-C₁-C₈-alkoxycarbonylamino, substituted or non-substituted (N—C₃-C₁₀-bicycloalkyl)-formylamino, substituted or non-substituted (N—C₃-C₁₀-bicycloalkyl)-C₁-C₈-alkylcarbonylamino, substituted or non-substituted (N—C₃-C₁₀-bicycloalkyl)-C₁-C₈-alkoxycarbonylamino, substituted or non-substituted (N—C₃-C₁₀-bicycloalkenyl)-formylamino, substituted or non-substituted (N—C₃-C₁₀-bicycloalkenyl)-C₁-C₈-alkylcarbonylamino, substituted or non-substituted (N—C₃-C₁₀-bicycloalkenyl)-C₁-C₈-alkoxycarbonylamino, substituted or non-substituted (N-phenyl)-formylamino, substituted or non-substituted (N-phenyl)-C₁-C₈-alkylcarbonylamino, substituted or non-substituted (N-phenyl)-C₁-C₈-alkoxycarbonylamino.

Suitable leaving groups can be selected in the list consisting of a halogen atom or other customary nucleofugal groups such as alcoolate, hydroxide, alkylcarboxylate, alkylsulfonate or cyanide.

According to the invention, there is provided a further process P4 for the preparation of compounds of formula (Ie) from compounds of formula (Id), by a reaction of thiocarbonylation in the presence of a thiocarbonylating agent such as 2,4-bis(4-methoxyphenyl)-1,3,2,4-dithiadiphosphetane 2,4-disulfide, phosphorus pentasulfide, sulphur, according to known methods. In such a case there is provided a process P4 according to the invention and such a process P4 can be illustrated by the following reaction scheme:

Process P4

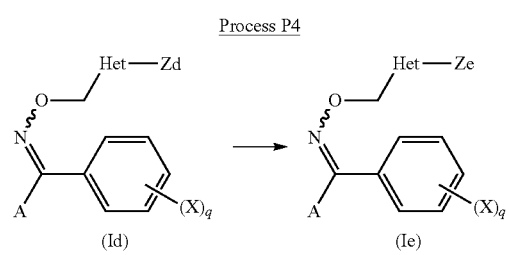

wherein

A, Het, X and q are as herein-defined;

Zd represents a substituted or non-substituted C₁-C₈-alkylcarbamoyl, substituted or non-substituted di-C₁-C₈-alkylcarbamoyl, substituted or non-substituted N—C₁-C₈-alkyloxycarbamoyl, substituted or non-substituted C₁-C₈-alkoxycarbamoyl, substituted or non-substituted N—C₁-C₈-alkyl-C₁-C₈-alkoxycarbamoyl, substituted or non-substituted C₁-C₈-alkylcarbonylamino, substituted or non-substituted C₁-C₈-halogenoalkylcarbonylamino having 1 to 5 halogen atoms, substituted or non-substituted (C₁-C₈-alkyl-carbamoyl)-oxy, substituted or non-substituted substituted or non-substituted (di-C₁-C₈-alkyl-carbamoyl)-oxy, substituted or non-substituted (C₁-C₈-alkyl-carbamoyl)-amino;

Ze represents a substituted or non-substituted C₁-C₈-alkylcarbamothioyl, substituted or non-substituted di-C₁-C₈-alkylcarbamothioyl, substituted or non-substituted N—C₁-C₈-alkyloxycarbamothioyl, substituted or non-substituted C₁-C₈-alkoxycarbamothioyl, substituted or non-substituted N—C₁-C₈-alkyl-C₁-C₈-alkoxycarbamothioyl, substituted or non-substituted C₁-C₈-alkylthioylamino, substituted or non-substituted C₁-C₈-halogenoalkylthioylamino having 1 to 5 halogen atoms, substituted or non-substituted (C₁-C₈-alkyl-carbamothioyl)-oxy, substituted or non-substituted substituted or non-substituted (di-C₁-C₈-alkyl-carbamothioyl)-oxy, substituted or non-substituted (C₁-C₈-alkyl-carbamothioyl)-amino, substituted or non-substituted substituted or non-substituted (di-C₁-C₈-alkyl-carbamothioyl)-amino.

According to the invention, there is provided a further process P5 for the preparation of compounds of formula (Ig) from compounds of formula (If), by a reaction of nucleophilic substitution to yield to a compound of formula (Ig), according to known methods, optionally in the presence of carbon monoxide or a carbon monoxide generating agent such as Mo(CO)₆ or W(CO)₆, optionally in the presence of a catalyst notably a transition metal catalyst, such as palladium salts or complexes for example palladium (II) chloride, palladium (II) acetate, tetrakis-(triphenylphosphine) palladium(0), bis- (triphenylphosphine) palladium dichloride (II), tris(dibenzylideneacetone) dipalladium(0), bis(dibenzylideneacetone) palladium(0) or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine) butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino) ferrocenyl]ethyldi-tert-butylphosphine, (S)-(+)-1-[(R)-2-(diphenylphosphino)ferrocenyl] ethyldicyclohexylphosphine, (R)-(−)-1-[(S)-2-(diphenylphosphino)ferrocenyl] ethyldicyclohexylphosphine, (S)-(+)-1-[(R)-2-(diphenylphosphino)ferrocenyl]ethyldi-t-butylphosphine, optionally in the presence of a base such as an inorganic or an organic base; preferably an alkaline earth metal or alkali metal hydride, hydroxide, amide, alcoholate, acetate, carbonate or hydrogen carbonate, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), according to known methods. In such a case there is provided a process P5 according to the invention and such a process P5 can be illustrated by the following reaction scheme:

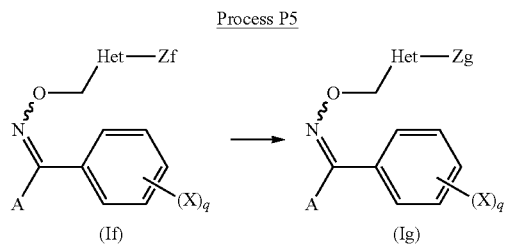

Process P5 wherein
A, Het, X, and q are as herein-defined;
Zf represents a halogen atom;
Zg represents a represents a hydroxy group, a cyano group, a sulphenyl group, a formyl group, hydroxycarbonyl, substituted or non-substituted $C_1$-$C_8$-alkoxycarbonyl, substituted or non-substituted ($C_1$-$C_8$-alkyl carbonyl)-$C_1$-$C_8$-alkyl, substituted or non-substituted ($C_1$-$C_8$-alkoxycarbonyl)-$C_1$-$C_8$-alkyl, a formyloxy group, a carbamoyl group, a N-hydroxycarbamoyl group, a substituted or non-substituted N-hydroxy-($C_1$-$C_8$-alkyl)-amino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_8$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylsulphenylcarbonylamino, substituted or non-substituted $C_1$-$C_8$-halogenoalkylsulphenylcarbonylamino having 1 to 5 halogen atoms, substituted or non-substituted arylsulphenylcarbonylamino, substituted or non-substituted N-formyl-$C_1$-$C_8$-alkylcarbonylamino, substituted or non-substituted N-formyl-$C_1$-$C_8$-alkoxycarbonylamino, substituted or non-substituted di-$C_1$-$C_8$-alkylcarbonylamino, substituted or non-substituted N—$C_1$-$C_8$-alkylcarbonyl-$C_1$-$C_8$-alkoxycarbonylamino, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylsulphenyl, substituted or non-substituted $C_1$-$C_8$-halogenoalkylsulphenyl having 1 to 5 halogen atoms, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulphenyl, substituted or non-substituted phenoxy, substituted or non-substituted phenylsulphenyl, substituted or non-substituted aryl, substituted or non-substituted heterocyclyl, substituted or non-substituted aryl-[$C_1$-$C_8$]-alkyl, substituted or non-substituted $C_1$-$C_8$-alkylamino, substituted or non-substituted $C_3$-$C_{10}$-cycloakenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted (N—$C_1$-$C_8$-alkyl)-formylamino, substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted (N-phenyl)-formylamino, substituted or non-substituted (N-phenyl)-$C_1$-$C_8$-alkylcarbonylamino, substituted or non-substituted (N-phenyl)-$C_1$-$C_8$-alkoxycarbonylamino.

According to the invention, there is provided a further process P6 for the preparation of compounds of formula (Ii) from compounds of formula (Ih), by a reaction of deprotection, according to known methods. In such a case there is provided a process P6 according to the invention and such a process P6 can be illustrated by the following reaction scheme:

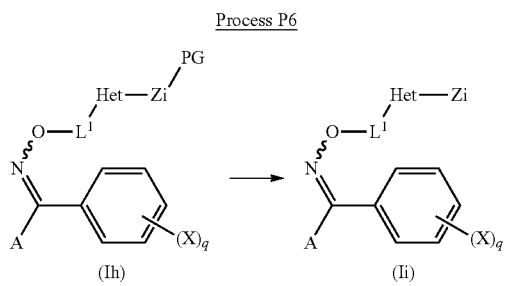

wherein
A, Het, X, q, Z, $L^1$ and q are as herein-defined;
PG represents a protecting group such as a formyl group, $C_1$-$C_8$-alkylcarbonyl, $C_1$-$C_8$-alkoxycarbonyl, $C_1$-$C_8$-alkoxy-$C_1$-$C_2$-alkyl, tri($C_1$-$C_8$-alkyl)silyl-$C_1$-$C_2$-alkyl, tri($C_1$-$C_8$-alkyl)silyloxy-$C_1$-$C_2$-alkyl;
Zi represents a substituted or non-substituted $C_1$-$C_8$-alkoxyamino, a substituted or non-substituted $C_1$-$C_8$-alkylamino, substituted or non-substituted $C_3$-$C_{10}$-cycloakenylamino, substituted or non-substituted $C_8$-$C_{12}$-fused bicycloalkylamino, substituted or non-substituted $C_8$-$C_{12}$-fused bicycloalkenylamino, substituted or non-substituted di-$C_1$-$C_8$-alkylamino, substituted or non-substituted phenylamino.

Amino-protecting groups and related methods of cleavage thereof are known and can be found in T. W. Greene and P. G. M. Wuts, *Protective Group in Organic Chemistry*, 3$^{rd}$ ed., John Wiley & Sons.

According to the invention, there is provided a further process P7 for the preparation of compounds of formula (Ik) from compounds of formula (Ij) by a reaction of amino-reduction, in the presence of a reducing agent, such as hydrogen gas or an hydride derivative, in particular sodium cyanoborohydride, according to known methods. In such a case there is provided a process P7 according to the invention and such a process P7 can be illustrated by the following reaction scheme:

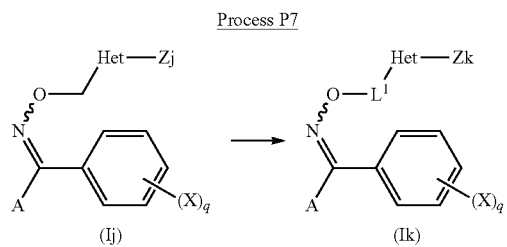

wherein
A, Het, X and q are as herein-defined;
Zj represents an amino group, a substituted or non-substituted $C_1$-$C_8$-alkylamino;
Zk represents a substituted or non-substituted $C_1$-$C_8$-alkylamino, substituted or non-substituted $C_3$-$C_{10}$-cycloakenylamino, substituted or non-substituted $C_8$-$C_{12}$-fused bicycloalkylamino, substituted or non-substituted $C_8$-$C_{12}$-fused bicycloalkenylamino, substituted or non-substituted di-$C_1$-$C_8$-alkylamino.

According to the invention, there is provided a further process $P^a$ for the preparation of compounds of formula (In) from compounds of formula (Im), by a reaction of conversion of a amino group to halide via diazotization, in the presence of a halide salt, preferentially a copper halide salt, according to known methods. In such a case there is provided a process $P^a$ according to the invention and such a process $P^a$ can be illustrated by the following reaction scheme:

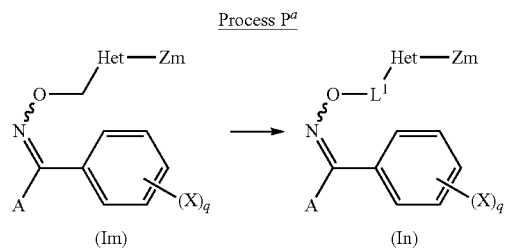

wherein
A, Het, X and q are as herein-defined;
Zm represents an amino group;
Zn represents a halogen atom.

According to the invention, processes P1, P2 and P3 can be performed if appropriate in the presence of a solvent and if appropriate in the presence of a base.

According to the invention, processes P1 and P2 can be performed if appropriate in the presence of a catalyst. Suitable catalyst can be chosen as being 4-dimethyl-aminopyridine, 1-hydroxy-benzotriazole or dimethylformamide.

In case LG' represents a hydroxy group, the process P2 according to the present invention can be performed in the presence of condensing agent. Suitable condensing agent can be chosen as being acid halide former, such as phosgene, phosphorous tri-bromide, phosphorous trichloride, phosphorous pentachloride, phosphorous trichloride oxide or thionyl chloride; anhydride former, such as ethyl chloroformate, methyl chloroformate, isopropyl chloroformate, isobutyl chloroformate or methanesulfonyl chloride; carbodiimides, such as N,N'-dicyclohexylcarbodiimide (DCC) or other customary condensing agents, such as phosphorous pentoxide, polyphosphoric acid, N,N'-carbonyl-diimidazole, 2-ethoxy-N-ethoxycarbonyl-1,2-dihydroquinoline (EEDQ), triphenylphosphine/tetrachloromethane, 4-(4,6-dimethoxy[1.3.5] triazin-2-yl)-4-methylmorpholinium chloride hydrate or bromo-tripyrrolidino-phosphonium-hexafluorophosphate.

Suitable solvents for carrying out processes P1 to P7 and P$^a$ according to the invention are customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichlorethane or trichlorethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or iso-butyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide or sulphones, such as sulpholane.

Suitable bases for carrying out processes P1 and P2 according to the invention are inorganic and organic bases which are customary for such reactions. Preference is given to using alkaline earth metal, alkali metal hydride, alkali metal hydroxides or alkali metal alkoxides, such as sodium hydroxide, sodium hydride, calcium hydroxide, potassium hydroxide, potassium tert-butoxide or other ammonium hydroxide, alkali metal carbonates, such as sodium carbonate, potassium carbonate, potassium bicarbonate, sodium bicarbonate, cesium carbonate, alkali metal or alkaline earth metal acetates, such as sodium acetate, potassium acetate, calcium acetate and also tertiary amines, such as trimethylamine, triethylamine, diisopropylethylamine, tributylamine, N,N-dimethylaniline, pyridine, N-methylpiperidine, N,N-dimethylaminopyridine, 1,4-diazabicyclo[2.2.2]octane (DABCO), 1,5-diazabicyclo[4.3.0]non-5-ene (DBN) or 1,8-diazabicyclo[5.4.0]undec-7-ene (DBU).

If carrying out processes P1 to P7 and P$^a$ according to the invention, the reaction temperature can independently be varied within a relatively wide range. Generally, process P1 according to the invention is carried out at temperatures between −80° C. and 160° C.

Processes P1 to P7 and P$^a$ according to the invention are generally independently carried out under atmospheric pressure. However, it is also possible to operate under elevated or reduced pressure.

Work-up is carried out by customary methods. Generally, the reaction mixture is treated with water and the organic phase is separated off and, after drying, concentrated under reduced pressure. If appropriate, the remaining residue can be freed by customary methods, such as chromatography or recrystallization, from any impurities that can still be present.

Compounds according to the invention can be prepared according to the above described processes. It will nevertheless be understood that, on the basis of his general knowledge and of available publications, the skilled worker will be able to adapt these processes according to the specifics of each of the compounds according to the invention that is desired to be synthesised.

If A represents a group of formula (A$^1$), as herein-described, the compounds of formula (II), useful as a starting material, can be prepared, for example, by reacting hydroxylamine with the corresponding ketones that can be prepared, for example, according to the method described by R. Raap (*Can. J. Chem.* 1971, 49, 2139) by addition of a tetrazolyl metalated species to esters of formula

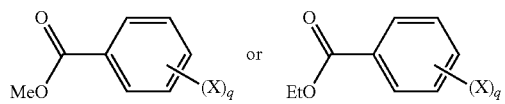

or any of their suitable synthetic equivalents like, for example:

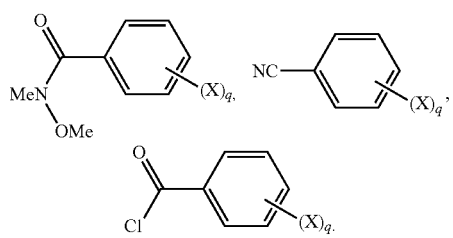

If A represents a group of formula A$^2$, as herein-described, the compounds of formula (II) useful as a starting material, can be prepared, for example, from oximes of formula

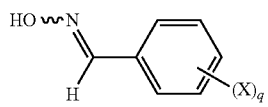

and 5-substituted tetrazole according to the method described by J. Plenkiewicz et al. (*Bull. Soc. Chim. Belg.* 1987, 96, 675).

In a further aspect, the present invention relates to compounds of formula (III) useful as intermediate compounds or materials for the process of preparation according to the invention. The present invention thus provides compounds of formula (IIIa)

wherein LG is as herein-defined and Het represents (Het$^1$), or (Het$^3$);

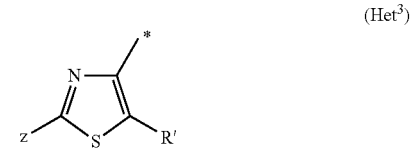

Wherein R, R' and n are as herein-defined and Z represents a substituted or non-substituted C$_2$-C$_8$-alkynyl;

Preferred compounds of formula (IIIa) are those wherein Z represents a substituted or non-substituted $C_2$-$C_8$-alkynyl, Het represents (Het³) and R' is a hydrogen atom.

The present invention thus provides compounds of formula (IIIb)

wherein LG is as herein-defined and Het represents (Het²) or (Het⁴);

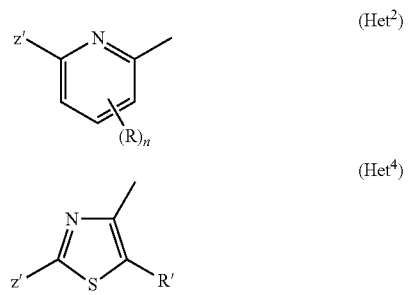

Wherein R, R' represent a hydrogen atom and n is as herein-defined and

Z' represents substituted or non-substituted N-formyl-$C_1$-$C_8$-alkylcarbonylamino, substituted or non-substituted N-formyl-$C_1$-$C_8$-alkoxycarbonylamino, substituted or non-substituted di-$C_1$-$C_8$-alkylcarbonylamino, substituted or non-substituted N—$C_1$-$C_8$-alkylcarbonyl-$C_1$-$C_8$-alkoxycarbonylamino, substituted or non-substituted $C_1$-$C_8$-alkylamino, substituted or non-substituted $C_3$-$C_{10}$-cycloalkenylamino, substituted or non-substituted $C_5$-$C_{12}$-fused bicycloalkylamino, substituted or non-substituted $C_5$-$C_{12}$-fused bicycloalkenylamino, substituted or non-substituted di-$C_1$-$C_8$-alkylamino, substituted or non-substituted phenylamino, substituted or non-substituted (N—$C_1$-$C_8$-alkyl)-formylamino, substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted (N-phenyl)-formylamino, substituted or non-substituted (N-phenyl)-$C_1$-$C_8$-alkylcarbonylamino, substituted or non-substituted (N-phenyl)-$C_1$-$C_8$-alkoxycarbonylamino; provided that compounds of formula (IIIb), as herein-defined, do not represent a compound of the following list:

Acetamide, N-acetyl-N-[6-(bromomethyl)-2-pyridinyl]-; Carbamic acid, N-[6-(bromomethyl)-2-pyridinyl]-N-methyl-, 1,1-dimethylethyl ester; Formamide, N-[6-(chloromethyl)-2-pyridinyl]-N-pentyl-; Carbamic acid, N-[6-(hydroxymethyl)-2-pyridinyl]-N-methyl-, 1,1-dimethylethyl ester; Acetamide, N-[4-(chloromethyl)-2-thiazolyl]-N-ethyl-; Propanamide, N-[4-(chloromethyl)-2-thiazolyl]-N-methyl-; Acetamide, N-[4-(chloromethyl)-2-thiazolyl]-N-(4-nitrophenyl)-; 2-(N-Acetylmethylamino)-4-chloromethylthiazole; 2-Pyridinemethanol, 6-[(2,2-dimethylpropyl)amino]-; 2-Pyridinemethanol, 6-(methylamino)-; 2-Methylamino-4-chloromethylthiazole.

Preferred compounds of formula (IIIb) are those wherein Het represents (Het²).

In a further aspect of the invention, there is provided a process P8 for the preparation of compounds of formula (IIIb) wherein Het represents (Het²) and LG represents a halogen atom, from compounds of formula (IIIb') wherein Het represents (Het²) and LG represents an hydroxyl group, according to known methods. In such a case there is provided a process P8 according to the invention and such a process P8 can be illustrated by the following reaction scheme:

Process P8

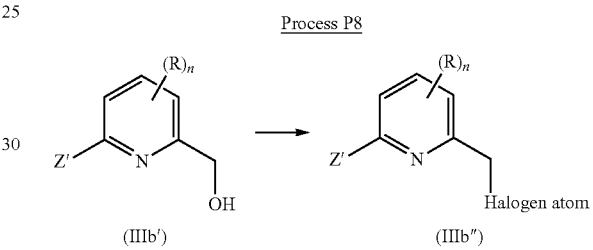

wherein R and n are as herein-defined,

Z' represents substituted or non-substituted N-formyl-$C_1$-$C_8$-alkylcarbonylamino, substituted or non-substituted N-formyl-$C_1$-$C_8$-alkoxycarbonylamino, substituted or non-substituted di-$C_1$-$C_8$-alkylcarbonylamino, substituted or non-substituted N—$C_1$-$C_8$-alkylcarbonyl-$C_1$-$C_8$-alkoxycarbonylamino, substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted (N-phenyl)-formylamino, substituted or non-substituted (N-phenyl)-$C_1$-$C_8$-alkylcarbonylamino, substituted or non-substituted (N-phenyl)-$C_1$-$C_8$-alkoxycarbonylamino.

In a further aspect of the invention, there is provided a process P9 for the preparation of compounds of formula (IIIb') wherein Het represents (Het²), n is 0 and LG represents an hydroxyl group, from compounds of formula (X), by a reaction of reduction, notably by sodium borohydride, according to known methods. In such a case there is provided a process P9 according to the invention and such a process P9 can be illustrated by the following reaction scheme:

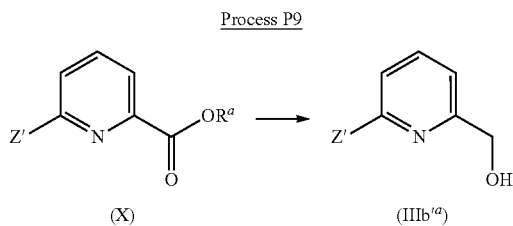

Process P9

(X) → (IIIb'$^a$)

wherein Z' represents substituted or non-substituted N-formyl-$C_1$-$C_8$-alkylcarbonylamino, substituted or non-substituted N-formyl-$C_1$-$C_8$-alkoxycarbonylamino, substituted or non-substituted di-$C_1$-$C_8$-alkylcarbonylamino, substituted or non-substituted N—$C_1$-$C_8$-alkylcarbonyl-$C_1$-$C_8$-alkoxycarbonylamino, substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted (N-phenyl)-formylamino, substituted or non-substituted (N-phenyl)-$C_1$-$C_8$-alkylcarbonylamino, substituted or non-substituted (N-phenyl)-$C_1$-$C_8$-alkoxycarbonylamino, and $R^a$ represents a $C_1$-$C_8$ alkyl.

In a further aspect of the invention, there is provided a process P10 for the preparation of compounds of formula (X) wherein Z' represents substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-$C_1$-$C_8$-alkoxycarbonylamino, substituted or non-substituted (N-phenyl)-$C_1$-$C_8$-alkoxycarbonylamino, from compounds of formula (XI), by a reaction of alkylation, notably in the presence of a base, according to known methods. Compounds of formula (XI) can be prepared by a Curtius reaction directly from compounds of formula (XII) or via a Hofmann rearrangement from compounds of formula (XIII) which can be obtained by amidification of compounds of formula (XII), according to known methods. In such a case there is provided a process P10 according to the invention and such a process P10 can be illustrated by the following reaction schemes:

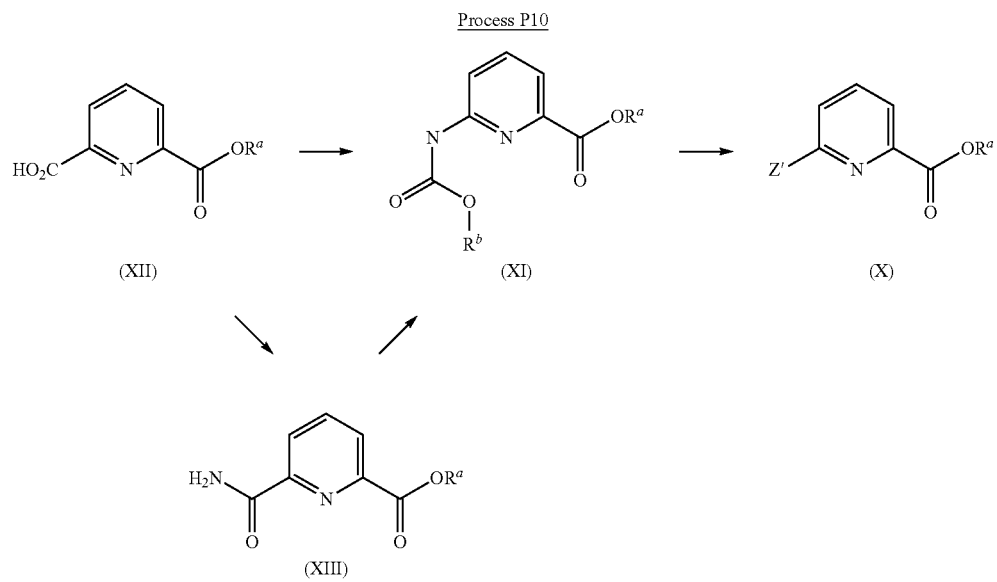

Process P10

(XII) → (XI) → (X)

(XIII)

wherein $R^a$ represents a $C_1$-$C_8$ alkyl
and $R^b$ represents a $C_1$-$C_8$ alkyl.

In a further aspect of the invention, there is provided a process P11 for the preparation of compounds of formula (IIIb') wherein Het represents (Het$^2$), n is 0 and LG represents an hydroxyl group, from compounds of formula (XV), by a reaction of reduction, notably by sodium borohydride, according to known methods. Compounds of formula (XV) can be prepared by addition on an electrophilic specie, such as DMF, of a metalated pyridine after halogen-metal exchange on a compound of formula (XVI), according to known methods. Compounds of Formula (XVI) can be obtained by acylation of 2-bromo-6-amino-pyridine, according to known methods Optionally, compounds of formula (IIIb') wherein Het represents (Het$^2$), n is 0 and LG represents an hydroxyl group can undergo a reaction of alkylation, according to known methods. In such a case there is provided a process P11 according to the invention and such a process P11 can be illustrated by the following reaction scheme:

Process P11

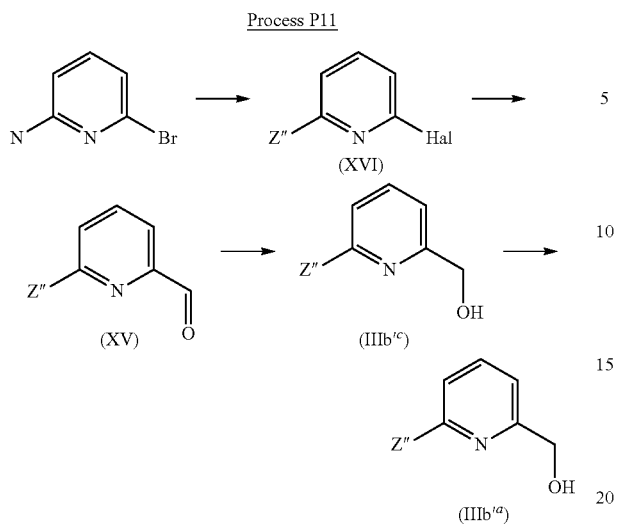

Process P12

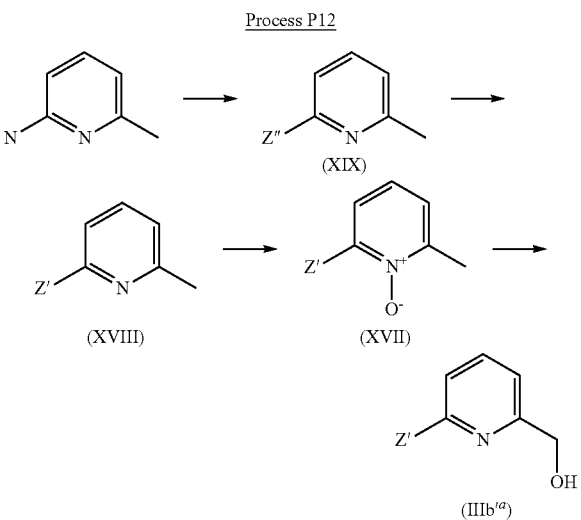

wherein Z' represents substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{18}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted (N-phenyl)-formylamino, substituted or non-substituted (N-phenyl)-$C_1$-$C_8$-alkylcarbonylamino, substituted or non-substituted (N-phenyl)-$C_1$-$C_8$-alkoxycarbonylamino, Z" represents substituted or non-substituted formylamino, substituted or non-substituted $C_1$-$C_8$-alkylcarbonylamino, substituted or non-substituted $C_1$-$C_8$-alkoxycarbonylamino, And Hal represents a halogen atom.

In a further aspect of the invention, there is provided a process P12 for the preparation of compounds of formula (IIIb'), wherein Het represents (Het²), and LG represents an hydroxyl group, from compounds of formula (XVII), by a Polonovsky reaction, notably by using a carboxylic acid anhydride, optionally as solvent, such as acetic anhydride or trifluoroacetic anhydride, according to known methods. Compounds of formula (XVII) can be prepared by oxidation of the pyridyl core of a compound of formula (XVIII), according to known methods. Compounds of formula (XVIII) can be prepared by a reaction of alkylation on a compound of formula (XIX), according to known methods. Compounds of Formula (XIX) can be obtained by acylation of 2-amino-6-methyl-pyridine, according to known methods. In such a case there is provided a process P12 according to the invention and such a process P12 can be illustrated by the following reaction scheme:

Wherein Z' represents substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted (N-phenyl)-formylamino, substituted or non-substituted (N-phenyl)-$C_1$-$C_8$-alkylcarbonylamino, substituted or non-substituted (N-phenyl)-$C_1$-$C_8$-alkoxycarbonylamino, Z" represents substituted or non-substituted formylamino, substituted or non-substituted $C_1$-$C_8$-alkylcarbonylamino, substituted or non-substituted $C_1$-$C_8$-alkoxycarbonylamino.

In a further aspect of the invention, there is provided a process P13 for the preparation of compounds of formula (IIIb), wherein Het represents (Het²), and LG represents a halogen atom from a compound of formula (XVII) by a reaction of halogeno-methylation of pyridine-oxides, in the presence of an activating agent such as tosyle chloride, thionyl chloride or thionyl bromide, according to known methods, for example *Tetrahedron* 1982 (38) p 3277. In such a case there is provided a process P13 according to the invention and such a process P13 can be illustrated by the following reaction scheme:

Process P13

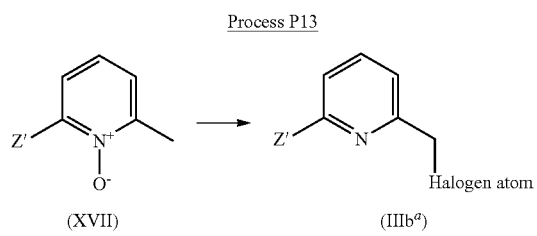

Wherein Z' represents substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted (N-phenyl)-formylamino, substituted or non-substituted (N-phenyl)-$C_1$-$C_8$-alkylcarbonylamino, substituted or non-substituted (N-phenyl)-$C_1$-$C_8$-alkoxycarbonylamino.

In a further aspect of the invention, there is provided a process P14 for the preparation of compounds of formula (IIIb), wherein Het represents (Het²), and LG represents a halogen atom from a compound of formula (XVIII) by a reaction of radical halogenation, in the presence of an halogenating agent such as elemental chlorine, elemental bromine, N-halogeno succinimide or di-halo-dimethylhydantoïne, optionally in the presence of a radical initiator such as azoisobutyronitrile or triethylborane, optionally under ultraviolet irradiation, according to known methods. In such a case there is provided a process P14 according to the invention and such a process P14 can be illustrated by the following reaction scheme:

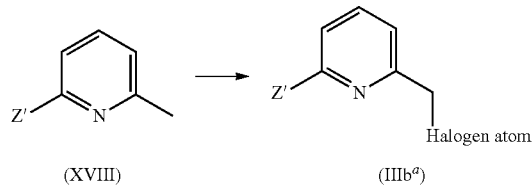

Process P14

(XVIII) (IIIb$^a$)

Wherein Z' represents substituted or non-substituted (N—$C_1$-$C_8$-alkyl)-$C_1$-$C_8$-alkylcarbonylamino, substituted or non-substituted (N—$C_1$-$C_8$-alkyl)-$C_1$-$C_8$-alkoxycarbonylamino, substituted or non-substituted (N—$C_3$-$C_{10}$-cycloalkenyl)-formylamino, substituted or non-substituted (N—$C_3$-$C_{10}$-cycloalkenyl)-$C_1$-$C_8$-alkylcarbonylamino, substituted or non-substituted (N—$C_3$-$C_{10}$-cycloalkenyl)-$C_1$-$C_8$-alkoxycarbonylamino, substituted or non-substituted (N—$C_3$-$C_{10}$-bicycloalkyl)-formylamino, substituted or non-substituted (N—$C_3$-$C_{10}$-bicycloalkyl)-$C_1$-$C_8$-alkylcarbonylamino, substituted or non-substituted (N—$C_3$-$C_{10}$-bicycloalkyl)-$C_1$-$C_8$-alkoxycarbonylamino, substituted or non-substituted (N—$C_3$-$C_{10}$-bicycloalkenyl)-formylamino, substituted or non-substituted (N—$C_3$-$C_{10}$-bicycloalkenyl)-$C_1$-$C_8$-alkylcarbonylamino, substituted or non-substituted (N—$C_3$-$C_{10}$-bicycloalkenyl)-$C_1$-$C_8$-alkoxycarbonylamino, substituted or non-substituted (N-phenyl)-formylamino, substituted or non-substituted (N-phenyl)-$C_1$-$C_8$-alkylcarbonylamino, substituted or non-substituted (N-phenyl)-$C_1$-$C_8$-alkoxycarbonylamino.

In a further aspect of the invention, there is provided a process P15 for the preparation of compounds of formula (IIIb') wherein Het represents (Het²) and LG represents an hydroxyl group from compounds of formula (XX), by a reaction of nucleophilic, optionally in the presence of a catalyst notably a transition metal catalyst, such as palladium salts or complexes for example palladium (II) chloride, palladium (II) acetate, tetrakis-(triphenylphosphine) palladium(0), bis-(triphenylphosphine) palladium dichloride (II), tris(dibenzylideneacetone) dipalladium(0), bis(dibenzylideneacetone) palladium(0) or 1,1'-bis(diphenylphosphino)ferrocene-palladium (II) chloride. As an alternative the palladium complex is directly generated in the reaction mixture by separately adding to the reaction mixture a palladium salt and a complex ligand such as a phosphine, for example triethylphosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino)-biphenyl, triphenylphosphine, tris-(o-tolyl)phosphine, sodium 3-(diphenylphosphino)benzolsulfonate, tris-2-(methoxyphenyl)phosphine, 2,2'-bis-(diphenylphosphine)-1,1'-binaphthyl, 1,4-bis-(diphenylphosphine)butane, 1,2-bis-(diphenylphosphine)ethane, 1,4-bis-(dicyclohexylphosphine)butane, 1,2-bis-(dicyclohexylphosphine)ethane, 2-(dicyclohexylphosphine)-2'-(N,N-dimethylamino)-biphenyl, bis(diphenylphosphino)ferrocene, tris-(2,4-tert-butylphenyl)-phosphite, (R)-(−)-1-[(S)-2-(diphenylphosphino)ferrocenyl]ethyldi-tert-butylphosphine, (S)-(+)-1-[(R)-2-(diphenylphosphino)ferrocenyl]ethyldicyclohexylphosphine, (R)-(−)-1-[(S)-2-(diphenylphosphino)ferrocenyl]ethyldicyclohexylphosphine, (S)-(+)-1-[(R)-2-(diphenylphosphino)ferrocenyl]ethyldi-t-butylphosphine, optionally in the presence of a base to such as an inorganic or an organic base; preferably an alkaline earth metal or alkali metal hydride, hydroxide, amide, alcoholate, acetate, carbonate or hydrogen carbonate, such as sodium hydride, sodium amide, lithium diisopropylamide, sodium methanolate, sodium ethanolate, potassium tert-butanolate, sodium acetate, potassium acetate, calcium acetate, sodium hydroxide, potassium hydroxide, sodium carbonate, potassium carbonate, potassium bicarbonate, sodium bicarbonate, cesium carbonate or ammonium carbonate; and also tertiary amine, such as trimethylamine, triethylamine (TEA), tributylamine, N,N-dimethylaniline, N,N-dimethyl-benzylamine, N,N-diisopropyl-ethylamine (DIPEA), pyridine, N-methylpiperidine, N-methylmorpholine, N,N-dimethylaminopyridine, diazabicyclooctane (DABCO), diazabicyclononene (DBN) or diazabicycloundecene (DBU), according to known methods, for example *Journal of American chemical society*, 2008 (130) p 6586. In such a case there is provided a process P15 according to the invention and such a process P15 can be illustrated by the following reaction scheme:

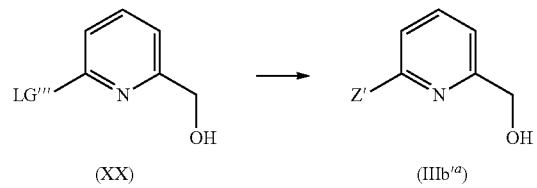

Process P15

(XX) (IIIb'$^a$)

Wherein Z' represents substituted or non-substituted $C_1$-$C_8$-alkylamino, substituted or non-substituted $C_3$-$C_{10}$-cycloalkenyl-amino, substituted or non-substituted $C_3$-$C_{10}$-bicycloalkylamino, substituted or non-substituted $C_3$-$C_{10}$-bicycloalkenylamino, substituted or non-substituted N-phenylamino, And LG''' represents a halogen atom, a tosylate or a triflate.

The present invention thus provides compounds of formula (X), (XI), (XV), (XVII) and (XVIII), as herein-described; provided that:
  compounds of formula (X), as herein-defined, do not represent a compound of the following list:
    2-Pyridinecarboxylic acid, 6-[[(1,1-dimethylethoxy)carbonyl]methylamino]-, ethyl ester;
  compounds of formula (XI), as herein-defined, do not represent a compound of the following list:
    Methyl 6-[(tert-butoxycarbonyl)amino]pyridine-2-carboxylate; 6-[(tert-Butoxycarbonyl)amino]pyridine-2-carboxylic acid ethyl ester
  compounds of formula (XVIII), as herein-defined, do not represent a compound of the following list:
    Carbamic acid, ethyl(6-methyl-2-pyridinyl)-, 1,1-dimethylethyl ester; Carbamic acid, methyl(6-methyl-2-pyridinyl)-, 1,1-dimethylethyl ester; tetradecanamide, N-methyl-N-(6-methyl-2-pyridinyl)-; Nonanamide, 7-(difluoromethylene)-N-methyl-N-(6-methyl-2-pyridinyl)-
  compounds of formula (XV), as herein-defined, do not represent a compound of the following list:
    tert-Butyl (6-formylpyridin-2-yl)carbamate; 6-((2,2-Dimethylpropanoyl)amino)pyridine-2-carboxaldehyde; 2-(Acetylamino)pyridine-6-carboxaldehyde
  compounds of formula (XVI), as herein-defined, do not represent a compound of the following list:
    Formamide, N-(6-fluoro-2-pyridinyl)-; Propanamide, N-(6-bromo-2-pyridinyl)-; Propanamide, N-(6-iodo-2-pyridinyl)-2,2-dimethyl-; Dodecanamide, N-(6-bromo-2-pyridinyl)-; N-(6-Bromo-2-pyridinyl)-2-methylpropanamide; Acetamide, N-(6-fluoro-2-pyridinyl)-; 6-Bromo-2-pivaloylaminopyridine; Propanamide, N-(6-fluoro-2-pyridinyl)-2,2-dimethyl-; 6-Chloro-2-(pivaloylamino)pyridine; Acetamide, N-(6-chloro-2-pyridinyl)-; 2-Acetamido-6-bromopyridine
  compounds of formula (XVII), as herein-defined, do not represent a compound of the following list:
    Carbamic acid, N-methyl-N-(6-methyl-1-oxido-2-pyridinyl)-, 1,1-dimethylethyl ester; carbamic acid, (6-methyl-1-oxido-2-pyridinyl)-, ethyl In a further aspect, the present invention also relates to a fungicide composition comprising an effective and non-phytotoxic amount of an active compound of formula (I).

The expression "effective and non-phytotoxic amount" means an amount of composition according to the invention which is sufficient to control or destroy the fungi present or liable to appear on the crops and which does not entail any appreciable symptom of phytotoxicity for the said crops. Such an amount can vary within a wide range depending on the fungus to be controlled, the type of crop, the climatic conditions and the compounds included in the fungicide composition according to the invention. This amount can be determined by systematic field trials, which are within the capabilities of a person skilled in the art.

Thus, according to the invention, there is provided a fungicide composition comprising, as an active ingredient, an effective amount of a compound of formula (I) as herein defined and an agriculturally acceptable support, carrier or filler.

According to the invention, the term "support" denotes a natural or synthetic organic or inorganic compound with which the active compound of formula (I) is combined or associated to make it easier to apply, notably to the parts of the plant. This support is thus generally inert and should be agriculturally acceptable. The support can be a solid or a liquid. Examples of suitable supports include cleans, natural or synthetic silicates, silica, resins, waxes, solid fertilisers, water, alcohols, in particular butanol organic solvents, mineral and plant oils and derivatives thereof. Mixtures of such supports can also be used.

The composition according to the invention can also comprise additional components. In particular, the composition can further comprise a surfactant. The surfactant can be an emulsifier, a dispersing agent or a wetting agent of ionic or non-ionic type or a mixture of such surfactants. Mention can be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols and derivatives of the above compounds containing sulphate, sulphonate and phosphate functions. The presence of at least one surfactant is generally essential if the active compound and/or the inert support are water-insoluble and if the vector agent for the application is water. Preferably, surfactant content can be comprised from 5% to 40% by weight of the composition.

Optionally, additional components can also be included, e.g. protective colloids, adhesives, thickeners, thixotropic agents, penetration agents, stabilisers, sequestering agents. More generally, the active compounds can be combined with any solid or liquid additive, which complies with the usual formulation techniques.

In general, the composition according to the invention can contain from 0.05 to 99% by weight of active compound, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ULV) liquid, ultra low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a sprcaning or dusting device, but also concentrated commercial compositions which must be diluted before application to the crop.

The compounds according to the invention can also be mixed with one or more insecticide, fungicide, bactericide, attractant, acaricide or pheromone active substance or other compounds with biological activity. The mixtures thus obtained have a broadened spectrum of activity. The mixtures with other fungicide compounds are particularly advantageous. The composition according to the invention comprising a mixture of a compound of formula (I) with a bactericide compound can also be particularly advantageous According to another object of the present invention, there is provided a method for controlling the phytopathogenic fungi of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clcan), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to grow.

The expression "are applied to the plants to be treated" is understood to mean, for the purposes of the present invention, that the pesticide composition which is the subject of the invention can be applied by means of various methods of treatment such as:
- spraying onto the aerial parts of the said plants a liquid comprising one of the said compositions,
- dusting, the incorporation into the soil of granules or powders, sprcaning, around the said plants and in the case of trees injection or daubing,
- coating or film-coating the seeds of the said plants with the aid of a plant-protection mixture comprising one of the said compositions.

The method according to the invention can either be a curing, preventing or eradicating method. In this method, a composition used can be prepared beforehand by mixing the two or more active compounds according to the invention.

According to an alternative of such a method, it is also possible to apply simultaneously, successively or separately compounds (A) and (B) so as to have the conjugated (A)/(B) effects, of distinct compositions each containing one of the two or three active ingredients (A) or (B).

The dose of active compound usually applied in the method of treatment according to the invention is generally and advantageously
- for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;
- for seed treatment: from 2 to 200 g per 100 kilogram of seed, preferably from 3 to 150 g per 100 kilogram of seed;
- for soil treatment: from 0.1 to 10,000 g/ha, preferably from 1 to 5,000 g/ha.

The doses herein indicated are given as illustrative Examples of method according to the invention. A person skilled in the art will know how to adapt the application doses, notably according to the nature of the plant or crop to be treated.

Under specific conditions, for example according to the nature of the phytopathogenic fungus to be treated or controlled, a lower dose can offer adequate protection. Certain climatic conditions, resistance or other factors like the nature of the phytopathogenic fungi or the degree of infestation, for example, of the plants with these fungi, can require higher doses of combined active ingredients. The optimum dose usually depends on several factors, for example on the type of phytopathogenic fungus to be treated, on the type or level of development of the infested plant, on the density of vegetation or alternatively on the method of application.

Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant.

Among the plants that can be protected by the method according to the invention, mention can be made of cotton; flax; vine; fruit or vegetable crops such as *Rosaceae* sp. (for instance pip fruit such as apples and pears, but also stone fruit such as apricots, almonds and peaches), *Ribesioidae* sp., *Juglandaceae* sp., *Betulaceae* sp., *Anacardiaceae* sp., *Fagaceae* sp., *Moraceae* sp., *Oleaceae* sp., Actimidaceae sp., *Lauraceae* sp., *Musaceae* sp. (for instance banana trees and plantins), *Rubiaceae* sp., *Theaceae* sp., *Sterculiceae* sp., *Rutaceae* sp. (for instance lemons oranges and grapefruit); *Solanaceae* sp. (for instance tomatoes), *Liliaceae* sp., *Asteraceae* sp. (for instance lettuces), *Umbelliferae* sp., *Cruciferae* sp., *Chenopodiaceae* sp., *Cucurbitaceae* sp., *Papilionaceae* sp. (for instance peas), *Rosaceae* sp. (for instance strawberries); major crops such as *Graminae* sp. (for instance maize, lawn or cereals such as wheat, rice, barley and triticale), *Asteraceae* sp. (for instance sunflower), *Cruciferae* sp. (for instance colza), *Fabacae* sp. (for instance peanuts), *Papilionaceae* sp. (for instance soybean), *Solanaceae* sp. (for instance potatoes), *Chenopodiaceae* sp. (for instance beetroots); horticultural and forest crops; as well as genetically modified homologues of these crops.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, co suppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 1992/005251, WO 1995/009910, WO 1998/27806, WO 2005/002324, WO 2006/021972 and U.S. Pat. No. 6,229, 072). However, genetic determinants for male sterility can also be located in the nuclear genome. Male sterile plants can also be obtained by plant biotechnology methods such as genetic engineering. A particularly useful means of obtaining male-sterile plants is described in WO 1989/10396 in which, for example, a ribonuclease such as barnase is selectively expressed in the tapetum cells in the stamens. Fertility can then be restored by expression in the tapetum cells of a ribonuclease inhibitor such as barstar (e.g. WO 1991/002069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., Science (1983), 221, 370-371), the CP4 gene of the bacterium *Agrobacterium* sp. (Barry et al., Curr. Topics Plant Physiol. (1992), 7, 139-145), the genes encoding a Petunia EPSPS (Shah et al., Science (1986), 233, 478-481), a Tomato EPSPS (Gasser et al., J. Biol. Chem. (1988), 263, 4280-4289), or an *Eleusine* EPSPS (WO 2001/66704). It can also be a mutated EPSPS as described in for example EP-A 0837944, WO 2000/066746, WO 2000/066747 or WO 2002/026995. Glyphosate-tolerant plants can also be obtained by expressing a gene that encodes a glyphosate oxido-reductase enzyme as described in U.S. Pat. No. 5,776,760 and U.S. Pat. No. 5,463,175. Glyphosate-tolerant plants can also be obtained by expressing a gene that encodes a glyphosate acetyl transferase enzyme as described in for example WO 2002/036782, WO 2003/092360, WO 2005/

012515 and WO 2007/024782. Glyphosate-tolerant plants can also be obtained by selecting plants containing naturally-occurring mutations of the above-mentioned genes, as described in for example WO 2001/024615 or WO 2003/013226.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. No. 5,561,236; U.S. Pat. No. 5,648,477; U.S. Pat. No. 5,646,024; U.S. Pat. No. 5,273,894; U.S. Pat. No. 5,637,489; U.S. Pat. No. 5,276,268; U.S. Pat. No. 5,739,082; U.S. Pat. No. 5,908,810 and U.S. Pat. No. 7,112,665.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme as described in WO 1996/038567, WO 1999/024585 and WO 1999/024586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 1999/034008 and WO 2002/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright, Weed Science (2002), 50, 700-712, but also, in U.S. Pat. No. 5,605,011, U.S. Pat. No. 5,378,824, U.S. Pat. No. 5,141,870, and U.S. Pat. No. 5,013,659. The production of sulfonylurea-tolerant plants and imidazolinone-tolerant plants is described in U.S. Pat. No. 5,605,011; U.S. Pat. No. 5,013,659; U.S. Pat. No. 5,141,870; U.S. Pat. No. 5,767,361; U.S. Pat. No. 5,731,180; U.S. Pat. No. 5,304,732; U.S. Pat. No. 4,761,373; U.S. Pat. No. 5,331,107; U.S. Pat. No. 5,928,937; and U.S. Pat. No. 5,378,824; and international publication WO 1996/033270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 1997/41218, for sugar beet in U.S. Pat. No. 5,773,702 and WO 1999/057965, for lettuce in U.S. Pat. No. 5,198,599, or for sunflower in WO 2001/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance. An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al., Microbiology and Molecular Biology Reviews (1998), 62, 807-813, updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., Nat. Biotechnol, (2001), 19, 668-72; Schnepf et al., Applied Environm. Microbiol. (2006), 71, 1765-1774); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 1994/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants as described in WO 2000/004173 or WO2006/045633 or PCT/EP07/004,142.

b. plants which contain a stress tolerance enhancing transgene capable of reducing the expression and/or the activity of the PARG encoding genes of the plants or plants cells, as described e.g. in WO 2004/090140.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in WO2006/032469 or WO 2006/133827 or PCT/EP07/002,433.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications. Said transgenic plants synthesizing a modified starch are disclosed, for example, in EP 0571427, WO 1995/004826, EP 0719338, WO 1996/15248, WO 1996/19581, WO 1996/27674, WO 1997/11188, WO 1997/26362, WO 1997/32985, WO 1997/42328, WO 1997/44472, WO 1997/45545, WO 1998/27212, WO 1998/40503, WO99/58688, WO 1999/58690, WO 1999/58654, WO 2000/008184, WO 2000/008185, WO 2000/008175, WO 2000/28052, WO 2000/77229, WO 2001/12782, WO 2001/12826, WO 2002/101059, WO 2003/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 2000/22140, WO 2006/063862, WO 2006/072603, WO 2002/034923, EP 06090134.5, EP 06090228.5, EP 06090227.7, EP 07090007.1, EP 07090009.7, WO 2001/14569, WO 2002/79410, WO 2003/33540, WO 2004/078983, WO 2001/19975, WO 1995/26407, WO 1996/34968, WO 1998/20145, WO 1999/12950, WO 1999/66050, WO 1999/53072, U.S. Pat. No. 6,734,341, WO 2000/11192, WO 1998/22604, WO 1998/32326, WO 2001/98509, WO 2001/98509, WO 2005/002359, U.S. Pat. No. 5,824,790, U.S. Pat. No. 6,013,861, WO 1994/004693, WO 1994/009144, WO 1994/11520, WO 1995/35026, WO 1997/20936.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, as disclosed in EP 0663956, WO 1996/001904, WO 1996/021023, WO 1998/039460, and WO 1999/024593, plants producing alpha 1,4 glucans as disclosed in WO 1995/031553, US 2002/031826, U.S. Pat. No. 6,284,479, U.S. Pat. No. 5,712,107, WO 1997/047806, WO 1997/047807, WO 1997/047808 and WO 2000/014249, plants producing alpha-1,6 branched alpha-1,4-glucans, as disclosed in WO 2000/73422, plants producing alternan, as disclosed in WO 2000/047727, EP 06077301.7, U.S. Pat. No. 5,908,975 and EP 0728213, 3) transgenic plants which produce hyaluronan, as for example disclosed in WO 2006/032538, WO 2007/039314, WO 2007/039315, WO 2007/039316, JP 2006/304779, and WO 2005/012529.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 1998/000549 b) Plants, such as cotton plants, containing an altered form of rsw2 or rsw3 homologous nucleic acids as described in WO2004/053219 c) Plants, such as cotton plants, with increased expression of sucrose phosphate synthase as described in WO 2001/017333 d) Plants, such as cotton plants, with increased expression of sucrose synthase as described in WO02/45485 e) Plants, such as cotton plants, wherein the timing of the plasmodesmatal gating at the basis of the fiber cell is altered, e.g. through downregulation of fiberselective β1,3-glucanase as described in WO2005/017157 f) Plants, such as cotton plants, having fibers with altered reactivity, e.g. through the expression of N-acteylglucosaminetransferase gene including nodC and chitinsynthase genes as described in WO2006/136351

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content as described e.g. in U.S. Pat. No. 5,969,169, U.S. Pat. No. 5,840,946 or U.S. Pat. No. 6,323,392 or U.S. Pat. No. 6,063,947 b) Plants such as oilseed rape plants, producing oil having a low linolenic acid content as described in U.S. Pat. No. 6,270,828, U.S. Pat. No. 6,169,190 or U.S. Pat. No. 5,965,755 c) Plant such as oilseed rape plants, producing oil having a low level of saturated fatty acids as described e.g. in U.S. Pat. No. 5,434,283

Particularly useful transgenic plants which may be treated according to the invention are plants which comprise one or more genes which encode one or more toxins, such as the following which are sold under the trade names YIELD GARD® (for example maize, cotton, soya beans), Knock-Out® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoin-fo.jrc.it/gmp_browse.aspx and http://www.agbios.com/dbase.php).

The composition according to the invention can also be used against fungal diseases liable to to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, sprcaning, dipping, injection or any other suitable means.

Among the diseases of plants or crops that can be controlled by the method according to the invention, mention can be made of:

Powdery Mildew Diseases such as
Blumeria diseases caused for example by *Blumeria graminis*;
Podosphaera diseases caused for example by *Podosphaera leucotricha*;
Sphaerotheca diseases caused for example by *Sphaerotheca fuliginea*;
Uncinula diseases caused for example by *Uncinula necator*;
   Rust Diseases such as
Gymnosporangium diseases caused for example by *Gymnosporangium sabinae*;
Hemileia diseases caused for example by *Hemileia vastatrix*;
Phakopsora diseases caused for example by *Phakopsora pachyrhizi* and *Phakopsora meibomiae*;
Puccinia diseases caused for example by *Puccinia recondite*, *Puccinia graminis* or *Puccinia striiformis*;
Uromyces diseases caused for example by *Uromyces appendiculatus*;

Oomycete Diseases such as
Albugo diseases caused for example by *Albugo candida*;
Bremia diseases caused for example by *Bremia lactucae*;
Peronospora diseases caused for example by *Peronospora pisi* and *Peronospora brassicae*;
Phytophthora diseases caused for example by *Phytophthora infestans*;
Plasmopara diseases caused for example by *Plasmopara viticola*;
Pseudoperonospora diseases caused for example by *Pseudoperonospora humuli* and *Pseudoperonospora cubensis*;
Pythium diseases caused for example by *Pythium ultimum*;
   Leaf spot, Leaf blotch and Leaf Blight Diseases such as
Alternaria diseases caused for example by *Alternaria solani*;
Cercospora diseases caused for example by *Cercospora beticola*;
Cladiosporium diseases caused for example by *Cladiosporium cucumerinum*;
Cochliobolus diseases caused for example by *Cochliobolus sativus* (Conidiaform: *Drechslera*, Syn: *Helminthosporium*) or *Cochliobolus miyabeanus*;
Colletotrichum diseases caused for example by *Colletotrichum lindemuthianum*;
Cycloconium diseases caused for example by *Cycloconium oleaginum*;
Diaporthe diseases caused for example by *Diaporthe citri*;
Elsinoe diseases caused for example by *Elsinoe fawcettii*;
Gloeosporium diseases caused for example by *Gloeosporium laeticolor*;
Glomerella diseases caused for example by *Glomerella cingulata*;
Guignardia diseases caused for example by *Guignardia bidwellii*;
Leptosphaeria diseases caused for example by *Leptosphaeria maculans* and *Leptosphaeria nodorum*;
Magnaporthe diseases caused for example by *Magnaporthe grisea*;
Mycosphaerella diseases caused for example by *Mycosphaerella graminicola*, *Mycosphaerella arachidicola* and *Mycosphaerella fijiensis*;
Phaeosphaeria diseases caused for example by *Phaeosphaeria nodorum*;
Pyrenophora diseases caused for example by *Pyrenophora teres* or *Pyrenophora tritici repentis*;
Ramularia—diseases caused for example by *Ramularia collo-cygni* or *Ramularia areola*;
Rhynchosporium diseases caused for example by *Rhynchosporium secalis*;
Septoria diseases caused for example by *Septoria apii* and *Septoria lycopersici*;
Typhula diseases caused for example by *Thyphula incarnate*;
Venturia diseases caused for example by *Venturia inaequalis*;
   Root-, Sheath and Stem Diseases such as
Corticium diseases caused for example by *Corticium graminearum*;
Fusarium diseases caused for example by *Fusarium oxysporum*;
Gaeumannomyces diseases caused for example by *Gaeumannomyces graminis*;
Rhizoctonia diseases caused for example by *Rhizoctonia solani*;
Sarocladium diseases caused for example by *Sarocladium oryzae*;
Sclerotium diseases caused for example by *Sclerotium oryzae*;
Tapesia diseases caused for example by *Tapesia acuformis*;
Thielaviopsis diseases caused for example by *Thielaviopsis basicola*;

Ear and Panicle Diseases including Maize cob such as
Alternaria diseases caused for example by *Alternaria* spp.;
Aspergillus diseases caused for example by *Aspergillus flavus*;
Cladosporium diseases caused for example by *Cladosporium cladosporioides*;
Claviceps diseases caused for example by *Claviceps purpurea*;
Fusarium diseases caused for example by *Fusarium culmorum*;
Gibberella diseases caused for example by *Gibberella zeae*;
Monographella diseases caused for example by *Monographella nivalis*;
  Smut- and Bunt Diseases such as
Sphacelotheca diseases caused for example by *Sphacelotheca reiliana*;
Tilletia diseases caused for example by *Tilletia caries*;
Urocystis diseases caused for example by *Urocystis occulta*;
Ustilago diseases caused for example by *Ustilago nuda*;
  Fruit Rot and Mould Diseases such as
Aspergillus diseases caused for example by *Aspergillus flavus*;
Botrytis diseases caused for example by *Botrytis cinerea*;
Penicillium diseases caused for example by *Penicillium expansum* and *Penicillium purpurogenum*;
Rhizopus diseases caused by example by *Rhizopus stolonifer*
Sclerotinia diseases caused for example by *Sclerotinia sclerotiorum*;
Verticillium diseases caused for example by *Verticillium alboatrum*;
Seed- and Soilborne Decay, Mould, Wilt, Rot and Damping-off diseases
Alternaria diseases caused for example by *Alternaria brassicicola*;
Aphanomyces diseases caused for example by *Aphanomyces euteiches*;
Ascochyta diseases caused for example by *Ascochyta lentis*;
Aspergillus diseases caused for example by *Aspergillus flavus*;
Cladosporium diseases caused for example by *Cladosporium herbarum*;
Cochliobolus diseases caused for example by *Cochliobolus sativus*;
(Conidiaform: *Drechslera, Bipolaris* Syn: *Helminthosporium*);
Colletotrichum diseases caused for example by *Colletotrichum coccodes*;
Fusarium diseases caused for example by *Fusarium culmorum*;
Gibberella diseases caused for example by *Gibberella zeae*;
Macrophomina diseases caused for example by *Macrophomina phaseolina*;
Microdochium diseases caused for example by *Microdochium nivale*;
Monographella diseases caused for example by *Monographella nivalis*;
Penicillium diseases caused for example by *Penicillium expansum*;
Phoma diseases caused for example by *Phoma lingam*;
Phomopsis diseases caused for example by *Phomopsis sojae*;
Phytophthora diseases caused for example by *Phytophthora cactorum*;
Pyrenophora diseases caused for example by *Pyrenophora graminea*;
Pyricularia diseases caused for example by *Pyricularia oryzae*;
Pythium diseases caused for example by *Pythium ultimum*;
Rhizoctonia diseases caused for example by *Rhizoctonia solani*;
Rhizopus diseases caused for example by *Rhizopus oryzae*;
Sclerotium diseases caused for example by *Sclerotium rolfsii*;
Septoria diseases caused for example by *Septoria nodorum*;
Typhula diseases caused for example by *Typhula* incarnate;
Verticillium diseases caused for example by *Verticillium dahliae*;
  Canker, Broom and Dieback Diseases such as
Nectria diseases caused for example by *Nectria galligena*;
  Blight Diseases such as
Monilinia diseases caused for example by *Monilinia laxe*;
Leaf Blister or Leaf Curl Diseases including deformation of blooms and fruits such as *Exobasidium* diseases caused for example by *Exobasidium vexans*.
Taphrina diseases caused for example by *Taphrina deformans*;
  Decline Diseases of Wooden Plants such as
Esca disease caused for example by *Phaeomoniella clamydospora, Phaeoacremonium aleophilum* and *Fomitiporia mediterranea*;
Ganoderma diseases caused for example by *Ganoderma boninense*;
Rigidoporus diseases caused for example by *Rigidoporus lignosus*
  Diseases of Flowers and Seeds such as
Botrytis diseases caused for example by *Botrytis cinerea*;
Diseases of Tubers such as
Rhizoctonia diseases caused for example by *Rhizoctonia solani*;
Helminthosporium diseases caused for example by *Helminthosporium solani*;
  Club root diseases such as
Plasmodiophora diseases, cause for example by *Plamodiophora brassicae*.
  Diseases caused by Bacterial Organisms such as
Xanthomonas species for example *Xanthomonas campestris* pv. *oryzae*;
Pseudomonas species for example *Pseudomonas syringae* pv. *lachrymans*;
Erwinia species for example *Erwinia amylovora*.

The compounds according to the invention can also be used for the preparation of composition useful to curatively or preventively treat human or animal fungal diseases such as, for example, mycoses, dermatoses, *trichophyton* diseases and candidiases or diseases caused by *Aspergillus* spp., for example *Aspergillus fumigatus*.

The various aspects of the invention will now be illustrated with reference to the following table 1 of compound examples and the following preparation or efficacy examples.

The following table 1 illustrates in a non limiting manner examples of compounds according to the invention.

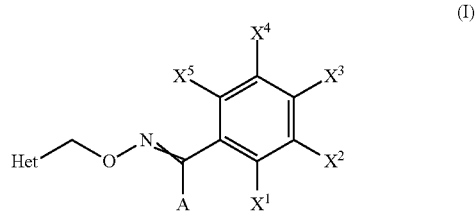

(I)

In table 1 we use the following abbreviations for specified claimed elements "Het" and "A" of the generic structure (I) of the invention:

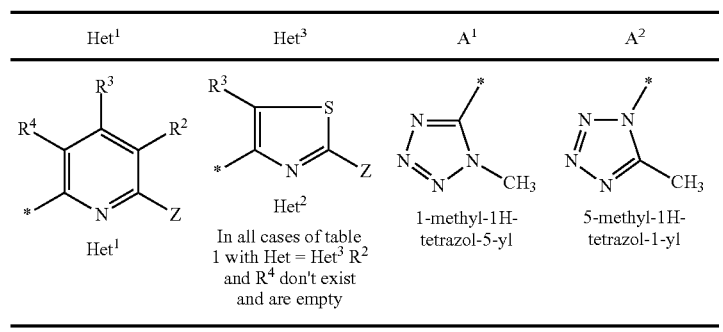

TABLE 1

| Ex. | Het | Z | R² | R³ | R⁴ | X¹ | X² | X³ | X⁴ | X⁵ | A | log p | MW measured |
|---|---|---|---|---|---|---|---|---|---|---|---|---|---|
| 1 | Het¹ | [(cyanoamino)methylidene]amino | H | H | H | H | H | H | H | H | A² | 2.22[b] | |
| 2 | Het¹ | {[methyl(octyl)amino]methylidene}amino | H | H | H | H | H | H | H | H | A² | | 463[m2] |
| 3 | Het¹ | {[ethyl(methyl)amino]methylidene}amino | H | H | H | H | H | H | H | H | A² | 1.43[b] | 379[m2] |
| 4 | Het¹ | [(3,4-dichlorobenzyl)carbamothioyl]amino | H | H | H | H | H | H | H | H | A² | 4.09[b] | 527[m2] |
| 5 | Het¹ | (phenylcarbamothioyl)amino | H | H | H | H | H | H | H | H | A² | 3.31[b] | 445[m2] |
| 6 | Het¹ | (octylcarbamothioyl)amino | H | H | H | H | H | H | H | H | A² | 4.97[b] | 481[m2] |
| 7 | Het¹ | [(2-phenylethyl)carbamothioyl]amino | H | H | H | H | H | H | H | H | A² | 3.67[b] | 473[m2] |
| 8 | Het¹ | (cyclohexylcarbamothioyl)amino | H | H | H | H | H | H | H | H | A² | 3.81[b] | 451[m2] |
| 9 | Het¹ | (cyclopentylcarbamothioyl)amino | H | H | H | H | H | H | H | H | A² | 3.53[b] | 437[m2] |
| 10 | Het¹ | (benzylcarbamothioyl)amino | H | H | H | H | H | H | H | H | A² | 3.52[b] | 459[m2] |
| 11 | Het¹ | (prop-2-en-1-ylcarbamothioyl)amino | H | H | H | H | H | H | H | H | A² | 3.09[b] | 409[m2] |
| 12 | Het¹ | (propan-2-ylcarbamothioyl)amino | H | H | H | H | H | H | H | H | A² | 3.22[b] | 411[m2] |
| 13 | Het¹ | (pentylcarbamothioyl)amino | H | H | H | H | H | H | H | H | A² | 3.82[b] | 439[m2] |
| 14 | Het¹ | methoxycarbonyl | H | H | H | H | H | H | H | H | A² | 2.47[b] | 353[m2] |
| 15 | Het¹ | COOH | H | H | H | H | H | H | H | H | A² | 1.97[b] | 339[m2] |
| 16 | Het¹ | pentylcarbamoyl | H | H | H | H | H | H | H | H | A² | 3.52[b] | 408[m2] |
| 17 | Het¹ | bromo | H | H | H | H | H | H | H | H | A¹ | 3.25[a]; 3.15[b] | 373[m1] |
| 18 | Het¹ | (trimethylsilyl)ethynyl | H | H | H | H | H | H | H | H | A¹ | | 391[m1] |
| 19 | Het¹ | ethynyl | H | H | H | H | H | H | H | H | A¹ | 2.69[a]; 2.7[b] | 318[m1] |
| 20 | Het¹ | hexyloxy | H | H | H | H | H | H | H | H | A¹ | 5.39[a] | 395[m1] |
| 21 | Het¹ | 6-[({[(E)-(1-methyl-1H-tetrazol-5-yl)(phenyl)methylidene]amino}oxy)methyl]pyridin-2-yl | H | H | H | H | H | H | H | H | A¹ | 4.36[a] | 587[m1] |
| 22 | Het¹ | 3,3-dimethylbut-1-yn-1-yl | H | H | H | H | H | H | H | H | A¹ | 4.19[a] | 375[m1] |
| 23 | Het¹ | hex-1-yn-1-yl | H | H | H | H | H | H | H | H | A¹ | 4.26[a] | 375[m1] |
| 24 | Het¹ | 3-methoxyprop-1-yn-1-yl | H | H | H | H | H | H | H | H | A¹ | 3.04[c] | 363[m1] |
| 25 | Het¹ | phenylethynyl | H | H | H | H | H | H | H | H | A¹ | 4.04[a] | 395[m1] |
| 26 | Het¹ | 3-(trimethylsilyl)prop-1-yn-1-yl | H | H | H | H | H | H | H | H | A¹ | 4.61[a] | 405[m1] |
| 27 | Het¹ | pent-1-yn-1-yl | H | H | H | H | H | H | H | H | A¹ | 3.83[a] | 361[m1] |
| 28 | Het¹ | (tripropan-2-ylsilyl)ethynyl | H | H | H | H | H | H | H | H | A¹ | 6.83[a] | 475[m1] |
| 29 | Het¹ | cyclopentylethynyl | H | H | H | H | H | H | H | H | A¹ | 4.34[a] | 387[m1] |
| 30 | Het¹ | cyclohexylethynyl | H | H | H | H | H | H | H | H | A¹ | 4.77[a] | 401[m1] |
| 31 | Het¹ | phenyl | H | H | H | H | H | H | H | H | A¹ | 3.89[a] | 371[m1] |
| 32 | Het³ | bromo | | H | | | H | H | H | H | A¹ | 3.09[a] | 381[m1] |
| 33 | Het¹ | 3-methoxyphenyl | H | H | H | H | H | H | H | H | A¹ | 3.89[a] | 401[m1] |
| 34 | Het¹ | 4-(trifluoromethyl)phenyl | H | H | H | H | H | H | H | H | A¹ | 4.62[a] | 439[m1] |
| 35 | Het¹ | biphenyl-4-yl | H | H | H | H | H | H | H | H | A¹ | 5.05[a] | 447[m1] |
| 36 | Het¹ | 4-(benzyloxy)phenyl | H | H | H | H | H | H | H | H | A¹ | 4.89[a] | 477[m1] |
| 37 | Het³ | methyl(2-phenylethyl)amino | | H | | | H | H | H | H | A¹ | 3.96[a] | 434[m1] |
| 38 | Het¹ | 4-ethylphenyl | H | H | H | H | H | H | H | H | A¹ | 4.7[a] | 399[m1] |
| 39 | Het¹ | 4-butoxyphenyl | H | H | H | H | H | H | H | H | A¹ | 5.2[a] | 443[m1] |
| 40 | Het¹ | 4-(trifluoromethoxy)phenyl | H | H | H | H | H | H | H | H | A¹ | 4.73[a] | 455[m1] |
| 41 | Het¹ | 3,5-dichlorophenyl | H | H | H | H | H | H | H | H | A¹ | 5.23[a] | 439[m1] |
| 42 | Het¹ | CH₃ | H | H | H | H | H | H | H | H | A¹ | 1.67[b] | 309[m4] |
| 43 | Het¹ | H | CF₃ | H | Cl | H | H | H | H | H | A¹ | 3.76[b] | 397[m4] |
| 44 | Het¹ | 3-butoxyphenyl | H | H | H | H | H | H | H | H | A¹ | 5.2[a] | 443[m1] |
| 45 | Het¹ | 3-(trifluoromethyl)phenyl | H | H | H | H | H | H | H | H | A¹ | 4.56[a] | 439[m1] |
| 46 | Het³ | (3-methoxypropyl)(methyl)amino | | H | | | H | H | H | H | A¹ | 2.59[a] | 402[m1] |
| 47 | Het¹ | 3-chlorophenyl | H | H | H | H | H | H | H | H | A¹ | 4.49[a] | 405[m1] |
| 48 | Het³ | benzyl(methyl)amino | | H | | | H | H | H | H | A¹ | 3.89[a] | 420[m1] |
| 49 | Het³ | piperidin-1-yl | | H | | | H | H | H | H | A¹ | 3.39[a] | 384[m1] |
| 50 | Het³ | hexyl(methyl)amino | | H | | | H | H | H | H | A¹ | 4.56[a] | 414[m1] |
| 51 | Het³ | methyl(pentyl)amino | | H | | | H | H | H | H | A¹ | 4.01[a] | 400[m1] |
| 52 | Het¹ | aminomethyl | H | H | H | H | H | H | H | H | A¹ | 1.23[b] | 324[m3] |
| 53 | Het¹ | (hexanoylamino)methyl | H | H | H | H | H | H | H | H | A¹ | 2.88[b] | 422[m3] |
| 54 | Het¹ | [(phenylacetyl)amino]methyl | H | H | H | H | H | H | H | H | A¹ | 2.7[b] | 442[m3] |

TABLE 1-continued

| Ex. | Het | Z | R² | R³ | R⁴ | X¹ | X² | X³ | X⁴ | X⁵ | A | log p | MW measured |
|---|---|---|---|---|---|---|---|---|---|---|---|---|---|
| 55 | Het¹ | [(2,2-dimethylpropanoyl)amino]methyl | H | H | H | H | H | H | H | H | A¹ | 2.58[b] | 408[m3] |
| 56 | Het¹ | [(3-methylbutanoyl)amino]methyl | H | H | H | H | H | H | H | H | A¹ | 2.51[b] | 408[m3] |
| 57 | Het¹ | (pentanoylamino)methyl | H | H | H | H | H | H | H | H | A¹ | 2.56[b] | 408[m3] |
| 58 | Het¹ | [(3-phenylpropanoyl)amino]methyl | H | H | H | H | H | H | H | H | A¹ | 2.82[b] | 456[m3] |
| 59 | Het³ | phenylethynyl | | | | H | H | H | H | H | A¹ | 4.16[a] | 401[m1] |
| 60 | Het¹ | {[(pentyloxy)carbonyl]amino}methyl | H | | H | H | H | H | H | H | A¹ | 3.48[b] | 438[m3] |
| 61 | Het³ | 4-methylpent-1-yn-1-yl | | | | H | H | H | H | H | A¹ | 4.34[a] | 381[m1] |
| 62 | Het³ | 5-phenylpent-1-yn-1-yl | | | | H | H | H | H | H | A¹ | 4.78[a] | 443[m1] |
| 63 | Het¹ | [(butoxycarbonyl)amino]methyl | H | | H | H | H | H | H | H | A¹ | 3.19[b] | 424[m3] |
| 64 | Het³ | 3-methylhex-1-yn-1-yl | | | | H | H | H | H | H | A¹ | 4.78[a] | |
| 65 | Het³ | 5-methylhex-1-yn-1-yl | | | | H | H | H | H | H | A¹ | 4.75[a] | 395[m1] |
| 66 | Het³ | 3-cyclopentylprop-1-yn-1-yl | | | | H | H | H | H | H | A¹ | 4.92[a] | 407[m1] |
| 67 | Het³ | 3-cyclohexylprop-1-yn-1-yl | | | | H | H | H | H | H | A¹ | 5.32[a] | 421[m1] |
| 68 | Het³ | cyclohexylethynyl | | | | H | H | H | H | H | A¹ | 4.89[a] | 407[m1] |
| 69 | Het³ | cyclopentylethynyl | | | | H | H | H | H | H | A¹ | 4.49[a] | 393[m1] |
| 70 | Het³ | cyclopropylethynyl | | | | H | H | H | H | H | A¹ | 3.58[a] | 365[m1] |
| 71 | Het³ | 3-methoxyprop-1-yn-1-yl | | | | H | H | H | H | H | A¹ | 2.92[a] | 369[m1] |
| 72 | Het³ | hex-1-yn-1-yl | | | | H | H | H | H | H | A¹ | 4.36[a] | 381[m1] |
| 73 | Het¹ | pentadecafluoroheptyl | H | H | H | H | H | H | H | H | A¹ | 5.86[a] | 663[m1] |
| 74 | Het¹ | pentylsulfanyl | H | H | H | H | H | H | H | H | A¹ | 5.14[a] | 397[m1] |
| 75 | Het¹ | (3-methylbutan-2-yl)carbamoyl | H | H | H | H | H | H | H | H | A¹ | 3.44[b] | 408[m4] |
| 76 | Het¹ | acetyl(2-cyclohexylethyl)amino | H | H | H | H | H | H | H | H | A¹ | 4.16[b] | 462[m1] |
| 77 | Het¹ | dimethylcarbamoyl | H | H | H | H | H | H | H | H | A¹ | 2.04[b] | |
| 78 | Het³ | propan-2-yl | | | | H | H | H | H | H | A¹ | 3.39[b] | |
| 79 | Het¹ | fluoro | H | | | H | H | H | H | H | A¹ | 2.77[b] | |
| 80 | Het¹ | (2-cyclohexylethyl)amino | H | | H | H | H | H | H | H | A¹ | 3.35[a] | |
| 81 | Het³ | (1E)-hept-1-en-1-yl | | | | H | | H | H | H | A¹ | 5.05[a] | 397[m1] |
| 82 | Het³ | (1E)-oct-1-en-1-yl | | | | H | | H | H | H | A¹ | 5.53[a] | 411[m1] |
| 83 | Het¹ | [(2S)-1-methoxypropan-2-yl]carbamoyl | H | H | H | H | H | H | H | H | A¹ | 2.7[b] | |
| 84 | Het¹ | propan-2-ylcarbamoyl | H | H | H | H | H | H | H | H | A¹ | 2.84[b] | |
| 85 | Het¹ | methyl(pentyl)carbamoyl | H | H | H | H | H | H | H | H | A¹ | 3.29[b] | |
| 86 | Het¹ | tert-butylcarbamoyl | H | H | H | H | H | H | H | H | A¹ | 3.37[b] | |
| 87 | Het¹ | (E)-2-(3-methoxyphenyl)ethenyl | H | H | H | H | H | H | H | H | A¹ | 4.14[a] | |
| 88 | Het³ | (1E)-3-phenylprop-1-en-1-yl | | | | H | H | H | H | H | A¹ | 4.29[a] | 417[m1] |
| 89 | Het³ | (E)-2-cyclohexylethenyl | | | | H | H | H | H | H | A¹ | 5.14[a] | |
| 90 | Het¹ | (1E)-hept-1-en-1-yl | H | H | H | H | H | H | H | H | A¹ | 5[a] | |
| 91 | Het¹ | (E)-2-(3-fluorophenyl)ethenyl | H | H | H | H | H | H | H | H | A¹ | 4.29[a] | |
| 92 | Het¹ | (1E)-oct-1-en-1-yl | H | H | H | H | H | H | H | H | A¹ | 5.5[a] | |
| 93 | Het¹ | (E)-2-cyclohexylethenyl | H | H | H | H | H | H | H | H | A¹ | 5.05[a] | |
| 94 | Het¹ | (1E)-3-phenylprop-1-en-1-yl | H | H | H | H | H | H | H | H | A¹ | 4.31[a] | |
| 95 | Het¹ | (E)-2-(3,5-difluorophenyl)ethenyl | H | H | H | H | H | H | H | H | A¹ | 4.49[a] | |
| 96 | Het¹ | bromo | H | H | H | F | H | H | H | H | A¹ | 3.27[b] | |
| 97 | Het¹ | 3-cyclohexylprop-1-yn-1-yl | H | H | H | F | H | H | H | H | A¹ | 5.28[b] | |
| 98 | Het¹ | 3-cyclopentylprop-1-yn-1-yl | H | H | H | F | H | H | H | H | A¹ | 4.92[b] | |
| 99 | Het¹ | hex-1-yn-1-yl | H | H | H | F | H | H | H | H | A¹ | 4.41[b] | |
| 100 | Het¹ | 3-phenylprop-1-yn-1-yl | H | H | H | F | H | H | H | H | A¹ | 4.24[b] | |
| 101 | Het¹ | 5-methylhex-1-yn-1-yl | H | H | H | F | H | H | H | H | A¹ | 3.13[b] | |
| 102 | Het¹ | 3-(ethylsulfanyl)prop-1-yn-1-yl | H | H | H | F | H | H | H | H | A¹ | 3.85[b] | |
| 103 | Het¹ | 5-cyanopent-1-yn-1-yl | H | H | H | F | H | H | H | H | A¹ | 3.11[b] | |
| 104 | Het¹ | 5-phenylpent-1-yn-1-yl | H | H | H | F | H | H | H | H | A¹ | 4.84[b] | |
| 105 | Het¹ | 5-chloropent-1-yn-1-yl | H | H | H | F | H | H | H | H | A¹ | 3.87[b] | |
| 106 | Het¹ | 3-phenoxyprop-1-yn-1-yl | H | H | H | F | H | H | H | H | A¹ | 4.04[b] | |
| 107 | Het¹ | 4-cyclohexylbut-1-yn-1-yl | H | H | H | F | H | H | H | H | A¹ | 5.68[b] | |
| 108 | Het¹ | cyclohexylethynyl | H | H | H | F | H | H | H | H | A¹ | 4.92[b] | |
| 109 | Het¹ | cyclopropylethynyl | H | H | H | H | H | H | H | H | A¹ | 3.46[b] | |
| 110 | Het¹ | 3-[3-(trifluoromethyl)-1H-pyrazol-1-yl]prop-1-yn-1-yl | H | H | H | H | H | H | H | H | A¹ | 3.62[b] | |
| 111 | Het¹ | 3-cyclobutylprop-1-yn-1-yl | H | H | H | H | H | H | H | H | A¹ | 4.39[b] | |
| 112 | Het¹ | 3-(3-fluorophenyl)prop-1-yn-1-yl | H | H | H | H | H | H | H | H | A¹ | 4.16[b] | |
| 113 | Het³ | chloro | | Cl | | H | H | H | H | H | A¹ | 3.67[b] | |
| 114 | Het³ | cyclopropylethynyl | | Cl | | H | H | H | H | H | A¹ | 4.59[b] | |
| 115 | Het³ | pent-1-yn-1-yl | | Cl | | H | H | H | H | H | A¹ | 4.75[b] | |
| 116 | Het³ | cyclopentylethynyl | | Cl | | H | H | H | H | H | A¹ | 5.31[b] | |
| 117 | Het³ | hex-1-yn-1-yl | | Cl | | H | H | H | H | H | A¹ | 5.22[b] | |
| 118 | Het³ | 5-methylhex-1-yn-1-yl | | Cl | | H | H | H | H | H | A¹ | 5.59[b] | |
| 119 | Het³ | 3-phenoxyprop-1-yn-1-yl | | Cl | | H | H | H | H | H | A¹ | 4.62[b] | 465[m1] |
| 120 | Het³ | cyclohexylethynyl | | Cl | | H | H | H | H | H | A¹ | 5.75[b] | |
| 121 | Het³ | 5-chloropent-1-yn-1-yl | | Cl | | H | H | H | H | H | A¹ | 4.51[b] | |
| 122 | Het³ | 5-cyanopent-1-yn-1-yl | | Cl | | H | H | H | H | H | A¹ | 3.58[b] | |
| 123 | Het³ | 5-phenylpent-1-yn-1-yl | | Cl | | H | H | H | H | H | A¹ | 5.56[b] | |
| 124 | Het¹ | cyclohex-1-en-1-ylethynyl | H | H | H | H | H | H | H | H | A¹ | 4.34[b] | |
| 125 | Het¹ | bromo | methoxy | H | H | H | H | H | H | H | A¹ | 3.13[b] | |
| 126 | Het¹ | cyclopropylethynyl | methoxy | H | H | H | H | H | H | H | A¹ | 3.23[b] | |
| 127 | Het¹ | hex-1-yn-1-yl | methoxy | H | H | H | H | H | H | H | A¹ | 3.96[b] | |
| 128 | Het¹ | 3-cyclopentylprop-1-yn-1-yl | methoxy | H | H | H | H | H | H | H | A¹ | 4.46[b] | |
| 129 | Het¹ | 3-cyclohexylprop-1-yn-1-yl | methoxy | H | H | H | H | H | H | H | A¹ | 4.84[b] | |
| 130 | Het¹ | 5-phenylpent-1-yn-1-yl | methoxy | H | H | H | H | H | H | H | A¹ | 4.44[b] | |

TABLE 1-continued

| Ex. | Het | Z | R² | R³ | R⁴ | X¹ | X² | X³ | X⁴ | X⁵ | A | log p | MW measured |
|---|---|---|---|---|---|---|---|---|---|---|---|---|---|
| 131 | Het¹ | 3-phenoxyprop-1-yn-1-yl | methoxy | H | H | H | H | H | H | H | A¹ | 3.8[b] | |
| 132 | Het¹ | cyclohexylethynyl | methoxy | H | H | H | H | H | H | H | A¹ | 4.44[b] | |
| 133 | Het¹ | 3,3-dimethylbut-1-yn-1-yl | methoxy | H | H | H | H | H | H | H | A¹ | 3.92[b] | |
| 134 | Het¹ | (4-ethylphenyl)ethynyl | methoxy | H | H | H | H | H | H | H | A¹ | 4.56[b] | |
| 135 | Het¹ | 5-cyanopent-1-yn-1-yl | methoxy | H | H | H | H | H | H | H | A¹ | 2.82[b] | |
| 136 | Het³ | (3E)-4-methoxybut-3-en-1-yn-1-yl | | | H | H | H | H | H | H | A¹ | 3.06[a] | |
| 137 | Het³ | 5-(acetyloxy)pent-1-yn-1-yl | | | H | H | H | H | H | H | A¹ | 3.17[a] | |
| 138 | Het³ | (trimethylsilyl)ethynyl | | | H | H | H | H | H | H | A¹ | 4.59[a] | |
| 139 | Het³ | ethynyl | | | H | H | H | H | H | H | A¹ | 2.77[a] | |
| 140 | Het¹ | (tert-butoxycarbonyl)[2-(2,2,3,3-tetrafluorocyclobutyl)ethyl]amino | H | H | H | H | H | H | H | H | A¹ | 5.05[a] | |
| 141 | Het¹ | (tert-butoxycarbonyl)(2-cyclohexylethyl)amino | H | H | H | H | H | H | H | H | A¹ | 6.56[a] | |
| 142 | Het¹ | (tert-butoxycarbonyl)(cyclopropylmethyl)amino | H | H | H | H | H | H | H | H | A¹ | 4.7[a] | |
| 143 | Het¹ | [2-(2,2,3,3-tetrafluorocyclobutyl)ethyl]amino | H | H | H | H | H | H | H | H | A¹ | 2.51[a] | |
| 144 | Het¹ | (cyclopropylmethyl)amino | H | H | H | H | H | H | H | H | A¹ | 1.75[a] | |
| 145 | Het³ | bromo | | | H | H | H | H | H | H | A² | 3.15[b] | |
| 146 | Het³ | bromo | | | H | H | F | H | H | H | A¹ | 3.23[b] | |
| 147 | Het³ | 3-cyclohexylprop-1-yn-1-yl | | | H | H | F | H | H | H | A¹ | 5.42[b] | |
| 148 | Het³ | cyclopropylethynyl | | | H | H | F | H | H | H | A¹ | 3.71[b] | |
| 149 | Het³ | hex-1-yn-1-yl | | | H | H | F | H | H | H | A¹ | 4.51[b] | |
| 150 | Het³ | 5-phenylpent-1-yn-1-yl | | | H | H | F | H | H | H | A¹ | 4.89[b] | |
| 151 | Het³ | pent-1-yn-1-yl | | | H | H | F | H | H | H | A¹ | 4.09[b] | |
| 152 | Het³ | hept-1-yn-1-yl | | | H | H | F | H | H | H | A¹ | 4.94[b] | |
| 153 | Het³ | 3-cyclopentylprop-1-yn-1-yl | | | H | H | F | H | H | H | A¹ | 5.03[b] | |
| 154 | Het³ | 5-cyanopent-1-yn-1-yl | | | H | H | F | H | H | H | A¹ | 3.09[b] | |
| 155 | Het³ | 6-chlorohex-1-yn-1-yl | | | H | H | F | H | H | H | A¹ | 4.19[b] | |
| 156 | Het³ | 4-phenylbut-1-yn-1-yl | | | H | H | F | H | H | H | A¹ | 4.49[b] | |
| 157 | Het³ | ethynyl | | | H | H | F | H | H | H | A¹ | 2.88[b] | |
| 158 | Het¹ | [(2E)-6,6-dimethylhept-2-en-4-yn-1-yl]amino | H | | H | H | H | H | H | H | A¹ | 3.25[a] | |
| 159 | Het¹ | cyclopropylethynyl | | | H | H | H | H | H | H | A² | 3.65[b] | |
| 160 | Het¹ | 1,3-dioxolan-2-yl | H | | H | H | H | H | H | H | A¹ | 2.47[c] | |
| 161 | Het³ | (2-cyclohexylethyl)amino | | | H | H | H | H | H | H | A¹ | 3.62[b] | |
| 162 | Het³ | (cyclopropylmethyl)amino | | | H | H | H | H | H | H | A¹ | 2.26[b] | |
| 163 | Het³ | 6-chlorohex-1-yn-1-yl | | | H | H | H | H | H | H | A² | 4.16[b] | |
| 164 | Het³ | hex-1-yn-1-yl | | | H | H | H | H | H | H | A² | 4.49[b] | |
| 165 | Het³ | pent-1-yn-1-yl | | | H | H | H | H | H | H | A² | 4.04[b] | |
| 166 | Het³ | 5-phenylpent-1-yn-1-yl | | | H | H | H | H | H | H | A² | 4.84[b] | |
| 167 | Het³ | hept-1-yn-1-yl | | | H | H | H | H | H | H | A² | 4.92[b] | |
| 168 | Het³ | 4-phenylbut-1-yn-1-yl | | | H | H | H | H | H | H | A² | 4.44[b] | |
| 169 | Het³ | 3-cyclohexylprop-1-yn-1-yl | | | H | H | H | H | H | H | A² | 5.41[b] | |
| 170 | Het³ | 3-cyclopentylprop-1-yn-1-yl | | | H | H | H | H | H | H | A² | 4.97[b] | |
| 171 | Het³ | 5-cyanopent-1-yn-1-yl | | | H | H | H | H | H | H | A² | 3.02[b] | |
| 172 | Het¹ | 4-butyl-1,3-dioxolan-2-yl | H | | H | H | H | H | H | H | A¹ | 4.34[c] | |
| 173 | Het¹ | 4-[(benzyloxy)methyl]-1,3-dioxolan-2-yl | H | | H | H | H | H | H | H | A¹ | 3.89[c] | |
| 174 | Het¹ | formyl | H | | H | H | H | H | H | H | A¹ | 2.54[a] | |
| 175 | Het³ | bromo | | CH₃ | H | H | H | H | H | H | A¹ | 3.37[b] | |
| 176 | Het¹ | 1-hydroxy-3-phenylpropyl | H | | H | H | H | H | H | H | A¹ | 3.35[a] | |
| 177 | Het¹ | (hydroxyimino)methyl | H | | H | H | H | H | H | H | A¹ | 2.16[a] | |
| 178 | Het¹ | (cyclobutylmethyl)amino | H | | H | H | H | H | H | H | A¹ | 1.98[a] | |
| 179 | Het¹ | [(2,2-difluorocyclopropyl)methyl]amino | H | | H | H | H | H | H | H | A¹ | 2.17[a] | |
| 180 | Het¹ | (4-cyclohexylbutyl)amino | H | | H | H | H | H | H | H | A¹ | 3.55[a] | |
| 181 | Het³ | cyclopropylethynyl | | CH₃ | H | H | H | H | H | H | A¹ | 3.83[b] | |
| 182 | Het³ | pent-1-yn-1-yl | | CH₃ | H | H | H | H | H | H | A¹ | 4.24[b] | |
| 183 | Het³ | hex-1-yn-1-yl | | CH₃ | H | H | H | H | H | H | A¹ | 3.37[b] | |
| 184 | Het³ | 3-cyclohexylprop-1-yn-1-yl | | CH₃ | H | H | H | H | H | H | A¹ | 5.62[b] | |
| 185 | Het³ | 3-cyclopentylprop-1-yn-1-yl | | CH₃ | H | H | H | H | H | H | A¹ | 5.2[b] | |
| 186 | Het³ | 5-phenylpent-1-yn-1-yl | | CH₃ | H | H | H | H | H | H | A¹ | 5.05[b] | |
| 187 | Het³ | 4-phenylbut-1-yn-1-yl | | CH₃ | H | H | H | H | H | H | A¹ | 4.65[b] | |
| 188 | Het³ | 3-methylhex-1-yn-1-yl | | CH₃ | H | H | H | H | H | H | A¹ | 5.06[b] | |
| 189 | Het³ | 3-methylbut-1-yn-1-yl | | CH₃ | H | H | H | H | H | H | A¹ | 4.21[b] | |
| 190 | Het³ | cyclopentylethynyl | | CH₃ | H | H | H | H | H | H | A¹ | 4.75[b] | |
| 191 | Het³ | (4-cyanophenyl)ethynyl | | | H | H | H | H | H | H | A¹ | 3.76[b] | |
| 192 | Het³ | (4-methoxyphenyl)ethynyl | | | H | H | H | H | H | H | A¹ | 4.14[b] | |
| 193 | Het³ | 5-chloropent-1-yn-1-yl | | | H | H | H | H | H | H | A¹ | 3.8[b] | |
| 194 | Het³ | naphthalen-2-ylethynyl | | | H | H | H | H | H | H | A¹ | 4.92[b] | |
| 195 | Het³ | 6-methoxy-6-oxohex-1-yn-1-yl | | | H | H | H | H | H | H | A¹ | 3.33[b] | |
| 196 | Het³ | 3-methoxy-3-methylbut-1-yn-1-yl | | | H | H | H | H | H | H | A¹ | 3.53[b] | |
| 197 | Het¹ | [2-(2-ethoxyethoxy)ethyl]amino | H | | H | H | H | H | H | H | A¹ | 1.7[a] | |
| 198 | Het³ | 4-hydroxybut-1-yn-1-yl | | | H | H | H | H | H | H | A¹ | 2.3[b] | |
| 199 | Het³ | 3-(ethylsulfanyl)prop-1-yn-1-yl | | | H | H | H | H | H | H | A¹ | 3.78[b] | |
| 200 | Het¹ | (3-cyclohexylpropyl)amino | H | | H | H | H | H | H | H | A¹ | 3.17[a] | |
| 201 | Het¹ | [(cyclohex-3-en-1-ylmethylidene)hydrazinylidene]methyl | H | | H | H | H | H | H | H | A¹ | 4.16[a] | |

TABLE 1-continued

| Ex. | Het | Z | R² | R³ | R⁴ | X¹ | X² | X³ | X⁴ | X⁵ | A | log p | MW measured |
|---|---|---|---|---|---|---|---|---|---|---|---|---|---|
| 202 | Het³ | (4-butylphenyl)ethynyl | | H | | H | H | H | H | H | A¹ | 5.82[b] | |
| 203 | Het¹ | [2-(cyclohexyloxy)ethyl]amino | H | H | H | H | H | H | H | H | A¹ | 2.35[b] | |
| 204 | Het¹ | [2-(cyclopentyloxy)ethyl]amino | H | H | H | H | H | H | H | H | A¹ | 2.14[b] | |
| 205 | Het¹ | [(2,2-dichlorocyclopropyl)methyl]amino | H | H | H | H | H | H | H | H | A¹ | 2.75[b] | |
| 206 | Het¹ | thiophen-2-ylethynyl | H | H | H | H | H | H | H | H | A¹ | 3.94[b] | |
| 207 | Het¹ | thiophen-3-ylethynyl | H | H | H | H | H | H | H | H | A¹ | 3.83[b] | |
| 208 | Het¹ | naphthalen-2-ylethynyl | H | H | H | H | H | H | H | H | A¹ | 4.78[b] | |
| 209 | Het¹ | 4-cyanobut-1-yn-1-yl | H | H | H | H | H | H | H | H | A¹ | 2.7[b] | |
| 210 | Het¹ | 4-phenylbut-1-yn-1-yl | H | H | H | H | H | H | H | H | A¹ | 4.29[b] | |
| 211 | Het¹ | 6-chlorohex-1-yn-1-yl | H | H | H | H | H | H | H | H | A¹ | 3.99[b] | |
| 212 | Het¹ | 5-chloropent-1-yn-1-yl | H | H | H | H | H | H | H | H | A¹ | 3.71[b] | |
| 213 | Het¹ | 3-cyclohexylprop-1-yn-1-yl | H | H | H | H | H | H | H | H | A¹ | 5.17[b] | |
| 214 | Het¹ | hept-1-yn-1-yl | H | H | H | H | H | H | H | H | A¹ | 4.67[b] | |
| 215 | Het¹ | (2-chlorophenyl)ethynyl | H | H | H | H | H | H | H | H | A¹ | 4.36[b] | |
| 216 | Het¹ | biphenyl-4-ylethynyl | H | H | H | H | H | H | H | H | A¹ | 5.11[b] | |
| 217 | Het¹ | [4-(trifluoromethyl)phenyl]ethynyl | H | H | H | H | H | H | H | H | A¹ | 4.65[b] | |
| 218 | Het¹ | [3-(trifluoromethyl)phenyl]ethynyl | H | H | H | H | H | H | H | H | A¹ | 4.62[b] | |
| 219 | Het¹ | [2-(trifluoromethyl)phenyl]ethynyl | H | H | H | H | H | H | H | H | A¹ | 4.44[b] | |
| 220 | Het¹ | [4-(trifluoromethoxy)phenyl]ethynyl | H | H | H | H | H | H | H | H | A¹ | 4.75[b] | |
| 221 | Het¹ | (3-methoxyphenyl)ethynyl | H | H | H | H | H | H | H | H | A¹ | 4.09[b] | |
| 222 | Het¹ | (2-methoxyphenyl)ethynyl | H | H | H | H | H | H | H | H | A¹ | 3.89[b] | |
| 223 | Het¹ | (4-fluorophenyl)ethynyl | H | H | H | H | H | H | H | H | A¹ | 4.11[b] | |
| 224 | Het¹ | (4-cyanophenyl)ethynyl | H | H | H | H | H | H | H | H | A¹ | 3.69[b] | |
| 225 | Het¹ | (3-cyanophenyl)ethynyl | H | H | H | H | H | H | H | H | A¹ | 3.69[b] | |
| 226 | Het¹ | (4-butoxyphenyl)ethynyl | H | H | H | H | H | H | H | H | A¹ | 5.29[b] | |
| 227 | Het¹ | (4-ethoxyphenyl)ethynyl | H | H | H | H | H | H | H | H | A¹ | 4.41[b] | |
| 228 | Het¹ | (4-methoxyphenyl)ethynyl | H | H | H | H | H | H | H | H | A¹ | 4.01[b] | |
| 229 | Het¹ | [4-(propan-2-yl)phenyl]ethynyl | H | H | H | H | H | H | H | H | A¹ | 5.14[b] | |
| 230 | Het¹ | (4-ethylphenyl)ethynyl | H | H | H | H | H | H | H | H | A¹ | 4.81[b] | |
| 231 | Het¹ | (4-methylphenyl)ethynyl | H | H | H | H | H | H | H | H | A¹ | 4.44[b] | |
| 232 | Het¹ | [4-(piperidin-1-yl)phenyl]ethynyl | H | H | H | H | H | H | H | H | A¹ | 4.81[b] | |
| 233 | Het¹ | (3,5-difluorophenyl)ethynyl | H | H | H | H | H | H | H | H | A¹ | 4.31[b] | |
| 234 | Het¹ | (4-phenoxyphenyl)ethynyl | H | H | H | H | H | H | H | H | A¹ | 5.08[b] | |
| 235 | Het¹ | oct-1-yn-1-yl | H | H | H | H | H | H | H | H | A¹ | 5.11[b] | |
| 236 | Het¹ | 3-cyclopentylprop-1-yn-1-yl | H | H | H | H | H | H | H | H | A¹ | 4.78[b] | |
| 237 | Het¹ | 4-cyclohexylbut-1-yn-1-yl | H | H | H | H | H | H | H | H | A¹ | 5.62[b] | |
| 238 | Het¹ | 3-phenylprop-1-yn-1-yl | H | H | H | H | H | H | H | H | A¹ | 4.09[b] | |
| 239 | Het¹ | 5-cyanopent-1-yn-1-yl | H | H | H | H | H | H | H | H | A¹ | 2.9[b] | |
| 240 | Het¹ | 3-methoxy-3-methylbut-1-yn-1-yl | H | H | H | H | H | H | H | H | A¹ | 3.42[b] | |
| 241 | Het¹ | 3-methyl-3-propoxybut-1-yn-1-yl | H | H | H | H | H | H | H | H | A¹ | 4.31[b] | |
| 242 | Het¹ | 3-(morpholin-4-yl)prop-1-yn-1-yl | H | H | H | H | H | H | H | H | A¹ | 1.44[b] | |
| 243 | Het¹ | 3-(ethylsulfanyl)prop-1-yn-1-yl | H | H | H | H | H | H | H | H | A¹ | 3.69[b] | |
| 244 | Het¹ | (4-propylphenyl)ethynyl | H | H | H | H | H | H | H | H | A¹ | 5.23[b] | |
| 245 | Het¹ | (4-tert-butylphenyl)ethynyl | H | H | H | H | H | H | H | H | A¹ | 5.44[b] | |
| 246 | Het¹ | (4-propoxyphenyl)ethynyl | H | H | H | H | H | H | H | H | A¹ | 4.86[b] | |
| 247 | Het¹ | (2-fluorophenyl)ethynyl | H | H | H | H | H | H | H | H | A¹ | 4.06[b] | |
| 248 | Het¹ | (3-fluorophenyl)ethynyl | H | H | H | H | H | H | H | H | A¹ | 4.16[b] | |
| 249 | Het¹ | [3-(trifluoromethoxy)phenyl]ethynyl | H | H | H | H | H | H | H | H | A¹ | 4.75[b] | |
| 250 | Het¹ | (4-chlorophenyl)ethynyl | H | H | H | H | H | H | H | H | A¹ | 4.54[b] | |
| 251 | Het¹ | [4-(dimethylamino)phenyl]ethynyl | H | H | H | H | H | H | H | H | A¹ | 4.29[b] | |
| 252 | Het¹ | 6-hydroxyhex-1-yn-1-yl | H | H | H | H | H | H | H | H | A¹ | 2.58[b] | |
| 253 | Het¹ | 4-hydroxybut-1-yn-1-yl | H | H | H | H | H | H | H | H | A¹ | 2.23[b] | |
| 254 | Het¹ | 3-(propanoyloxy)prop-1-yn-1-yl | H | H | H | H | H | H | H | H | A¹ | 3.29[b] | |
| 255 | Het¹ | 3-(benzyloxy)prop-1-yn-1-yl | H | H | H | H | H | H | H | H | A¹ | 3.96[b] | |
| 256 | Het³ | (4-propoxyphenyl)ethynyl | | H | | H | H | H | H | H | A¹ | 5.03[b] | |
| 257 | Het³ | [4-(propan-2-yl)phenyl]ethynyl | | H | | H | H | H | H | H | A¹ | 5.29[b] | |
| 258 | Het³ | (4-butoxyphenyl)ethynyl | | H | | H | H | H | H | H | A¹ | 5.44[b] | |
| 259 | Het³ | (3-cyanophenyl)ethynyl | | H | | H | H | H | H | H | A¹ | 3.76[b] | |
| 260 | Het³ | (2-fluorophenyl)ethynyl | | H | | H | H | H | H | H | A¹ | 4.15[b] | |
| 261 | Het³ | pent-1-yn-1-yl | | H | | H | H | H | H | H | A¹ | 3.89[a] | |
| 262 | Het³ | (4-fluorophenyl)ethynyl | | H | | H | H | H | H | H | A¹ | 4.16[b] | |
| 263 | Het³ | 3-(benzyloxy)prop-1-yn-1-yl | | H | | H | H | H | H | H | A¹ | 4.04[b] | |
| 264 | Het³ | (3-fluorophenyl)ethynyl | | H | | H | H | H | H | H | A¹ | 4.19[b] | |
| 265 | Het³ | [3-(trifluoromethoxy)phenyl]ethynyl | | H | | H | H | H | H | H | A¹ | 4.81[b] | |
| 266 | Het³ | [4-(trifluoromethoxy)phenyl]ethynyl | | H | | H | H | H | H | H | A¹ | 4.89[b] | |
| 267 | Het³ | [2-(trifluoromethyl)phenyl]ethynyl | | H | | H | H | H | H | H | A¹ | 4.51[b] | |
| 268 | Het¹ | (tert-butoxycarbonyl)(pentyloxy)amino | H | H | H | H | H | H | H | H | A¹ | 5.25[b] | |
| 269 | Het¹ | (pentyloxy)amino | H | H | H | H | H | H | H | H | A¹ | 3.87[b] | |
| 270 | Het³ | dec-1-yn-1-yl | | H | | H | H | H | H | H | A¹ | 6.45[a] | |
| 271 | Het³ | non-1-yn-1-yl | | H | | H | H | H | H | H | A¹ | 6.22[a] | |
| 272 | Het³ | oct-1-yn-1-yl | | H | | H | H | H | H | H | A¹ | 5.38[a] | |
| 273 | Het³ | hept-1-yn-1-yl | | H | | H | H | H | H | H | A¹ | 4.78[a] | |
| 274 | Het¹ | [(cyclohexyloxy)imino]methyl | H | H | H | H | H | H | H | H | A¹ | 4.89[a] | |
| 275 | Het¹ | hydroxymethyl | H | H | H | H | H | H | H | H | A¹ | 1.76[a] | |
| 276 | Het¹ | 5-butyl-4,5-dihydro-1,2-oxazol-3-yl | H | H | H | H | H | H | H | H | A¹ | 4.26[a] | |
| 277 | Het³ | (E)-2-cyclopropylethenyl | | H | | H | H | H | H | H | A¹ | 3.58[a] | |
| 278 | Het³ | (1E)-hex-1-en-1-yl | | H | | H | H | H | H | H | A¹ | 4.56[a] | |

TABLE 1-continued

| Ex. | Het | Z | R² | R³ | R⁴ | X¹ | X² | X³ | X⁴ | X⁵ | A | log p | MW measured |
|---|---|---|---|---|---|---|---|---|---|---|---|---|---|
| 279 | Het³ | (1E)-3-cyclopentylprop-1-en-1-yl | | H | | H | H | H | H | H | A¹ | 5.14[a] | |
| 280 | Het¹ | butoxy(tert-butoxycarbonyl)amino | H | H | H | H | H | H | H | H | A¹ | 4.75[b] | |
| 281 | Het¹ | (tert-butoxycarbonyl)(2-phenylethoxy)amino | H | H | H | H | H | H | H | H | A¹ | 4.89[b] | |
| 282 | Het¹ | (benzyloxy)(tert-butoxycarbonyl)amino | H | H | H | H | H | H | H | H | A¹ | 4.65[b] | |
| 283 | Het¹ | (tert-butoxycarbonyl)(cyclohexylmethoxy)amino | H | H | H | H | H | H | H | H | A¹ | 6.25[b] | |
| 284 | Het¹ | (cyclohexylmethoxy)amino | | H | H | H | H | H | H | H | A¹ | 4.44[b] | |
| 285 | Het¹ | (benzyloxy)amino | | H | H | H | H | H | H | H | A¹ | 3.14[b] | |
| 286 | Het¹ | butoxyamino | | H | H | H | H | H | H | H | A¹ | 3.39[b] | |
| 287 | Het¹ | (2-phenylethoxy)amino | | H | H | H | H | H | H | H | A¹ | 3.69[b] | |
| 288 | Het¹ | (cyclopentylmethyl)amino | | H | H | H | H | H | H | H | A¹ | 2.3[a] | |
| 289 | Het¹ | (cyclohexylmethyl)amino | | H | H | H | H | H | H | H | A¹ | 2.43[a] | |
| 290 | Het¹ | (cyclopropylmethyl)amino | | H | H | H | F | H | H | H | A¹ | 1.98[b] | |
| 291 | Het¹ | (2-cyclohexylethyl)amino | | H | H | H | F | H | H | H | A¹ | 3.27[b] | |
| 292 | Het¹ | (cyclohexylmethyl)amino | H | H | H | H | CH₃S | H | H | H | A¹ | 3.02[b] | |
| 293 | Het³ | (4-ethylphenyl)ethynyl | | H | | H | F | H | H | H | A¹ | 5[b] | |
| 294 | Het³ | (4-ethoxyphenyl)ethynyl | | H | | H | F | H | H | H | A¹ | 4.62[b] | |
| 295 | Het³ | (3-phenylpropyl)amino | H | H | | H | CH₃S | H | H | H | A¹ | 2.73[b] | |
| 296 | Het¹ | hexylamino | H | H | H | H | CH₃S | H | H | H | A¹ | 2.78[b] | |
| 297 | Het³ | hexylamino | | H | | H | CH₃S | H | H | H | A¹ | 3.92[b] | |
| 298 | Het¹ | (2-cyclohexylethyl)amino | H | H | H | H | CH₃S | H | H | H | A¹ | 3.17[b] | |
| 299 | Het³ | bromo | | H | | H | CH₃S | H | H | H | A¹ | 3.55[b] | |
| 300 | Het¹ | bicyclo[2.2.1]hept-2-ylamino | H | H | H | H | H | H | H | H | A¹ | 2.45[b] | |
| 301 | Het³ | hex-1-yn-1-yl | | H | | H | CH₃S | H | H | H | A¹ | 4.78[b] | |
| 302 | Het³ | cyclopentylethynyl | | H | | H | CH₃S | H | H | H | A¹ | 4.86[b] | |
| 303 | Het³ | cyclopropylethynyl | | H | | H | CH₃S | H | H | H | A¹ | 3.99[b] | |
| 304 | Het³ | cyclohexylethynyl | | H | | H | CH₃S | H | H | H | A¹ | 5.29[b] | |
| 305 | Het³ | (3-phenylpropyl)amino | | H | | H | CH₃S | H | H | H | A¹ | 3.71[b] | |
| 306 | Het¹ | bromo | H | H | H | H | H | H | H | H | A¹ | 3.19 | |
| 307 | Het¹ | bromo | | H | H | H | H | H | H | H | A¹ | 3.00 | |
| 308 | Het¹ | {[(2-methylpropyl)sulfanyl]carbonyl}amino | H | H | H | H | H | H | H | H | A¹ | 4.21[b] | |
| 309 | Het¹ | [(tert-butylsulfanyl)carbonyl]amino | H | H | H | H | H | H | H | H | A¹ | 4.19[b] | |
| 310 | Het¹ | hexanethioylamino | H | H | H | H | H | H | H | H | A¹ | 4.36[b] | |
| 311 | Het1 | hexylamino | H | H | H | H | N(CH₃)₂ | H | H | H | A1 | 2.44[b] | |
| 312 | Het³ | bromo | | H | | H | N(CH₃)₂ | H | H | H | A1 | 3.23[b] | |

Measurement of logP values was performed according EEC directive 79/831 Annex V.A8 by HPLC (High Performance Liquid Chromatography) on reversed phase columns with the following methods:
[a]Measurement was done at pH 2.3 with 0.1% phosphoric acid and acetonitrile as eluent.
[b]measurement of LC-MS was done at pH 2.7 with 0.1% formic acid in water and with acetonitrile (contains 0.1% formic acid) as eluent with a linear gradient from 10% acetonitrile to 95% acetonitrile.
[c]Measurement with LC-MS was done at pH 7.8 with 0.001 molar ammonium hydrogen carbonate solution in water as eluent with a linear gradient from 10% acetonitrile to 95% acetonitrile.
Calibration was done with not branched alkan2-ones (with 3 to 16 carbon atoms) with known logP-values (measurement of logP values using retention times with linear interpolation between successive alkanones) . . . lambda-maX-values were determined using UV-spectra from 200 nm to 400 nm and the peak values of the chromatographic signals.
In table 1, M + H (or M H) means the molecular ion peak, plus or minus 1 a.m.u. (atomic mass unit) respectively, as observed in mass spectroscopy and M (ApcI+) means the molecular ion peak as it was found via positive atmospheric pressure chemical ionisation in mass spectroscopy
Molecular Weight measurement, Method:
[m1]UPLC-SQD Double bond geometry:
[m2]Quattroll-ESI
[m3]SQD-ESI
[m4]HCOOH In the following list we specify the double bond geometry of the examples of table 1 as shown here:

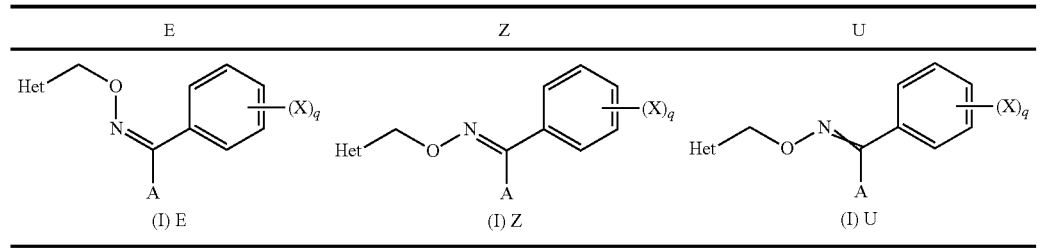

Example (Double Bond Geometry) of the Examples of Table 1:
1(E), 2(E), 3(E), 4(E), 5(E), 6(E), 7(E), 8(E), 9(E), 10(E), 11(E), 12(E), 13(E), 14(U), 15(U), 16(U), 17(U), 18(U), 19(U), 20(U), 21(E), 22(U), 23(U), 24(U), 25(U), 26(U), 27(U), 28(U), 29(U), 30(U), 31(U), 32(U), 33(U), 34(U), 35(U), 36(U), 37(U), 38(U), 39(U), 40(U), 41(U), 42(U), 43(U), 44(U), 45(U), 46(U), 47(U), 48(U), 49(U), 50(U), 51(U), 52(U), 53(U), 54(U), 55(U), 56(U), 57(U), 58(U), 59(U), 60(U), 61(U), 62(U), 63(U), 64(U), 65(U), 66(U), 67(U), 68(U), 69(U), 70(U), 71(U), 72(U), 73(U), 74(U), 75(U), 76(U), 77(U), 78(U), 79(U), 80(U), 81(U), 82(U), 83(U), 84(U), 85(U), 86(U), 87(U), 88(U), 89(U), 90(U), 91(U), 92(U), 93(U), 94(U), 95(U), 96(U), 97(U), 98(U), 99(U), 100(U), 101(U), 102(U), 103(U), 104(U), 105(U), 106(U), 107(U), 108(U), 109(U), 110(U), 111(U), 112(U), 113(U), 114(U), 115(U), 116(U), 117(U), 118(U), 119(U), 120(U), 121(U), 122(U), 123(U), 124(U), 125(U), 126(U), 127(U), 128(U), 129(U), 130(U), 131(U), 132(U), 133(U), 134(U), 135(U), 136(U), 137(U), 138(U), 139(U), 140(U), 141(U), 142(U), 143(U), 144(U), 145(U), 146(U), 147(U), 148(U), 149(U), 150(U), 151(U), 152(U), 153(U), 154(U), 155(U), 156(U), 157(U), 158(U), 159(U), 160(U), 161(U), 162(U), 163(U), 164(U), 165(U), 166(U), 167(U), 168(U), 169(U), 170(U), 171(U), 172(U), 173(U), 174(U), 175(U), 176(U), 177(U), 178(U), 179(U), 180(U), 181(U), 182(U), 183(U), 184(U), 185(U), 186(U), 187(U), 188(U), 189(U), 190(U), 191(U), 192(U), 193(U), 194(U), 195(U), 196(U), 197(U), 198(U), 199(Z), 200(U), 201(U), 202(U), 203(U), 204(U), 205(U), 206(U), 207(U), 208(U), 209(U), 210(U), 211(U), 212(U), 213(U), 214(U), 215(U), 216(U), 217(U), 218(U), 219(U), 220(U), 221(U), 222(U), 223(U), 224(U), 225(U), 226(U), 227(U), 228(U), 229(U), 230(U), 231(U), 232(U), 233(U), 234(U), 235(U), 236(U), 237(U), 238(U), 239(U), 240(U), 241(U), 242(U), 243(U), 244(U), 245(U), 246(U), 247(U), 248(U), 249(U), 250(U), 251(U), 252(U), 253(U), 254(U), 255(U), 256(U), 257(U), 258(U), 259(U), 260(U), 261(U), 262(U), 263(U), 264(U), 265(U), 266(U), 267(U), 268(U), 269(U), 270(U), 271(U), 272(U), 273(U), 274(U), 275(U), 276(U), 277(U), 278(U), 279(U), 280(U), 281(U), 282(U), 283(U), 284(U), 285(U), 286(U), 287(U), 288(U), 289(U), 290(U), 291(U), 292(U), 293(U), 294(U), 295(U), 296(U), 297(U), 298(U), 299(U), 300(Z), 301(U), 302(U), 303(U), 304(U), 305(U), 306(Z), 307(E), 308(Z), 309(Z), 310(Z), 311(U), 312(U).

EXAMPLE A

*Phytophthora* Test (Tomato)/Preventive

Solvent: 49 parts by weight of N,N-Dimethylformamide
Emulsifier: 1 part by weight of Alkylarylpolyglycolether To produce a suitable preparation of active compound, 1 part by weight of active compound is mixed with the stated amounts of solvent and emulsifier, and the concentrate is diluted with water to the desired concentration.

To test for preventive activity, young plants are sprayed with the preparation of active compound at the stated rate of application. One day after this treatment, the plants are inoculated with an aqueous spore suspension of *Phytophthora infestans*. The plants remain for one day in an incubation cabinet at approximately 22° C. and a relative atmospheric humidity of 100%. Then the plants are placed in an incubation cabinet at approximately 20° C. and a relative atmospheric humidity of 96%.

The test is evaluated 7 days after the inoculation. 0% means an efficacy which corresponds to that of the control, while an efficacy of 100% means that no disease is observed.

In this test the following examples of table 1 according to the invention showed efficacy of 70% or even higher at a concentration of 500 ppm of active ingredient.

Example Nr. 1, 22, 23, 25, 26, 27, 28, 29, 30, 32, 37, 50, 59, 61, 62, 64, 65, 66, 67, 68, 69, 70, 71, 72, 80, 81, 82, 87, 88, 89, 90, 92, 93, 94, 95, 97, 98, 99, 100, 101, 102, 103, 104, 105, 106, 107, 108, 109, 110, 112, 113, 114, 115, 116, 117, 118, 119, 120, 121, 122, 123, 124, 126, 127, 128, 129, 130, 131, 132, 133, 134, 135, 136, 137, 138, 142, 143, 144, 160, 163, 164, 165 and 166.

EXAMPLE B

*Plasmopara* Test (Grapevines)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated rate of application. After the spray coating has dried on, the plants are inoculated with an aqueous spore suspension of *Plasmopara viticola* and then remain for 1 day in an incubation cabinet at approximately 20° C. and a relative atmospheric humidity of 100%. The plant is subsequently placed for 4 days in a greenhouse at approximately 21° C. and a relative atmospheric humidity of approximately 90%. The plants are then misted and placed for 1 day in an incubation cabinet.

The test is evaluated 6 days after the inoculation. 0% means an efficacy which corresponds to that of the control, while an efficacy of 100% means that no disease is observed.

In this test the following examples of table 1 according to the invention showed efficacy of 70% or even higher at a concentration of 100 ppm of active ingredient.

Example Nr. 22, 23, 25, 26, 27, 29, 30, 59, 61, 62, 64, 65, 66, 67, 68, 69, 70, 71, 72, 80, 81, 88, 89, 90, 92, 97, 98, 99, 100, 101, 104, 105, 106, 107, 108, 109, 112, 113, 114, 115, 115, 116, 117, 118, 119, 120, 121, 122, 123, 124, 126, 127, 128, 129, 130, 131, 132, 133, 134, 137, 143 and 144.

EXAMPLE C

In Vitro-Test for the Calculation of the ED50-Value with *Pythium aphanidermatum*

Wells of 96-hole microtitre plates are filled with 100 of a solution of the test compound in methanol together with the emulsifier alkylaryl polyglycol ether. Thereafter, the solvent is evaporated in a hood. At the next step, into each well 2000 of liquid potato dextrose medium is given that has been amended with an appropriate concentration of spores or mycelium suspension of the test fungus. The resulting concentrations of the test compounds in the microtitre well are 50, 5, 0.5 and 0.05 ppm. The resulting concentration of the emulsifier in all wells is constantly 300 ppm. With the aid of a photometer the extinction in all wells is measured at the wavelength of 620 nm.

The microtiter plates are then transferred for 3-5 days onto a shaker at 20° C. and 85% relative humidity.

At the end of the incubation time the growth of the test organisms is measured again photometrically at the wavelength of 620 nm. The difference between the two extinction values (taken before and after incubation) is proportional to the growth of the test organism. Based on the A extinction data from the different test concentrations and that of the untreated test organism (control) a dose-response curve is calculated. The concentration that is necessary to give 50% growth inhibition is defined and reported as ED50-value (=Effective Dose that causes 50% growth inhibition) in ppm (=mg/l). In this test the following examples of table 1 showed an ED50-value lower than 1 ppm.

Example Nr. 1, 10, 19, 22, 23, 24, 25, 26, 27, 29, 30, 31, 32, 34, 36, 39, 42, 43, 44, 46, 48, 49, 50, 51, 59, 62, 65, 66, 67, 68, 69, 71, 73, 79, 81, 82, 87, 89, 90, 91, 92, 93, 94, 95, 96, 97, 98, 99, 100, 101, 102, 103, 104, 105, 106, 107, 108, 109, 110, 112, 113, 114, 115, 116, 117, 118, 119, 120, 121, 122 and 123.

The following examples illustrate in a non-limiting manner the preparation and efficacy of the compounds of formula (I) according to the invention.

Preparation of N-[(2-bromo-1,3-thiazol-4-yl)methoxy]-1-(1-methyl-1H-tetrazol-5-yl)-1-phenyl-methanimine (Compound 32) According to Process P1

To a stirred solution of N-hydroxy-1-(1-methyl-1H-tetrazol-5-yl)-1-phenylmethanimine (2.54 g, 12.5 mmol) in acetonitrile (75 mL), were added cesium carbonate (8.55 g, 26.2 mmol), sodium iodide (187 mg, 1.25 mmol) and 2-Bromo-4-bromomethyl-thiazole (3.53 g, 13.7 mmol). The resulting suspension was stirred at 25° C. for 30 minutes, then at 40° C. for 90 minutes. After cooling, the suspension was diluted with ethyl acetate (80 mL), filtered over a plug of celite, the solvents were evaporated in vacuo. Purification on silica gel afforded N-[(2-bromo-1,3-thiazol-4-yl)methoxy]-1-(1-methyl-1H-tetrazol-5-yl)-1-phenyl-methanimine as an oil that solidified on standing after 2 days (4.19 g, yield 88%).

HPLC/MS: m/z=379 (M+H); logP$_{(HCOOH)}$=3.11

Preparation of N-[(2,5-dichloro-1,3-thiazol-4-yl)methoxy]-1-(1-methyl-1H-tetrazol-5-yl)-1-phenyl-methanimine (Compound 113) According to Process P1

To a stirred solution of N-hydroxy-1-(1-methyl-1H-tetrazol-5-yl)-1-phenylmethanimine (2.15 g, 10.58 mmol, 1.0 eq.) in 20 ml of MeCN was added $Cs_2CO_3$ (4.12 g, 12.69 mmol, 1.2 eq.) followed by KI (0.17 g, 1.05 mmol, 0.1 eq.) in one portion. The resulting suspension was stirred for 5 mins before addition of 2,5-dichloro-4-(chloromethyl)-1,3-thiazole (2.35 g, 11.63 mmol, 1.1 eq.) in one portion. The reaction was stirred for 24 hrs at room temperature. The solvent was evaporated and the residue was dissolved in EtOAc and washed with $H_2O$. The organic layer was separated, dried over $MgSO_4$ and concentrated. The residue was purified by chromatography on silica gel to give N-[(2,5-dichloro-1,3-thiazol-4-yl)methoxy]-1-(1-methyl-1H-tetrazol-5-yl)-1-phenylmethanimine (1.65 g, 42% yield, 86:14 mixture of stereoisomers) as a yellow viscous oil.

HPLC/MS: m/z=370 (M+H); logP$_{(HCOOH)}$=3.67

Preparation of N-[(2-bromo-5-methyl-1,3-thiazol-4-yl)methoxy]-1-(1-methyl-1H-tetrazol-5-yl)-1-phenylmethanimine (compound 175) According to Process P1

Step 1

Preparation of methyl 2-bromo-5-methyl-1,3-thiazole-4-carboxylate

To a stirred suspension of methyl 2-amino-5-methyl-1,3-thiazole-4-carboxylate (5 g, 29.03 mmol, 1 eq.) in 75 ml of MeCN, were added sodium bromide (5.97 g, 58.07 mmol, 2 eq.), Copper (I) bromide (6.08 g, 31.93 mmol, 1.1 eq.) and t-Butylnitrite (90%, 3.65 g, 31.93 mmol, 1.1 eq.). The reaction was slowly heated to 80° C. for 1 h and allowed to cool. MeCN was evaporated and 100 ml DCM were added to the residue. The crude was triturated, filtered through "celite" plug and washed with further 50 ml of EtOAc. The organic layers were combined, dried over $MgSO_4$, and evaporated to give methyl 2-bromo-5-methyl-1,3-thiazole-4-carboxylate (3.91 g, 42% yield) as a yellow solid.

HPLC/MS: m/z=236 (M+H); logP$_{(HCOOH)}$=1.84

Step 2

Preparation of (2-bromo-5-methyl-1,3-thiazol-4-yl)methanol

To a stirred solution of methyl 2-bromo-5-methyl-1,3-thiazole-4-carboxylate (2.89 g, 12.26 mmol, 1 eq.) in 120 ml dry THF cooled to 5° C., was added $LiBH_4$ (2M in THF, 12.26 ml, 24.53 mmol, 2 eq.) followed by MeOH (0.994 ml, 24.53 mmol, 2 eq.). The reaction was allowed to warm to r.t. and was stirred for further 18 hrs. The reaction was quenched by addition of sat. aqueous $NH_4Cl$ and diluted with DCM. The aqueous layer was extracted with DCM, and the organic layers combined, dried over $MgSO_4$ and concentrated. The residue was chromatographed on silica gel to (2-bromo-5-methyl-1,3-thiazol-4-yl)methanol (2.07 g, 77% yield) as a white solid.

HPLC/MS: m/z=209 (M+H); logP$_{(HCOOH)}$=1.10

Step 3

Preparation of 2-bromo-4-(bromomethyl)-5-methyl-1,3-thiazole

To a stirred solution thionyl bromide (2.27 g, 10.94 mmol, 1.1 eq.) in 25 ml dry DCM, cooled to 5° C., was added dropwise a solution of (2-bromo-5-methyl-1,3-thiazol-4-yl)methanol (2.07 g, 9.94 mmol, 1 eq.) and pyridine (0.865 g, 10.94 mmol, 1.1 eq.) in 15 ml dry DCM. On complete addition, the cooling bath was removed, the reaction warmed to room temperature and stirred 1.5 hr. 100 ml of water and 100 ml of DCM were added and stirring allowed for 2 mins. The organic layer was separated, dried over $MgSO_4$ and evaporated. The residue was purified by chromatography on silica gel to give 2-bromo-4-(bromomethyl)-5-methyl-1,3-thiazole (1.94 g, 72% yield) as a white solid.

HPLC/MS: m/z=271 (M+H); logP$_{(HCOOH)}$=2.64

Preparation of N-[(2-bromo-5-methyl-1,3-thiazol-4-yl)methoxy]-1-(1-methyl-1H-tetrazol-5-yl)-1-phenylmethanimine To a stirred solution of N-hydroxy-1-(1-methyl-1H-tetrazol-5-yl)-1-phenylmethanimine (1.47 g, 7.25 mmol, 1.0 eq.) in 25 ml of MeCN was added $Cs_2CO_3$ (2.59 g, 7.97 mmol, 1.1 eq.) followed by KI (0.120 g, 0.725 mmol, 0.1 eq.) in one portion. The resulting suspension was stirred for 5 mins before addition of 2-bromo-4-(bromomethyl)-5-methyl-1,3-thiazole (1.96 g, 7.25 mmol, 1 eq.) in one portion. The reaction was stirred for 24 hrs at room temperature. The solvent was evaporated and the residue was dissolved in EtOAc and washed with $H_2O$. The organic layer was separated, dried over $MgSO_4$ and concentrated. The residue was purified by chromatography on silica gel to give N-[(2-bromo-5-methyl-1,3-thiazol-4-yl)methoxy]-1-(1-methyl-1H-tetrazol-5-yl)-1-phenylmethanimine (2.92 g, 97% yield, 93:7 mixture of stereoisomers) as a white solid.

HPLC/MS: m/z=(M+H); logP$_{(HCOOH)}$=3.37

Preparation of N-[(2-bromo-1,3-thiazol-4-yl)methoxy]-1-(5-methyl-1H-tetrazol-1-yl)-1-phenylmethanimine (compound 145) According to Process P1

To a stirred solution of N-hydroxy-1-(5-methyl-1H-tetrazol-1-yl)-1-phenylmethanimine (2.0 g, 9.84 mmol, 1.0 eq.) in 50 ml of MeCN was added $Cs_2CO_3$ (3.52 g, 10.82 mmol, 1.2 eq.) followed by KI (0.163 g, 0.984 mmol, 0.1 eq.) in one portion. The resulting suspension was stirred for 5 mins before addition of 2-bromo-4-(bromomethyl)-1,3-thiazole (2.52 g, 9.84 mmol, 1 eq.) in one portion. The reaction was stirred for 24 hrs at room temperature. The solvent was evaporated then the residue was dissolved in EtOAc and washed with $H_2O$. The organic layer was separated, dried over $MgSO_4$ and concentrated. The residue was purified by chromatography on silica gel to give N-[(2-bromo-1,3-thiazol-4-yl)methoxy]-1-(5-methyl-1H-tetrazol-1-yl)-1-phenylmethanimine (3.3 g, 88% yield) as a yellow viscous oil.

HPLC/MS: m/z=380 (M+H); $logP_{(HCOOH)}$=3.15

Preparation of N-[(6-bromopyridin-2-yl)methoxy]-1-(1-methyl-1H-tetrazol-5-yl)-1-phenylmethanimine (Compound 17) According to Process P1

To a cooled (0° C.) stirred solution of N-hydroxy-1-(1-methyl-1H-tetrazol-5-yl)-1-phenylmethanimine (6.47 g, 31.88 mmol, 1.0 eq.) in 250 ml of MeCN, was added dropwise DBN (4.35 g, 35.07 mmol, 1.0 eq.). The reaction was stirred for 5 mins before addition of 2-bromo-6-(bromomethyl)pyridine (8.8 g, 35.07 mmol, 1.1 eq.) portionwise. The mixture was stirred for further 5 mins before removal of the cooling bath and continued at ambient temperature. MeCN was evaporated and the residue was purified by chromatography on silica gel to yield N-[(6-bromopyridin-2-yl)methoxy]-1-(1-methyl-1H-tetrazol-5-yl)-1-phenylmethanimine (9.4 g, 75% yield, 10:1 mixture of stereoisomers) as a pale yellow oil.

HPLC/MS: m/z=373 (M+H); $logP_{(HCOOH)}$=3.25[a]; 3.15[b]

Preparation of N-[(6-bromo-3-fluoro-pyridin-2-yl)methoxy]-1-(1-methyl-1H-tetrazol-5-yl)-1-phenylmethanimine (Compound 96) According to Process P1

Step 1

Preparation of 6-bromo-3-fluoro-2-methylpyridine 1-oxide

A solution of 6-bromo-3-fluoro-2-methylpyridine (2.84 g, 14.94 mmol, 1 eq.) was dissolved in DCM (250 ml) and cooled to 0° C. Then mCPBA (7.34 g, 29.89 mmol, 2 eq.) was added by portions and the reaction was warmed to r.t. and stirred for 48 h. A sat. aqueous solution of $NaHCO_3/Na_2S_2O_3$ (1/1) was added and stirring allowed for 5 min. Then DCM was added and the layers separated. The aqueous layer was extracted with DCM then the organics were combined, dried over $MgSO_4$ and concentrated. 6-bromo-3-fluoro-2-methylpyridine 1-oxide (2.94 g, 89%) was obtained as a white solid.

HPLC/MS: m/z=206 (M+H); $logP_{(HCOOH)}$=0.56

Step 2

Preparation of 6-bromo-3-fluoropyridin-2-yl)methanol 6-bromo-3-fluoro-2-methylpyridine 1-oxide (2.89 g, 14.02 mmol, 1 eq.) was dissolved in neat TFAA (10 ml) and stirred 30 min at room temperature and refluxed for 2 hrs. The solvent was evaporated and the residue diluted with DCM and basified with sat. aqueous $Na_2CO_3$. The organic layers was separated and washed with sat. aqueous $Na_2CO_3$, dried with $MgSO_4$ and concentrated. The crude was dissolved in THF and MeOH (1 ml) was added followed by $K_2CO_3$ (4.8 g, 35.07 mmol, 2.5 eq.). After 30 min of stirring, water was added and the reaction was extracted with EtOAc. The organic layers were combined, dried over $MgSO_4$ and concentrated. (6-bromo-3-fluoropyridin-2-yl)methanol (2.54 g, 79% yield) was obtained as a yellow solid.

HPLC/MS: m/z=206 (M+H); $logP_{(HCOOH)}$=0.92

Step 3

Preparation of 6-bromo-2-(bromomethyl)-3-fluoropyridine

To a stirred solution thionyl bromide (2.44 g, 11.78 mmol, 1.05 eq.) in 50 ml dry DCM, cooled to 5° C., was added dropwise a solution of (6-bromo-3-fluoropyridin-2-yl)methanol (2.54 g, 11.22 mmol, 1 eq.) and pyridine (0.931 g, 11.78 mmol, 1.05 eq.) in 15 ml dry DCM. On complete addition, the cooling bath was removed, the reaction warmed to room temperature and stirred 1.5 hr. 150 ml of water and 150 ml of DCM were added and stirring allowed for 2 mins. The organic layer was separated, dried of $MgSO_4$ and concentrated. The residue was purified by chromatography on silica gel to give 6-bromo-2-(bromomethyl)-3-fluoropyridine (2.89 g, 87% yield) as a white solid.

HPLC/MS: m/z=268 (M+H); $logP_{(HCOOH)}$=2.58

Step 4

Preparation of N-[(6-bromo-3-fluoro-pyridin-2-yl)methoxy]-1-(1-methyl-1H-tetrazol-5-yl)-1-phenylmethanimine To a stirred solution of N-hydroxy-1-(5-methyl-1H-tetrazol-1-yl)-1-phenylmethanimine (2 g, 9.84 mmol, 1.0 eq.) in 50 ml of MeCN was added $Cs_2CO_3$ (3.51 g, 10.82 mmol, 1.1 eq.) followed by KI (0.163 g, 0.98 mmol, 0.1 eq.) in one portion. The resulting suspension was stirred for 5 mins before addition of 6-bromo-2-(bromomethyl)-3-fluoropyridine (0.419 g, 2.1 mmol, 1 eq.) in one portion. The reaction was stirred for 24 hrs at room temperature. The solvent was evaporated and the residue was dissolved in EtOAc and washed with $H_2O$. The organic layer was separated, dried over $MgSO_4$ and concentrated. The residue was purified on silica gel to give N-[(6-bromo-3-fluoro-pyridin-2-yl)methoxy]-1-(1-methyl-1H-tetrazol-5-yl)-1-phenylmethanimine (0.15 g, 19% yield) as a yellow viscous oil.

HPLC/MS: m/z=391 (M+H); $logP_{(HCOOH)}$=3.27

Preparation of N-[(6-bromo-5-methoxypyridin-2-yl)methoxy]-1-(1-methyl-1H-tetrazol-5-yl)-1-phenylmethanimine (Compound 125) According to Process P1

To a stirred solution of N-hydroxy-1-(5-methyl-1H-tetrazol-1-yl)-1-phenylmethanimine (0.723 g, 3.55 mmol, 1.0 eq.) in 10 ml of MeCN was added $Cs_2CO_3$ (1.275 g, 3.912 mmol, 1.1 eq.) followed by KI (0.059 g, 0.356 mmol, 0.1 eq.) in one portion. The resulting suspension was stirred for 5 mins before addition of 2-bromo-6-(bromomethyl)-3-methoxypyridine (1 g, 3.55 mmol, 1 eq.) in one portion. The reaction was stirred for 24 hrs at room temperature. The solvent was evaporated and the residue was dissolved in EtOAc and washed with $H_2O$. The organic layer was separated, dried over $MgSO_4$ and concentrated. The residue was purified on silica gel to give N-[(6-bromo-5-methoxypyridin-2-yl)methoxy]-1-(1-methyl-1H-tetrazol-5-yl)-1-phenylmethanimine (1.42 g, 98% yield) as a yellow viscous oil.

HPLC/MS: m/z=405 (M+H); logP$_{(HCOOH)}$=3.13

Preparation of N-({2-[3-(benzyloxy)prop-1-yn-1-yl]-1,3-thiazol-4-yl}methoxy)-1-(1-methyl-1H-tetrazol-5-yl)-1-phenylmethanimine (Compound 263) According to Process P5

A solution of N-[(2-bromo-1,3-thiazol-4-yl)methoxy]-1-(1-methyl-1H-tetrazol-5-yl)-1-phenyl-methanimine (190 mg, 0.50 mmol), benzyl propargyl ether (149 mg, 1.00 mmol), copper(I) iodide (9.5 mg, 0.05 mmol), tetrakis(triphenylphosphine)palladium(0) (28.9 mg, 0.02 mmol), N,N-diisopropylethylamine (258 mg, 2.0 mmol) in degassed tetrahydrofuran (2.5 mL) was stirred under an Argon atmosphere at 50° C. for 14 h. After the addition of diethyl-ether (2 mL) the suspension was filtered over a pad of silica gel and the filtrate was concentrated in vacuo. Purification on silica gel afforded N-({2-[3-(benzyloxy)prop-1-yn-1-yl]-1,3-thiazol-4-yl}methoxy)-1-(1-methyl-1H-tetrazol-5-yl)-1-phenylmethanimine as a thick oil (144 mg, yield 62%).

HPLC/MS: m/z=445 (M+H); logP$_{(HCOOH)}$=4.04

Preparation of N-{[2-(cyclopropylethynyl)-1,3-thiazol-4-yl]methoxy}-1-(1-methyl-1H-tetrazol-5-yl)-1-phenylmethanimine (Compound 70) According to Process P5

To a stirred solution of N-[(2-bromo-1,3-thiazol-4-yl)methoxy]-1-(1-methyl-1H-tetrazol-5-yl)-1-phenylmethanimine (1 g, 2.63 mmol, 1 eq.) in 20 ml dry THF "degassed" with N$_2$, was added cyclopropylacetylene (70%, 0.996 g, 10.54 mmol, 4 eq.) followed by N-ethyldiisopropylamine (1.36 g, 10.54 mmol, 4 eq.), Copper(I) Iodide (0.025 g, 0.132 mmol, 0.05 eq.) and Tetrakis(triphenylphosphine)palladium (0.152 g, 0.132 mmol, 0.05 eq.). The reaction was stirred for 20 hrs at room temperature for complete conversion. The reaction mixture was diluted with EtOAc (50 ml), filtered through "Chem Elut" cartridge, washed with fresh EtOAc (2×20 ml) and the filtrate was evaporated. The residue was purified by chromatography on silica gel to give N-{[2-(cyclopropylethynyl)-1,3-thiazol-4-yl]methoxy}-1-(1-methyl-1H-tetrazol-5-yl)-1-phenylmethanimine (0.57 g, 60% yield, single stereoisomer) as a brown gum.

HPLC/MS: m/z=365 (M+H); logP$_{(HCOOH)}$=3.58

Preparation of N-{[5-chloro-2-(cyclopropylethynyl)-1,3-thiazol-4-yl]methoxy}-1-(1-methyl-1H-tetrazol-5-yl)-1-phenylmethanimine (Compound 114) According to Process P5

To a stirred solution of N-[(2,5-dichloro-1,3-thiazol-4-yl)methoxy]-1-(1-methyl-1H-tetrazol-5-yl)-1-phenylmethanimine (0.15 g, 0.406 mmol, 1 eq.) in 3 ml dry THF "degassed" with N$_2$, was added Cyclopropylacetylene (0.029 g, 0.447 mmol, 1.1 eq.) followed by N-ethyldiisopropylamine (0.209 g, 1.62 mmol, 4 eq.), Copper Iodide (0.015 g, 0.081 mmol, 0.2 eq.) and Tetrakis(triphenylphosphine)palladium (0.046 g, 0.041 mmol, 0.1 eq.). The reaction was microwaved 120° C./normal/fixed hold/pre stir 100 s for 180 s. The reaction was diluted with EtOAc and filtered through a "celite" plug. The solvent was evaporated and the residue purified by chromatography on silica gel to give N-{[5-chloro-2-(cyclopropylethynyl)-1,3-thiazol-4-yl]methoxy}-1-(1-methyl-1H-tetrazol-5-yl)-1-phenylmethanimine (0.137 g, 71% yield, 78:5 mixture of stereoisomers) as a yellow viscous oil.

HPLC/MS: m/z=(M+H); logP$_{(HCOOH)}$=4.59

Preparation of give N-{[5-methyl-2-(pent-1-yn-1-yl)-1,3-thiazol-4-yl]methoxy}-1-(1-methyl-1H-tetrazol-5-yl)-1-phenylmethanimine (Compound 181) According to Process P5

To a stirred solution of N-[(2-bromo-5-methyl-1,3-thiazol-4-yl)methoxy]-1-(1-methyl-1H-tetrazol-5-yl)-1-phenyl-methanimine (0.2 g, 0.509 mmol, 1 eq.) in 3 ml dry THF "degassed" with N$_2$, was added pentyne (0.069 g, 1.01 mmol, 2 eq.) followed by triethylamine (0.205 g, 2.03 mmol, 4 eq.), Copper Iodide (0.014 g, 0.076 mmol, 0.15 eq.) and Tetrakis (triphenylphosphine)palladium (0.029 g, 0.025 mmol, 0.05 eq.). The reaction was stirred for 20 hrs at room temperature for complete conversion. The reaction was diluted with EtOAc (50 ml), filtered through "Chem Elut" cartridge, washed with fresh EtOAc (2×20 ml) and the filtrate was evaporated. The residue was chromatographed on silica gel to give N-{[5-methyl-2-(pent-1-yn-1-yl)-1,3-thiazol-4-yl]methoxy}-1-(1-methyl-1H-tetrazol-5-yl)-1-phenylmethanimine (0.141 g, 69% yield) as a brown gum.

HPLC/MS: m/z=(M+H); logP$_{(HCOOH)}$=3.83

Preparation of give N-{[5-methyl-2-(pent-1-yn-1-yl)-1,3-thiazol-4-yl]methoxy}-1-(1-methyl-1H-tetrazol-5-yl)-1-phenylmethanimine (Compound 159) According to Process P5

To a stirred solution of N-[(2-bromo-1,3-thiazol-4-yl)methoxy]-1-(5-methyl-1H-tetrazol-1-yl)-1-phenylmethanimine (0.2 g, 0.527 mmol, 1 eq.) in 3 ml dry THF "degassed" with N$_2$, was added cyclopropylacetylene (0.069 g, 1.05 mmol, 2 eq.) followed by triethylamine (0.213 g, 2.1 mmol, 4 eq.), Copper Iodide (0.015 g, 0.079 mmol, 0.15 eq.) and Tetrakis(triphenylphosphine)palladium (0.030 g, 0.026 mmol, 0.05 eq.). The reaction was stirred for 20 hrs at room temperature for complete conversion. The reaction was diluted with EtOAc (50 ml), filtered through "Chem Elut" cartridge, washed with fresh EtOAc (2×20 ml) and the filtrate was concentrated. The residue was chromatographed on silica gel to give N-{[2-(cyclopropylethynyl)-1,3-thiazol-4-yl]methoxy}-1-(5-methyl-1H-tetrazol-1-yl)-1-phenylmethanimine (0.108 g, 56% yield) as a brown gum.

HPLC/MS: m/z=(M+H); logP$_{(HCOOH)}$=3.65

Preparation of give N-{[6-(hex-1-yn-1-yl)pyridin-2-yl]methoxy}-1-(1-methyl-1H-tetrazol-5-yl)-1-phenylmethanimine (Compound 23) According to Process P5

To a stirred solution of N-[(6-bromopyridin-2-yl)methoxy]-1-(1-methyl-1H-tetrazol-5-yl)-1-phenylmethanimine (0.20 g, 0.536 mmol, 1 eq.) in 2 ml dry THF "degassed" with N$_2$, was added hexyne (0.176 g, 2.14 mmol, 4 eq.) followed by N-ethyldiisopropylamine (0.361 g, 2.79 mmol, 4 eq.), Copper Iodide (0.031 g, 0.161 mmol, 0.3 eq.) and Tetrakis (triphenylphosphine)palladium (0.186 g, 0.161 mmol, 0.3 eq.). The reaction was microwaved 120° C./normal/fixed hold/pre stir 100 s for 180 s. The reaction was diluted with EtOAc and filtered through a "celite" plug. The solvent was evaporated and the residue purified by chromatography on silica gel to give N-{[6-(hex-1-yn-1-yl)pyridin-2-yl]methoxy}-1-(1-methyl-1H-tetrazol-5-yl)-1-phenylmethanimine (0.19 g, 85% yield) as a yellow viscous oil.

HPLC/MS: m/z=375 (M+H); logP$_{(HCOOH)}$=4.26

Preparation of give N-{[6-(hex-1-yn-1-yl)pyridin-2-yl]methoxy}-1-(1-methyl-1H-tetrazol-5-yl)-1-phenylmethanimine (Compound 99) According to Process P5

To a stirred solution of N-{[5-(cyclopropylethynyl)-1,2,4-thiadiazol-3-yl]methoxy}-1-(1-methyl-1H-tetrazol-5-yl)-1-phenylmethanimine (0.285 g, 0.729 mmol, 1 eq.) in 2 ml dry THF "degassed" with $N_2$, was added hexyne (0.149 g, 1.82 mmol, 2.5 eq.) followed by N-ethyldiisopropylamine (0.375 g, 2.91 mmol, 4 eq.), Copper Iodide (0.020 g, 0.109 mmol, 0.15 eq.) and Tetrakis(triphenylphosphine)palladium (0.084 g, 0.073 mmol, 0.1 eq.). The reaction was microwaved 120° C./normal/fixed hold/pre stir 100 s for 180 s. The reaction was diluted with EtOAc and filtered through a "celite" plug. The solvent was evaporated and the residue purified by chromatography on silica gel to give N-{[3-fluoro-6-(hex-1-yn-1-yl)pyridin-2-yl]methoxy}-1-(1-methyl-1H-tetrazol-5-yl)-1-phenylmethanimine (0.245 g, 83% yield) as a yellow viscous oil.

HPLC/MS: m/z=393 (M+H); $logP_{(HCOOH)}$=4.41

Preparation of give N-{[6-(cyclopropylethynyl)-5-methoxypyridin-2-yl]methoxy}-1-(1-methyl-1H-tetrazol-5-yl)-1-phenylmethanimine (Compound 126) According to Process P5

To a stirred solution of N-[(6-bromo-5-methoxypyridin-2-yl)methoxy]-1-(1-methyl-1H-tetrazol-5-yl)-1-phenylmethanimine (0.150 g, 0.372 mmol, 1 eq.) in 2 ml dry THF "degassed" with $N_2$, was added cyclopropylacetylene (0.073 g, 1.11 mmol, 3 eq.) followed by N-ethyldiisopropylamine (0.191 g, 1.48 mmol, 4 eq.), Copper Iodide (0.010 g, 0.056 mmol, 0.15 eq.) and Tetrakis(triphenylphosphine)palladium (0.042 g, 0.037 mmol, 0.1 eq.). The reaction was microwaved 120° C./normal/fixed hold/pre stir 100 s for 1200 s. The reaction was diluted with EtOAc and filtered through a "celite" plug. The solvent was evaporated and the residue purified by chromatography on silica gel to give N-{[6-(cyclopropylethynyl)-5-methoxypyridin-2-yl]methoxy}-1-(1-methyl-1H-tetrazol-5-yl)-1-phenylmethanimine (0.083 g, 57% yield) as a yellow viscous oil.

HPLC/MS: m/z=389 (M+H); $logP_{(HCOOH)}$=3.23

Preparation of give N-({2-[(1E)-hex-1-en-1-yl]-1,3-thiazol-4-yl}methoxy)-1-(1-methyl-1H-tetrazol-5-yl)-1-phenylmethanimine (Compound 278) According to Process P5

In a dried and purged vessel were added N-[(2-bromo-1,3-thiazol-4-yl)methoxy]-1-(1-methyl-1H-tetrazol-5-yl)-1-phenylmethanimine (0.2 g, 0.527 mmol, 1 eq.), (1E)-hex-1-en-1-ylboronic acid (0.074 g, 0.58 mmol, 1.1 eq.), $Na_2CO_3$ (0.117 g, 1.107 mmol, 2.1 eq.) and Tetrakis(triphenylphosphine)palladium (0.030 g, 0.026 mmol, 0.05 eq.). A mixture of solvent was added toluene/ethanol/water (4/1/1) was added and the vessel purged with argon and sealed. The reaction was heated to 90° C. for 6 hrs. After cooling, 10 ml of EtOAc were added and the solids were filtered through a "Celite" plug and washed with EtOAc. The organics were separated, dried over $MgSO_4$ and concentrated. The residue was purified by chromatography on silica gel to give N-({2-[(1E)-hex-1-en-1-yl]-1,3-thiazol-4-yl}methoxy)-1-(1-methyl-1H-tetrazol-5-yl)-1-phenylmethanimine (0.170 g, 80% yield) as a colorless gum.

HPLC/MS: m/z=383 (M+H); $logP_{(HCOOH)}$=4.56

Preparation of give N-({6-[(E)-2-cyclohexylvinyl]pyridin-2-yl}methoxy)-1-(1-methyl-1H-tetrazol-5-yl)-1-phenylmethanimine (Compound 93) According to Process P5

In a dried and purged vessel were added N-[(6-bromopyridin-2-yl)methoxy]-1-(1-methyl-1H-tetrazol-5-yl)-1-phenylmethanimine (0.2 g, 0.536 mmol, 1 eq.), [(E)-2-cyclohexylvinyl]boronic acid (0.090 g, 0.58 mmol, 1.1 eq.), $Na_2CO_3$ (0.119 g, 1.12 mmol, 2.1 eq.) and Tetrakis(triphenylphosphine)palladium (0.030 g, 0.027 mmol, 0.05 eq.). A mixture of solvent was added toluene/ethanol/water (4/1/1) was added and the vessel purged with argon and sealed. The reaction was heated to 90° C. for 6 hrs. After cooling, 10 ml of EtOAc were added and the solids were filtered through a "Celite" plug and washed with EtOAc. The organics were separated, dried over $MgSO_4$ and concentrated. The residue was purified by chromatography on silica gel to give N-({6-[(E)-2-cyclohexylvinyl]pyridin-2-yl}methoxy)-1-(1-methyl-1H-tetrazol-5-yl)-1-phenylmethanimine (0.155 g, 68% yield) as a colorless gum.

HPLC/MS: m/z=403 (M+H); $logP_{(HCOOH)}$=5.05

Preparation of give 1-(1-methyl-1H-tetrazol-5-yl)-1-phenyl-N-[(6-phenylpyridin-2-yl)methoxy]methanimine (Compound 31) According to Process P5

In a dried and purged vessel were added N-[(6-bromopyridin-2-yl)methoxy]-1-(1-methyl-1H-tetrazol-5-yl)-1-phenylmethanimine (0.2 g, 0.536 mmol, 1 eq.), phenylboronic acid (0.072 g, 0.58 mmol, 1.1 eq.), $Na_2CO_3$ (0.119 g, 1.12 mmol, 2.1 eq.) and Tetrakis(triphenylphosphine)palladium (0.030 g, 0.027 mmol, 0.05 eq.). A mixture of solvent was added toluene/ethanol/water (4/1/1) was added and the vessel purged with argon and sealed. The reaction was heated to 90° C. for 6 hrs. After cooling, 10 ml of EtOAc were added and the solids were filtered through a "Celite" plug and washed with EtOAc. The organics were separated, dried over $MgSO_4$ and concentrated. The residue was purified by chromatography on silica gel to give 1-(1-methyl-1H-tetrazol-5-yl)-1-phenyl-N-[(6-phenylpyridin-2-yl)methoxy]methanimine (0.192 g, 91% yield) as a colorless gum.

HPLC/MS: m/z=371 (M+H); $logP_{(HCOOH)}$=3.89

Preparation of 1-(1-methyl-1H-tetrazol-5-yl)-N-{[6-(pentylsulfanyl)pyridin-2-yl]methoxy}-1-phenylmethanimine (Compound 74) According to Process P5

To a solution of N-[(6-bromopyridin-2-yl)methoxy]-1-(1-methyl-1H-tetrazol-5-yl)-1-phenylmethanimine (0.3 g, 0.80 mmol, 1 eq.) in 2 ml of NMP were added 1-pentanethiol (0.084 g, 0.80 mmol, 1 eq.), $Cs_2CO_3$ (0.262 g, 0.80 mmol, 1 eq.). The reaction was microwaved (30 sec prestirring, abs-normal, fixed-hold) 120° C. for 60 s. Then a mixture water/EtOAc (1/1) was added and the aqueous layer was separated and extracted with EtOAc. The organics were combined, dried over $MgSO_4$ and concentrated. The residue was purified by chromatography on silica gel to give 1-(1-methyl-1H-tetrazol-5-yl)-N-{[6-(pentylsulfanyl)pyridin-2-yl]methoxy}-1-phenylmethanimine (0.058 g, 17% yield) as a viscous oil.

HPLC/MS: m/z=397 (M+H); $logP_{(HCOOH)}$=5.97

Preparation of 1-(1-methyl-1H-tetrazol-5-yl)-N-{[6-(pentylsulfanyl)pyridin-2-yl]methoxy}-1-phenyl-methanimine (Compound 20) According to Process P5

To a solution of N-[(6-bromopyridin-2-yl)methoxy]-1-(1-methyl-1H-tetrazol-5-yl)-1-phenylmethanimine (0.2 g, 0536 mmol, 1 eq.) in 3 ml of toluene were added hexanol (0.071 g, 0.697 mmol, 1.3 eq.), $Cs_2CO_3$ (0.227 g, 0.697 mmol, 1.3 eq.), $Pd(OAc)_2$ (0.002 g, 0.011 mmol, 0.02 eq.) and 2-(Di-t-butylphosphino)-1,1'-binapthyl (0.005 g, 0.013 mmol, 0.025 eq.). The vessel was purged with argon and sealed. The reaction was heated in microwave at 150° C. for 600 s (abs-normal fixed-hold) and diluted with 50 ml of EtOAc, filtered through a "celite" pad. The filtrate was evaporated and the residue was purified by chromatography on silica gel to give N-{6-(hexyloxy)pyridin-2-yl]methoxy}-1-(1-methyl-1H-tetrazol-5-yl)-1-phenylmethanimine (0.04 g, 17% yield) as a viscous pale brown oil.

HPLC/MS: m/z=395 (M+H); $logP_{(HCOOH)}$=5.39

Preparation of tert-butyl {6-[({[(1-methyl-1H-tetrazol-5-yl)(phenyl)methylene]amino}oxy)methyl]pyridin-2-yl}(pentyloxy)carbamate (Compound 268) According to Process P5

Step 1

Preparation of Tert-butyl(pentyloxy)carbamate

Tert-butyl hydroxycarbamate (2.1 g, 15.77 mmol, 1 eq.) was dissolved in MeCN and bromopentane (2.73 g, 18.13 mmol, 1.15 eq.) was added followed by DBU (2.52 g, 16.56 mmol, 1.05 eq.). The reaction was stirred at room temperature for 12 h and quenched with 0.1N HCl, extracted with EtOAc, dried over $MgSO_4$, and concentrated. The residue was purified by chromatography on silica gel to give tert-butyl(pentyloxy)carbamate (3.23 g, 91% yield) as a clear oil.

Step 2

Preparation of tert-butyl {6-[({[(1-methyl-1H-tetrazol-5-yl)(phenyl)methylene]amino}oxy)methyl]pyridin-2-yl}(pentyloxy)carbamate In a purged and dried vessel, N-[(6-bromopyridin-2-yl)methoxy]-1-(1-methyl-1H-tetrazol-5-yl)-1-phenylmethanimine (0.2 g, 0.536 mmol, 1 eq.) was dissolved in 3 ml of toluene and tert-butyl(pentyloxy)carbamate (0.217 g, 1.072 mmol 2 eq.) was added followed by $Pddba_2$ (0.065 g, 0.113 mmol, 0.21 eq.) and BINAP (0.069 g, 0.113 mmol, 0.21 eq.). Then tBuOK (0.12 g, 1.07 mmol, 2 eq.) was added and the vessel purged with argon and sealed. The reaction was stirred at 90° C. for 24 h. The solvent was evaporated and residue taken in EtOAc, filtered through "celite", washed with $H_2O$, dried over $MgSO_4$, and concentrated. The crude was purified by chromatography on silica gel to give tert-butyl {6-[({[(1-methyl-1H-tetrazol-5-yl)(phenyl)methylene]amino}oxy)methyl]pyridin-2-yl}(pentyloxy)carbamate (0.115 g, 41%) as a viscous yellow oil.

HPLC/MS: m/z=496 (M+H); $logP_{(HCOOH)}$=5.25

Preparation of 6-[({[(1-methyl-1H-tetrazol-5-yl)(phenyl)methylene]amino}oxy)methyl]-(pentyloxy) pyridin-2-amine (Compound 269) According to Process P6

Tert-butyl {6-[({[(1-methyl-1H-tetrazol-5-yl)(phenyl)methylene]amino}oxy)methyl]pyridin-2-yl}(pentyloxy)carbamate (0.211 g, 0.426 mmol, 1 eq.) was dissolved in 5 ml of DCM and TFA (0.485 g, 4.25 mmol, 10 eq.) was added. The reaction was stirred at room temperature overnight. Then $NaHCO_3$ was added and the reaction extracted with DCM. The organics were combined, dried over $MgSO_4$ and concentrated. The crude was purified by chromatography on silica gel to give 6-[({[(1-methyl-1H-tetrazol-5-yl)(phenyl)methylene]amino}oxy)methyl]-(pentyloxy)pyridin-2-amine (0.143 g, 80% yield) as a clear viscous oil.

HPLC/MS: m/z=396 (M+H); $logP_{(HCOOH)}$=3.87

Preparation of N-[(2-bromo-1,3-thiazol-4-yl)methoxy]-1-(1-methyl-1H-tetrazol-5-yl)-1-phenyl-methanimine (Compound 32) According to Process $P^a$ To a stirred suspension of 4-[({[(1-methyl-1H-tetrazol-5-yl)(phenyl)methylene]amino}oxy)methyl]-1,3-thiazol-2-amine (41 g, 130 mmol, 1 eq.) in 2000 ml of MeCN, were added sodium bromide (40.1 g, 390 mmol, 3 eq.), Copper (I) bromide (18.65 g, 130 mmol, 1 eq.) and t-Butylnitrite (16.38 g, 143 mmol, 1.1 eq.). The reaction was slowly heated to 80° C. for 1 h and allowed to cool. MeCN was evaporated and 500 ml water/1000 ml DCM were added to the residue. The crude was triturated, filtered through "celite" plug and washed with further 500 ml of EtOAc. The organic layers were combined, dried over $MgSO_4$, and evaporated to give N-[(2-bromo-1,3-thiazol-4-yl)methoxy]-1-(1-methyl-1H-tetrazol-5-yl)-1-phenylmethanimine (36 g, 69% yield, 10:1 mixture of stereoisomers) as a brown viscous oil.

HPLC/MS: m/z=379 (M+H); $logP_{(HCOOH)}$=3.11

Preparation of tert-butyl (2-cyclohexylethyl){6-[({[(1-methyl-1H-tetrazol-5-yl)(phenyl)methylene]amino}oxy)methyl]pyridin-2-yl}carbamate (Compound 141) According to Process P2

A stirred solution of tert-butyl {6-[({[(1-methyl-1H-tetrazol-5-yl)(phenyl)methylene]amino}oxy)methyl]pyridin-2-yl}carbamate (0.2 g, 0.488 mmol, 1 eq.) in 3 ml of dry DMF was treated with NaH (60% dispn in mineral oil, 0.020 g, 0.513 mmol, 1.05 eq.) added in one portion. After 20 mins (2-bromoethyl)cyclohexane (0.098 g, 0.513 mmol, 1.05 eq.) was added and the reaction was stirred for 1 hr. Water was added followed by EtOAc. The aqueous layer was separated and extracted with EtOAc. Then the organics were combined, dried over $MgSO_4$ and evaporated to give tert-butyl (2-cyclohexylethyl){6-[({[(1-methyl-1H-tetrazol-5-yl)(phenyl)methylene]amino}oxy)methyl]pyridin-2-yl}carbamate (0.27 g, 85%) as a viscous oil HPLC/MS: m/z=520 (M+H); $logP_{(HCOOH)}$=6.56

Preparation of N-(2-cyclohexylethyl)-6-[({[(1-methyl-1H-tetrazol-5-yl)(phenyl)methylene]amino}oxy)methyl]pyridin-2-amine (Compound 80) According to Process P6

To a stirred solution of tert-butyl (2-cyclohexylethyl){6-[({[(1-methyl-1H-tetrazol-5-yl)(phenyl)methylene]amino}oxy)methyl]pyridin-2-yl}carbamate (0.252 g, 0.413 mmol, 1 eq.) in 5 ml of dry DCM, was added TFA (1.41 g, 12.39 mmol, 30 eq.) in one portion. The reaction was refluxed for 5 hrs. Then the solvent and excess TFA were evaporated. The residue was neutralised with TEA and purified by chromatography on silica gel to give N-(2-cyclohexylethyl)-6-[({[(1-methyl-1H-tetrazol-5-yl)(phenyl)methylene]amino}oxy)methyl]pyridin-2-amine (0.138 g, 76% yield) as a viscous oil.

HPLC/MS: m/z=420 (M+H); $logP_{(HCOOH)}$=3.35

Preparation of N-(2-cyclohexylethyl)-4-[({[(1-methyl-1H-tetrazol-5-yl)(phenyl)methylene]amino}oxy)methyl]-1,3-thiazol-2-amine (Compound 161) According to Process P5 Concatenated with Process P6

A stirred solution of tert-butyl {4-[({[(1-methyl-1H-tetrazol-5-yl)(phenyl)methylene]amino}oxy)methyl]-1,3-thiazol-2-yl}carbamate (0.185 g, 0.445 mmol, 1 eq.) in 3 ml of dry DMF was treated with NaH (60% dispn in mineral oil, 0.019 g, 0.49 mmol, 1.1 eq.) added in one portion. After 20 mins (2-bromoethyl)cyclohexane (0.096 g, 0.49 mmol, 1.1 eq.) was added and the reaction was stirred for 1 hr. Then TFA (1.48 g, 12.98 mmol, 30 eq.) was added carefully and the reaction was heated to 60° C. for 12 h. After cooling, sat. aqueous $Na_2CO_3$ was added followed by DCM. The layers were separated and the aqueous layer was extracted with DCM. The organics were combined, washed with sat. aqueous $Na_2CO_3$, dried over $MgSO_4$ and concentrated. The crude was purified by chromatography on silica gel to give N-(2-cyclohexylethyl)-4-[({[(1-methyl-1H-tetrazol-5-yl)(phenyl)methylene]amino}oxy)methyl]-1,3-thiazol-2-amine (0.144 g, 76% yield) as a clear viscous oil.

HPLC/MS: m/z=426 (M+H); $logP_{(HCOOH)}$=3.62

Preparation of 1-{6-[({[(1-methyl-1H-tetrazol-5-yl)(phenyl)methylene]amino}oxy)methyl]pyridin-2-yl}methanamine (Compound 52)

Step 1

To a solution of 2,6-bis(chloromethyl)pyridine (20 g, 113.6 mmol, 1 eq.) in 250 ml of DMF was added potassium phthalimide (21.04 g, 113.6 mmol, 1 eq.). The reaction was stirred at r.t. overnight then the solvent was evaporated and the residue taken in EtOAc. The insolubles were removed by filtration and the filtrate washed with $H_2O$. The organic layer was separated, dried over $MgSO_4$ and concentrated. The resulting white solid was recrystallised from IPE/EtOAc (1/1) to give 2-{[6-(chloromethyl)pyridin-2-yl]methyl}-1H-isoindole-1,3(2H)-dione (22.34 g, 68% yield) as a white solid.

HPLC/MS: m/z=287 (M+H); $logP_{(HCOOH)}$=2.51

Step 2

To a stirred solution of N-hydroxy-1-(5-methyl-1H-tetrazol-1-yl)-1-phenylmethanimine (1.5 g, 7.38 mmol, 1.0 eq.) in 25 ml of MeCN was added $Cs_2CO_3$ (2.40 g, 7.38 mmol, 1 eq.) followed by KI (0.122 g, 0.738 mmol, 0.1 eq.) in one portion. The resulting suspension was stirred for 5 mins before addition of 2-{[6-(chloromethyl)pyridin-2-yl]methyl}-1H-isoindole-1,3(2H)-dione (2.11 g, 7.38 mmol, 1 eq.) in one portion. The reaction was stirred for 24 hrs at room temperature. The solvent was evaporated then the residue was dissolved in EtOAc and washed with $H_2O$. The organic layer was separated, dried over $MgSO_4$ and concentrated. The residue was purified by chromatography on silica gel to give 2-({6-[({[(1-methyl-1H-tetrazol-5-yl)(phenyl)methylene]amino}oxy)methyl]pyridin-2-yl}methyl)-1H-isoindole-1,3(2H)-dione (3 g, 90% yield) as a white foam.

HPLC/MS: m/z=454 (M+H); $logP_{(HCOOH)}$=3.19

Step 3

To a solution of 2-({6-[({[(1-methyl-1H-tetrazol-5-yl)(phenyl)methylene]amino}oxy)methyl]pyridin-2-yl}methyl)-1H-isoindole-1,3(2H)-dione (3 g, 6.61 mmol, 1 eq.) in 25 ml of THF was added hydrazine hydrate (1.32 g, 26.46 mmol, 4 eq.). The reaction was stirred overnight at room temperature. The solvent was evaporated and the residue dissolved in EtOAc. Water was added and the layers separated. The aqueous layer was extracted with EtOAc and the organics were combined, dried over $MgSO_4$ and concentrated to give 1-{6-[({[(1-methyl-1H-tetrazol-5-yl)(phenyl)methylene]amino}oxy)methyl]pyridin-2-yl}methanamine (2.29 g, 93%) as a clear viscous oil.

HPLC/MS: m/z=324 (M+H); $logP_{(HCOOH)}$=1.23

Preparation of N-({6-[({[(1-methyl-1H-tetrazol-5-yl)(phenyl)methylene]amino}oxy)methyl]pyridin-2-yl}methyl)hexanamide (Compound 53)

To a solution of 1-{6-[({[(1-methyl-1H-tetrazol-5-yl)(phenyl)methylene]amino}oxy)methyl]pyridin-2-yl}methanamine (0.21 g, 0.649 mmol, 1 eq.) in 2 ml of DCM was added TEA (0.197 g, 1.94 mmol, 3 eq.) followed by hexanoyl chloride (0.131 g, 0.974 mmol, 1.5 eq.). The reaction was stirred 4 h at room temperature and the solvent was evaporated. The crude was purified by chromatography on silica gel to give N-({6-[({[(1-methyl-1H-tetrazol-5-yl)(phenyl)methylene]amino}oxy)methyl]pyridin-2-yl}methyl)hexanamide (0.182 g, 62% yield) as a white solid.

HPLC/MS: m/z=422 (M+H); $logP_{(HCOOH)}$=2.88

Preparation of N-{[6-(1,3-dioxolan-2-yl)pyridin-2-yl]methoxy}-1-(1-methyl-1H-tetrazol-5-yl)-1-phenylmethanimine (Compound 160)

Step 1

Preparation of 2-(1,3-dioxolan-2-yl)-6-methylpyridine

To a solution of 6-methylpyridine-2-carbaldehyde (3.7 g, 30.54 mmol, 1 eq.) in 10 ml of ethylene glycol was added $TsOH.H_2O$ (6.67 g, 32.07 mmol, 1.05 eq.). The reaction was heated in microwave at 200° C. for 180 s (fixed hold absorb high). The mixture was added to a stirred solution of 10 g of $K_2CO_3$ in 200 ml of water, and was extracted with DCM (3×150 ml). The combined organics were washed with water evaporated on RFE (water bath 25° C.) to give 2-(1,3-dioxolan-2-yl)-6-methylpyridine (3.7 g, 51% yield) as pale brown liquid.

HPLC/MS: m/z=166 (M+H); $logP_{(HCOOH)}$=1.21

Step 2

Preparation of 2-(1,3-dioxolan-2-yl)-6-methylpyridine 1-oxide

To a solution 2-(1,3-dioxolan-2-yl)-6-methylpyridine (3.7 g, 15.67 mmol, 1 eq.) in 200 ml of DCM was added mCPBA (7.21 g, 31.35 mmol, 2 eq.) portionwise (exotherm 20° C.>26° C.). The reaction was stirred for 1 hr and 100 ml of 2M aqueous $K_2CO_3$ solution was added. The mixture was stirred for 15 mins and the organic layer was separated, washed with water (100 ml), dried over $MgSO_4$ and evaporated to give 2-(1,3-dioxolan-2-yl)-6-methylpyridine 1-oxide (2.4 g, 80% yield) as a yellow liquid.

HPLC/MS: m/z=182 (M+H); $logP_{(HCOOH)}$=0.45

Step 3

Preparation of [6-(1,3-dioxolan-2-yl)pyridin-2-yl]methanol

To a stirred solution of 2-(1,3-dioxolan-2-yl)-6-methylpyridine 1-oxide (2.3 g, 12.69 mmol, 1 eq.) in 200 ml dry DCM was added TFA (6.66 g, 31.73 mmol, 2.5 eq.) via syringe, The reaction was stirred 2 hrs and was evaporated on RFE. The residue was redissolved in 200 ml DCM and 200 ml of 2M aqueous $K_2CO_3$ solution was added. Vigorously stirring was allowed for 2 hrs. The aqueous layer was separated and extracted with fresh DCM (2×100 ml). The organics were combined, washed with water (50 ml), brine (50 ml), dried over $MgSO_4$ and concentrated to give [6-(1,3-dioxolan-2-yl)pyridin-2-yl]methanol (2.25 g, 84% yield) as a yellow oil.

HPLC/MS: m/z=182 (M+H); $logP_{(HCOOH)}$=0.54

Step 4

Preparation of 1-{[6-(1,3-dioxolan-2-yl)pyridin-2-yl]methyl}pyridinium bromide hydrobromide To a stirred solution thionyl bromide (8.36 g, 40.23 mmol, 1 eq.) in 300 ml dry DCM, cooled to 5° C., was added dropwise a solution of [6-(1,3-dioxolan-2-yl)pyridin-2-yl]methanol (8.1 g, 40.23 mmol, 1 eq.) and pyridine (3.18 g, 40.23 mmol, 1 eq.) in 15 ml dry DCM. On complete addition, the cooling bath was removed, the reaction warmed to room temperature and stirred overnight. 150 ml of water and 150 ml of DCM were added and stirring allowed for 2 mins. The organic layer was separated, dried over $MgSO_4$ and concentrated to give 1-{[6-(1,3-dioxolan-2-yl)pyridin-2-yl]methyl}pyridinium bromide hydrobromide (15.7 g, 96% yield) as a white solid.

Step 5

Preparation of N-{[6-(1,3-dioxolan-2-yl)pyridin-2-yl]methoxy}-1-(1-methyl-1H-tetrazol-5-yl)-1-phenylmethanimine To a cooled (0° C.) stirred solution of N-hydroxy-1-(1-methyl-1H-tetrazol-5-yl)-1-phenylmethanimine (12.2 g, 60.03 mmol, 1.0 eq.) in 250 ml of MeCN, was added dropwise DBN (12.30 g, 99.06 mmol, 1.65 eq.). The reaction was stirred for 5 mins before addition of 1-{[6-(1,3-dioxolan-2-yl)pyridin-2-yl]methyl}pyridinium bromide hydrobromide (15.7 g, 39.02 mmol, 0.65 eq.) portionwise. The mixture was stirred for further 5 mins before removal of the cooling bath and continued at ambient temperature. MeCN was evaporated and the residue dissolved in 500 ml of DCM, washed with water (×2), dried over $MgSO_4$ and concentrated. The residue was purified by chromatography on silica gel to yield N-{[6-(1,3-dioxolan-2-yl)pyridin-2-yl]methoxy}-1-(1-methyl-1H-tetrazol-5-yl)-1-phenylmethanimine (5 g, 22% yield) as a pale yellow oil.

HPLC/MS: m/z=367 (M+H); $logP_{(HCOOH)}$=2.47

Preparation of N-{[6-(1,3-dioxolan-2-yl)pyridin-2-yl]methoxy}-1-(1-methyl-1H-tetrazol-5-yl)-1-phenylmethanimine (Compound 174)

To a solution of N-{[6-(1,3-dioxolan-2-yl)pyridin-2-yl]methoxy}-1-(1-methyl-1H-tetrazol-5-yl)-1-phenylmethanimine (3.3 g, 9 mmol, 1 eq.) in 75 ml of DMSO and 15 ml of water was added p-TSA (1.79 g, 9.45 mmol, 1.05 eq.). The reaction was heated to 100° C. for 1.5 hrs. After cooling to room temperature, the mixture was diluted with 400 ml of EtOAc, washed with sat. aqueous $NaHCO_3$, followed by water (×2). The organic layer was separated, dried over $MgSO_4$ and concentrated to give 6-[({[(1-methyl-1H-tetrazol-5-yl)(phenyl)methylene]amino}oxy)methyl]pyridine-2-carbaldehyde (3.1 g, 96% yield) as a viscous yellow oil.

HPLC/MS: m/z=323 (M+H); $logP_{(HCOOH)}$=2.54

Preparation of N-({6-[(hydroxyimino)methyl]pyridin-2-yl}methoxy)-1-(1-methyl-1H-tetrazol-5-yl)-1-phenylmethanimine (Compound 177)

To a solution of 6-[({[(1-methyl-1H-tetrazol-5-yl)(phenyl)methylene]amino}oxy)methyl]pyridine-2-carbaldehyde (1.8 g, 5.58 mmol, 1 eq.) in 10 ml of pyridine was added hydroxylamine hydrochloride 0.427 g, 6.14 mmol, 1.1 eq.). The reaction was stirred for 6 hrs and stood overnight. The pyridine was evaporated, and the residue was partitioned between EtOAc and water. The organic layer was separated, dried over MgSO4 and concentrated to give N-({6-[(hydroxyimino)methyl]pyridin-2-yl}methoxy)-1-(1-methyl-1H-tetrazol-5-yl)-1-phenylmethanimine (1.66 g, 88% yield) as a pale brown solid.

HPLC/MS: m/z=338 (M+H); $logP_{(HCOOH)}$=2.16

Preparation of {6-[({[(1-methyl-1H-tetrazol-5-yl)(phenyl)methylene]amino}oxy)methyl]pyridin-2-yl}methanol (Compound 275)

To a stirred solution of 6-[({[(1-methyl-1H-tetrazol-5-yl)(phenyl)methylene]amino}oxy)methyl]pyridine-2-carbaldehyde (0.4 g, 1.24 mmol, 1 eq.) in 100 ml of dry THF, was added sodium triacetoxyborohydride (0.276 mmol, 1.3 mmol, 1.05 eq.) in one portion. The reaction was stirred for 20 hrs, before the addition of 1M aqueous NaOH (100 ml). The mixture was stirred for 15 mins before extraction with EtOAc. The organic phase was dried over MgSO4 and evaporated. The residue was purified by chromatography on silica gel to give {6-[({[(1-methyl-1H-tetrazol-5-yl)(phenyl)methylene]amino}oxy)methyl]pyridin-2-yl}methanol (0.2 g, 47% yield) as a colourless gum.

HPLC/MS: m/z=325 (M+H); $logP_{(HCOOH)}$=1.76

Preparation of N-[(6-{[(cyclohexyloxy)imino]methyl}pyridin-2-yl)methoxy]-1-(1-methyl-1H-tetrazol-5-yl)-1-phenylmethanimine (Compound 274)

To a stirred solution of N-({6-[(hydroxyimino)methyl]pyridin-2-yl}methoxy)-1-(1-methyl-1H-tetrazol-5-yl)-1-phenylmethanimine (0.2 g, 0.593 mmol, 1 eq.) in 2.5 ml of dry DMF, was added NaH (0.024 g, 0.623 mmol, 1.05 eq.) in one portion. After 10 mins, 1-iodocyclohexane (0.130 g, 0.623 mmol, 1.05 eq.) was added rapid dropwise. Stirring was continued for 20 hrs and warmed at 45° C. for 4 hrs. "brine" was added and the reaction was extracted with EtOAc (2×75 ml). The combined organic layers were washed with water (2×), dried over $MgSO_4$ and evaporated. The residue was purified by chromatography on silica gel to give N-[(6-{[(cyclohexyloxy)imino]methyl}pyridin-2-yl)methoxy]-1-(1-methyl-1H-tetrazol-5-yl)-1-phenylmethanimine (0.107 g, 41% yield) as a colourless viscous oil.

HPLC/MS: m/z=420 (M+H); $logP_{(HCOOH)}$=4.89

Preparation of N-hexyl-6-{[({[3-(methylsulfanyl)
phenyl](1-methyl-1H-tetrazol-5-yl)
methylene}amino)oxy]methyl}pyridin-2-amine
(Compound 297) According to Process P7

Step 1

Preparation of
N-methoxy-N-methyl-3-(methylsulfanyl)benzamide

To a stirred solution of 3-(methylthio)benzoic acid (15.4 g, 91.5 mmol), cooled to 0° C. with a brine/ice bath, was added N,N-dimethylformamide (0.35 mL, 4.6 mmol) followed by oxalyl chloride (8.79 mL, 100 mmol). The resulting mixture was stirred 2 h at room temperature, until gas evolution stopped and a clear solution was obtained. The mixture was cooled to 0° C. with a brine/ice bath, N,O-Dimethylhydroxylamine (10.7 g, 110 mmol) was added at once, followed by dropwise addition of triethylamine (43.4 mL, 311 mmol) through a dropping funnel, while keeping the internal temperature under 20° C. The resulting suspension was stirred overnight at room temperature, filtered over a pad of silica gel, and concentrated in vacuo to afford N-methoxy-N-methyl-3-(methylsulfanyl)benzamide as an oil [19.9 g, yield 83%; HPLC/MS: m/z=212 (M+H); $\log P_{(HCOOH)}$=1.89].

Step 2

Preparation of [3-(methylsulfanyl)phenyl](1-methyl-1H-tetrazol-5-yl)methanone

To a stirred solution of 1-methyl-1H-tetrazole (4.20 g, 50 mmol) in anhydrous THF (200 mL), cooled to 0° C. with a brine/ice bath, was added dropwise a solution of isopropylmagnesium chloride (2 M in THF, 30 mL, 60.2 mmol). After the addition was over, the resulting cloudy suspension was stirred for 15 min at 0° C. A solution of N-methoxy-N-methyl-3-(methylsulfanyl)benzamide (10.2 g, 39 mmol) in THF (80 mL) was then added dropwise while keeping the internal temperature below 5° C. The reaction mixture was then allowed to warm up and stirred overnight at room temperature. Aq. HCl (1 M, 65 mL) was added to the reaction mixture, the layers were separated, the water phase was extracted with ethyl acetate (3×50 mL) and the combined organic layers were dried over MgSO$_4$. Purification on silica gel afforded [3-(methylsulfanyl)phenyl](1-methyl-1H-tetrazol-5-yl)methanone as a yellow solid [5.95 g, yield 43%; HPLC/MS: m/z=235 (M+H); $\log P_{(HCOOH)}$=2.52].

Step 3

Preparation of N-hydroxy-1-[3-(methylsulfanyl)phenyl]-1-(1-methyl-1H-tetrazol-5-yl)methanimine To a stirred solution of [3-(methylsulfanyl)phenyl](1-methyl-1H-tetrazol-5-yl)methanone (5.62 g, 24 mmol) in dry pyridine (30 mL) was added hydroxylamine hydrochloride (4.17 g, 60 mmol). The reaction mixture was stirred at 70° C. for 5 h, then concentrated in vacuo and diluted with ethyl acetate (100 mL) and water (50 mL). The organic layer was separated, washed with water (50 mL) and dried over MgSO$_4$. Evaporation of the solvent in vacuo afforded N-hydroxy-1-[3-(methylsulfanyl)phenyl]-1-(1-methyl-1H-tetrazol-5-yl)methanimine as a yellow solid [6.91 g, yield 99.3%; HPLC/MS: m/z=250 (M+H); $\log P_{(HCOOH)}$=1.98].

Step 4

Preparation of 2-(6-{[({[3-(methylsulfanyl)phenyl]
(1-methyl-1H-tetrazol-5-yl)methylene}amino)oxy]
methyl}pyridin-2-yl)-1H-isoindole-1,3(2H)-dione To a stirred solution of N-hydroxy-1-[3-(methylsulfanyl)phenyl]-1-(1-methyl-1H-tetrazol-5-yl)methanimine (3.00 g, 10.3 mmol) in dry acetone (80 mL) were added 2-[6-(bromomethyl)pyridin-2-yl]-1H-isoindole-1,3(2H)-dione (3.61 g, 11.4 mmol), cesium carbonate (7.08 g, 21.7 mmol) and potassium iodide (0.17 g, 1.04 mmol). The reaction mixture was stirred at room temperature for 5 h, then insolubles were removed by filtration and washed with dichloromethane. The filtrates were combined and concentrated in vacuo. The residue was dissolved in dichloromethane (500 mL), washed with water (2×200 mL), and the organic layer was dried over MgSO$_4$ and concentrated in vacuo to afford 3-(6-{[({[3-(methylsulfanyl)phenyl](1-methyl-1H-tetrazol-5-yl)
methylene}amino)oxy]methyl}pyridin-2-yl)-1H-isoindole-1,3(2H)-dione as a yellow solid [2.79 g, yield 56%; HPLC/MS: m/z=486 (M+H); $\log P_{(HCOOH)}$=3.39].

Step 5

Preparation of 6-{[({[3-(methylsulfanyl)phenyl](1-methyl-1H-tetrazol-5-yl)methylene}amino)oxy]
methyl}pyridin-2-amine According to Process P6

To a stirred solution of 2-(6-{[({[3-(methylsulfanyl)phenyl](1-methyl-1H-tetrazol-5-yl)methylene}amino)oxy]
methyl}pyridin-2-yl)-1H-isoindole-1,3(2H)-dione (2.79 g, 5.75 mmol) in dry THF (70 mL) was added hydrazine hydrate (1.44 g, 28.7 mmol). The reaction mixture was stirred at room temperature for 4 h, then insolubles were removed by filtration and washed with dichloromethane. The filtrates were combined and concentrated in vacuo. The residue was dissolved in dichloromethane (100 mL), washed with water (50 mL), and the organic layer was dried over MgSO$_4$ and concentrated in vacuo to afford 6-{[({[3-(methylsulfanyl)phenyl](1-methyl-1H-tetrazol-5-yl)methylene}amino)oxy]
methyl}pyridin-2-amine as a white solid [1.63 g, yield 77%; HPLC/MS: m/z=356 (M+H); $\log P_{(HCOOH)}$=1.42].

Step 6

Preparation of N-hexyl-6-{[({[3-(methylsulfanyl)
phenyl](1-methyl-1H-tetrazol-5-yl)
methylene}amino)oxy]methyl}pyridin-2-amine
(Compound 297) According to Process P7

To a stirred solution of 6-{[({[3-(methylsulfanyl)phenyl]
(1-methyl-1H-tetrazol-5-yl)methylene}amino)oxy]
methyl}pyridin-2-amine (134 mg, 0.38 mmol) in dry dichloromethane (5 mL) were added capronaldehyde (52.9 mg, 0.53 mmol) and sodium triacetoxyborohydride (151 mg, 0.68 mmol) at room temperature. After stirring at room temperature for 20 h, the reaction mixture was diluted with dichloromethane (10 mL) and aq. NaHCO$_3$ (10 g/L, 10 mL) was added. After phase separation, the organic layer was washed with water, dried over MgSO$_4$ and concentrated in vacuo. Purification on silica gel afforded N-hexyl-6-{[({[3-(methylsulfanyl)phenyl](1-methyl-1H-tetrazol-5-yl)
methylene}amino)oxy]methyl}pyridin-2-amine as a colourless oil [115 mg, yield 69%; HPLC/MS: m/z=440 (M+H); $\log P_{(HCOOH)}$=2.78].

Preparation of 4-{[({[3-(methylsulfanyl)phenyl](1-methyl-1H-tetrazol-5-yl)methylene}amino)oxy]methyl}-N-(3-phenylpropyl)-1,3-thiazol-2-amine (Compound 312)

Step 1

Preparation of 4-{[({[3-(methylsulfanyl)phenyl](1-methyl-1H-tetrazol-5-yl)methylene}amino)oxy]methyl}-1,3-thiazol-2-amine To a stirred suspension of N-hydroxy-1-[3-(methylsulfanyl)phenyl]-1-(1-methyl-1H-tetrazol-5-yl)methanimine (2.00 g, 6.90 mmol), in dry acetonitrile (115 mL) were added 4-(chloromethyl)-1,3-thiazol-2-amine (1.13 g, 7.59 mmol), cesium carbonate (4.72 g, 14.5 mmol) and potassium iodide (0.57 g, 3.45 mmol). The reaction mixture was stirred at room temperature for 26 h, then insolubles were removed by filtration and washed with dichloromethane (3×40 mL) and ethyl acetate (3×40 mL). The filtrates were combined and concentrated in vacuo. The residue was dissolved in dichloromethane (100 mL), washed with water (50 mL), the aqueous layer was extracted with dichloromethane (50 mL) and the combined organic layers were dried over $MgSO_4$ and concentrated in vacuo to afford 4-{[({[3-(methylsulfanyl)phenyl](1-methyl-1H-tetrazol-5-yl)methylene}amino)oxy]methyl}-1,3-thiazol-2-amine [1.10 g, yield 42%; HPLC/MS: m/z=362 (M+H); $logP_{(HCOOH)}$=1.76].

Preparation of 4-{[({[3-(methylsulfanyl)phenyl](1-methyl-1H-tetrazol-5-yl)methylene}amino)oxy]methyl}-N-(3-phenylpropyl)-1,3-thiazol-2-amine (Compound 312) According to Process P7

To a stirred solution of 4-{[({[3-(methylsulfanyl)phenyl](1-methyl-1H-tetrazol-5-yl)methylene}amino)oxy]methyl}-1,3-thiazol-2-amine (90.0 mg, 0.25 mmol) in dry 1,2-dichloroethane (5 mL), under argon atmosphere, were added 3-phenylpropionaldehyde (63.5 mg, 0.47 mmol), acetic acid (89.7 mg, 1.49 mmol) and sodium triacetoxyborohydride (156 mg, 0.70 mmol) at room temperature. After stirring at room temperature for 18 h, 3-phenylpropionaldehyde (63.5 mg, 0.47 mmol), acetic acid (89.7 mg, 1.49 mmol) and sodium triacetoxyborohydride (156 mg, 0.70 mmol) were added again and the reaction mixture was further stirred at room temperature for 20 h. The reaction mixture was diluted with dichloromethane (10 mL) and sat. aq. $NaHCO_3$ (10 mL) was added. After phase separation, the aqueous layer was washed with ethyl acetate (3×10 mL), the combined organic layers were washed with water (10 mL), dried over $MgSO_4$ and concentrated in vacuo. Purification on silica gel afforded 4-{[({[3-(methylsulfanyl)phenyl](1-methyl-1H-tetrazol-5-yl)methylene}amino)oxy]methyl}-N-(3-phenylpropyl)-1,3-thiazol-2-amine as a pale yellow oil [69 mg, yield 58%; HPLC/MS m/z=481 (M+H); $logP_{(HCOOH)}$=3.71].

Preparation of N-[(2-bromo-1,3-thiazol-4-yl)methoxy]-1-[3-(methylsulfanyl)phenyl]-1-(1-methyl-1H-tetrazol-5-yl)methanimine (Compound 302) According to Process P1

To a stirred solution of N-hydroxy-1-[3-(methylsulfanyl)phenyl]-1-(1-methyl-1H-tetrazol-5-yl)methanimine (1.00 g, 3.73 mmol) in acetonitrile (60 mL), were added cesium carbonate (2.55 g, 7.83 mmol), potassium iodide (310 mg, 1.86 mmol) and 2-bromo-4-bromomethyl-thiazole (1.05 g, 4.10 mmol). The resulting suspension was stirred at 25° C. for 6 h.

The suspension was filtered, the solids washed with ethyl acetate and dichloromethane and the filtrate was concentrated in vacuo. The residue was dissolved in dichloromethane (50 mL), washed with water, dried over $MgSO_4$ concentrated in vacuo. Purification on silica gel afforded N-[(2-bromo-1,3-thiazol-4-yl)methoxy]-1-[3-(methylsulfanyl)phenyl]-1-(1-methyl-1H-tetrazol-5-yl)methanimine as an oil that solidified on standing after 2 days [1.49 g, yield 94%; HPLC/MS: m/z=425 (M+H); $logP_{(HCOOH)}$=3.55].

Preparation of N-{[2-(cyclopropylethynyl)-1,3-thiazol-4-yl]methoxy}-1-[3-(methyl-sulfanyl)phenyl]-1-(1-methyl-1H-tetrazol-5-yl)methanimine (Compound 310) According to Process P5

A solution of N-[(2-bromo-1,3-thiazol-4-yl)methoxy]-1-[3-(methylsulfanyl)phenyl]-1-(1-methyl-1H-tetrazol-5-yl)methanimine (150 mg, 0.35 mmol), cyclopropylacetylene (8.44 M in toluene, 84 µL, 0.70 mmol), copper(I) iodide (6.72 mg, 0.03 mmol), tetrakis(triphenylphosphine)palladium(0) (20.4 mg, 0.05 mmol), N,N-dicyclohexylmethylamine (0.30 mL, 1.41 mmol) in degassed tetrahydrofuran (3 mL) was stirred under an Argon atmosphere at room temperature for 24 h. After evaporation of the solvent in vacuo, purification on silica gel afforded N-{[2-(cyclopropylethynyl)-1,3-thiazol-4-yl]methoxy}-1-[3-(methyl-sulfanyl)phenyl]-1-(1-methyl-1H-tetrazol-5-yl)methanimine as a thick oil [116 mg, yield 80%; HPLC/MS: m/z=411 (M+H); $logP_{(HCOOH)}$=3.99].

Preparation of 6-{[({[3-(dimethylamino)phenyl](1-methyl-1H-tetrazol-5-yl)methylene}amino)oxy]methyl}-N-(3-phenylpropyl)pyridin-2-amine (Compound 311)

Step 1

Preparation of 3-(dimethylamino)-N-methoxy-N-methylbenzamide

To a stirred solution of 3-(dimethylamino)benzoic acid (16.5 g, 100 mmol), cooled to 0° C. with a brine/ice bath, was added N,N-dimethylformamide (0.39 mL, 5 mmol) followed by oxalyl chloride (10.5 mL, 120 mmol). The resulting mixture was stirred 4 h at room temperature, until gas evolution stopped and a clear solution was obtained. The mixture was cooled to 0° C. with a brine/ice bath, N,O-Dimethylhydroxylamine (13.7 g, 140 mmol) was added at once, followed by dropwise addition of triethylamine (55.8 mL, 400 mmol) through a dropping funnel, while keeping the internal temperature under 20° C. The resulting suspension was stirred overnight at room temperature, then washed with brine. The aqueous layers were extracted with dichloromethane (2×50 mL), then the combined organic layers were dried over $MgSO_4$ and concentrated in vacuo to afford 3-(dimethylamino)-N-methoxy-N-methylbenzamide as an oil [15.5 g, yield 67%; HPLC/MS: m/z=209 (M+H); $logP_{(HCOOH)}$=0.95].

Step 2

Preparation of [3-(dimethylamino)phenyl](1-methyl-1H-tetrazol-5-yl)methanone

To a stirred solution of 1-methyl-1H-tetrazole (4.54 g, 54 mmol) in anhydrous THF (200 mL), cooled to 0° C. with a brine/ice bath, was added dropwise a solution of isopropylmagnesium chloride (2 M in THF, 27 mL, 54 mmol). After the addition was over, the resulting cloudy suspension was stirred for 15 min at 0° C. A solution of 3-(dimethylamino)-N-methoxy-N-methylbenzamide (9.37 g, 45 mmol) in THF (80 mL) was then added dropwise while keeping the internal temperature below 5° C. The reaction mixture was then allowed to warm up and stirred at room temperature for 1 h. A mixture of ice-cold water (50 mL) and aq. HCl (1 M, 55 mL) was added to the reaction mixture, the layers were separated, the water phase was extracted with ethyl acetate (3×50 mL) and the combined organic layers were dried. Purification on silica gel followed by recrystallization from diethyl ether afforded [3-(dimethylamino)phenyl](1-methyl-1H-tetrazol-5-yl)methanone as a bright yellow solid [3.06 g, yield 25%; HPLC/MS m/z=232 (M+H); $logP_{(HCOOH)}$=2.21].

Step 3

Preparation of 3-[(hydroxyimino)(1-methyl-1H-tetrazol-5-yl)methyl]-N,N-dimethylaniline To a stirred solution of [3-(dimethylamino)phenyl](1-methyl-1H-tetrazol-5-yl)methanone (3.84 g, 17 mmol) in dry pyridine (30 mL) was added hydroxylamine hydrochloride (2.89 g, 42 mmol). The reaction mixture was stirred at 70° C. for 6 h, then concentrated in vacuo and diluted with ethyl acetate (100 mL) and water (50 mL). The organic layer was separated, washed with water (50 mL) and dried over $MgSO_4$. Evaporation of the solvent in vacuo afforded 3-[(hydroxyimino)(1-methyl-1H-tetrazol-5-yl)methyl]-N,N-dimethylaniline as a yellow solid [4.48 g, yield 99.6%; HPLC/MS m/z=247 (M+H); $logP_{(HCOOH)}$=1.17].

Step 4

Preparation of 2-(6-{[({[3-(dimethylamino)phenyl](1-methyl-1H-tetrazol-5-yl)methylene}amino)oxy]methyl}pyridin-2-yl)-1H-isoindole-1,3(2H)-dione According to Process P1

To a stirred solution of 3-[(hydroxyimino)(1-methyl-1H-tetrazol-5-yl)methyl]-N,N-dimethylaniline (2.90 g, 11 mmol) in dry acetonitrile (100 mL) were added 2-[6-(bromomethyl)pyridin-2-yl]-1H-isoindole-1,3(2H)-dione (3.74 g, 11.8 mmol), cesium carbonate (7.33 g, 22.5 mmol) and potassium iodide (0.89 g, 5.36 mmol). The reaction mixture was stirred at room temperature for 24 h, then insolubles were removed by filtration and washed with dichloromethane. The filtrates were combined and concentrated in vacuo. The residue was dissolved in dichloromethane (500 mL), washed with water (2×200 mL), and the organic layer was dried over $MgSO_4$ and concentrated in vacuo to afford 2-(6-{[({[3-(dimethylamino)phenyl](1-methyl-1H-tetrazol-5-yl)methylene}amino)oxy]methyl}pyridin-2-yl)-1H-isoindole-1,3(2H)-dione as an orange solid [5.28 g, yield 97%; HPLC/MS: m/z=483 (M+H); $logP_{(HCOOH)}$=3.17].

Step 5

Preparation of 6-{[({[3-(dimethylamino)phenyl](1-methyl-1H-tetrazol-5-yl)methylene}amino)oxy]methyl}pyridin-2-amine According to Process P6

To a stirred solution of 2-(6-{[({[3-(dimethylamino)phenyl](1-methyl-1H-tetrazol-5-yl)methylene}amino)oxy]methyl}pyridin-2-yl)-1H-isoindole-1,3(2H)-dione (5.22 g, 11 mmol) in dry THF (130 mL) was added hydrazine hydrate (2.63 mL, 54 mmol). The reaction mixture was stirred at room temperature for 6 h, then insolubles were removed by filtration and washed with ethyl acetate. The filtrates were combined and concentrated in vacuo. The residue was dissolved in ethyl acetate (250 mL), washed with water (2×100 mL), and the organic layer was dried over $MgSO_4$ and concentrated in vacuo to afford 6-{[({[3-(dimethylamino)phenyl](1-methyl-1H-tetrazol-5-yl)methylene}amino)oxy]methyl}pyridin-2-amine as an orange solid [3.56 g, yield 89%; HPLC/MS: m/z=353 (M+H); $logP_{(HCOOH)}$=1.19].

Step 6

Preparation of 6-{[({[3-(dimethylamino)phenyl](1-methyl-1H-tetrazol-5-yl)methylene}amino)oxy]methyl}-N-(3-phenylpropyl)pyridin-2-amine (Compound 311) According to Process P7

To a stirred solution of 6-{[({[3-(dimethylamino)phenyl](1-methyl-1H-tetrazol-5-yl)methylene}amino)oxy]methyl}pyridin-2-amine (125.0 mg, 0.35 mmol) in dry 1,2-dichloroethane (10 mL), under argon atmosphere, were added 3-phenylpropionaldehyde (66.6 mg, 0.49 mmol) and sodium triacetoxyborohydride (135 mg, 0.63 mmol) at room temperature. After stirring at room temperature for 18 h, the reaction mixture was diluted with dichloromethane (50 mL) and aq. NaOH (1 M, 30 mL) was added. After phase separation, the organic layer was washed with water (40 mL), dried over $MgSO_4$ and concentrated in vacuo. Purification on silica gel afforded 6-{[({[3-(dimethylamino)phenyl](1-methyl-1H-tetrazol-5-yl)methylene}amino)oxy]methyl}-N-(3-phenylpropyl)pyridin-2-amine as an oil [82 mg, yield 47%; HPLC/MS: m/z=471 (M+H); $logP_{(HCOOH)}$=2.57].

Preparation of 3-[{[(2-bromo-1,3-thiazol-4-yl)methoxy]imino}(1-methyl-1H-tetrazol-5-yl)methyl]-N,N-dimethylaniline (Compound 312) According to Process P1

To a stirred solution of 3-[(hydroxyimino)(1-methyl-1H-tetrazol-5-yl)methyl]-N,N-dimethylaniline (1.25 g, 5.07 mmol) in acetonitrile (50 mL), were added cesium carbonate (3.47 g, 10.6 mmol), potassium iodide (421 mg, 2.53 mmol) and 2-bromo-4-bromomethyl-thiazole (1.44 g, 5.58 mmol). The resulting suspension was stirred at 25° C. for 4 h and 30 minutes. After cooling, the suspension was filtered, the filtrate was diluted with ethyl acetate (250 mL), washed with water (2×100 mL), dried over $MgSO_4$ and concentrated in vacuo. Purification on silica gel afforded 3-[{[(2-bromo-1,3-thiazol-4-yl)methoxy]imino}(1-methyl-1H-tetrazol-5-yl)methyl]-N,N-dimethylaniline as an oil [1.83 g, yield 86%; HPLC/MS m/z=423 (M+H); $logP_{(HCOOH)}$=3.23].

Preparation of tert-butyl (2-cyclohexylethyl)[6-(hydroxymethyl)pyridin-2-yl]carbamate according to process P11

Step 1

Preparation of tert-butyl (6-bromopyridin-2-yl)carbamate

To a solution of 6-bromopyridin-2-amine (15 g, 86.49 mmol, 1 eq.) in 250 ml of DCM cooled to 0° C. were added DMAP (1.05 g, 8.67 mmol, 0.1 eq.), TEA (9.65 g, 95.36 mmol, 1.1 eq.) and $BOC_2O$ (22.70 g, 104.03 mmol, 1.2 eq.) portionwise. The reaction was stirred at 0° C. for 5 h and quenched with sat. aqueous $NH_4Cl$. The aqueous layer was extracted with DCM, and the organics were combined, dried over MgSO$_4$ and concentrated. The crude residue was purified by chromatography on silica gel to give impure tert-butyl (6-bromopyridin-2-yl)carbamate (mix 80/20 of mono and bis BOC) as a white solid. A chemical purification was then done. This solid was dissolved in 250 ml of THF cooled to 0° C. then iPrMgCl.LiCl (2 M, 51.89 ml, 103.78 mmol, 1.2 eq.) was added dropwise. The solution was stirred 30 min and quenched with aqueous sat. NH$_4$Cl. The aqueous layer was separated and extracted with DCM. The organics were combined, dried over MgSO$_4$ and concentrated to give tert-butyl (6-bromopyridin-2-yl)carbamate (15.96 g, 68%) as a white solid.

HPLC/MS: m/z=275 (M+H); logP$_{(HCOOH)}$=4.11

Step 2

Preparation of tert-butyl (6-formylpyridin-2-yl)carbamate

To a solution of tert-butyl (6-bromopyridin-2-yl)carbamate (15.960 g, 58.43 mmol, 1 eq.) in 300 ml of THF cooled to −78° C. was added MeLi (1.6 M, 36.52 ml, 58.43 mmol, 1 eq.) dropwise and stirring allowed for 30 min. Then BuLi (1.6 M, 40.17 ml, 64.27 mmol, 1.1 eq.) was added dropwise and stirring allowed for 1 h. DMF (9.36 g, 128.55 mmol, 2.2 eq.) was added and the mixture was stirred 30 min at −78° C. and 1 h at r.t. The reaction was quenched with sat. aqueous NH$_4$Cl, and DCM was added. The aqueous layer was extracted with DCM and then organics were combined, dried over MgSO$_4$ and concentrated to give tert-butyl (6-formylpyridin-2-yl)carbamate (13.46 g) as a clear oil that was used directly in next step.

HPLC/MS: m/z=223 (M+H); logP$_{(HCOOH)}$=2.44

Step 3

Preparation of tert-butyl [6-(hydroxymethyl)pyridin-2-yl]carbamate

To a solution of tert-butyl (6-formylpyridin-2-yl)carbamate (13.46 g, 60.57 mmol, 1 eq.) in 200 ml of THF cooled dot 0° C. was added NaBH$_4$ (2.29 g, 60.57 mmol, 1 eq.) portion wise. The reaction was stirred at 0° C. for 1 h and quenched with sat. aqueous NH$_4$Cl. The aqueous layer was extracted with DCM and the organics were combined, dried over MgSO$_4$ and concentrated. The crude residue was purified by chromatography on silica gel to give tert-butyl [6-(hydroxymethyl)pyridin-2-yl]carbamate (9.95 g, 70% yield over 2 steps) as a clear viscous oil.

HPLC/MS: m/z=225 (M+H); logP$_{(HCOOH)}$=1.14

Step 4

Preparation of tert-butyl (2-cyclohexylethyl)[6-(hydroxymethyl)pyridin-2-yl]carbamate To a stirred solution of [6-(hydroxymethyl)pyridin-2-yl] carbamate (200 mg, 1.07 mmol) in DMF, cooled to 0° C. with a brine/ice bath, was added potassium tert-butoxide (126 mg, 1.07 mmol). The mixture was stirred 5 minutes at 0° C. then 1-bromo-2cyclohexylethane (205 mg, 1.07 mmol) was added. After stirring at room temperature for 4 h, the reaction mixture was diluted with ethyl acetate and water. The organic layer was washed with water, dried over MgSO$_4$ and concentrated in vacuo. Purification on silica gel afforded tert-butyl (2-cyclohexylethyl)[6-(hydroxymethyl)pyridin-2-yl]carbamate as a yellow oil [240 mg, yield 64%; HPLC/MS: m/z=335 (M+H); logP$_{(HCOOH)}$=4.49]

Preparation of tert-butyl [6-(bromomethyl)pyridin-2-yl](2-cyclohexylethyl)carbamate According to Process P8

To a stirred solution of thionyl bromide (0.21 mL, 1.64 mmol) in dichloromethane (3 mL), cooled to 0° C. with a brine/ice bath, was added a solution of [6-(hydroxymethyl) pyridin-2-yl]carbamate (500 mg, 1.50 mmol) and pyridine (0.18 mL, 2.24 mmol) in dichloromethane (3 mL) dropwise. After stirring for 2 h at room temperature, further thionyl bromide (38 μL, 0.30 mmol) was added. After stirring for 30 min at room temperature, the mixture was poured into a mixture of ice and aq. sat. NaHCO$_3$ (6 mL) and the layers quickly separated. The aqueous layer was extracted with dichloromethane (3×5 mL), the combined organic layers were washed with water (5 mL), dried over MgSO$_4$ and concentrated in vacuo. Purification on silica gel afforded tert-butyl [6-(bromomethyl)pyridin-2-yl](2-cyclohexylethyl)carbamate as a colourless oil [60 mg, yield 10%; HPLC/MS: m/z=397 (M+H); logP$_{(HCOOH)}$=6.79].

Preparation of tert-butyl (2-cyclohexylethyl)(6-{[({[3-(methylsulfanyl)phenyl](1-methyl-1H-tetrazol-5-yl)methylene}amino)oxy]methyl}pyridin-2-yl)carbamate According to Process P8 Followed by Process P1

To a solution of In a radley tube, tert-butyl (2-cyclohexylethyl)[6-(hydroxymethyl)pyridin-2-yl]carbamate (0.25 g, 0.75 mmol) was dissolved in 5 ml acetonitrile, then triethylamine (0.16 ml, 1.12 mmol) was added. The mixture was cooled to 0° C. then methanesulfonyl chloride (0.069 ml, 0.897 mmol) was added.

After stirring at room temperature for 4 h, N-hydroxy-1-[3-(methylsulfanyl)phenyl]-1-(1-methyl-1H-tetrazol-5-yl) methanimine (0.2 g, 0.68 mmol), cesium carbonate (0.47 g, 1.43 mmol) and potassium iodide (11 mg, 0.068 mmol) were sequentially added to the crude reaction mixture. The reaction mixture was stirred at room temperature for 18 h, then insolubles were removed by filtration and washed with dichloromethane (3×10 mL) and ethyl acetate (3×10 mL). The filtrates were combined and concentrated in vacuo. The residue was dissolved in dichloromethane (20 mL), washed with water (10 mL), the aqueous layer was extracted with dichloromethane (50 mL) and the combined organic layers were washed with water, dried over MgSO$_4$ and concentrated in vacuo. Purification on silica gel afforded tert-butyl (2-cyclohexylethyl)(6-{[({[3-(methylsulfanyl)phenyl](1-methyl-1H-tetrazol-5-yl)methylene}-amino)oxy]methyl}pyridin-2-yl)carbamate as a yellow oil [0.286 g, yield 74%; HPLC/MS: m/z=566 (M+H); logP$_{(HCOOH)}$=6.83].

Preparation of N-(2-cyclohexylethyl)-6-{[({[3-(methylsulfanyl)phenyl](1-methyl-1H-tetrazol-5-yl) methylene}amino)oxy]methyl}pyridin-2-amine According to Process P6

In a radleys tube A (0.286 g, 0.506 mmol) was dissolved in 10 ml dichloromethane. The mixture was cooled to 0° C. then trifluoroacetic acid (0.8 ml, 10.1 mmol) was added.

The reaction mixture was stirred at room temperature for 18 h, then at 45° C. for 2 h.

After a further addition of trifluoroacetic acid (1.55 ml, 20.0 mmol), the mixture was stirred at 45° C. for 2 h, then allowed to cool down to room temperature and diluted with dichloromethane (25 mL) and washed with sat. aq. NaHCO$_3$. The aqueous layer was extracted twice with dichloromethane (20 mL), the combined organic layers were dried over MgSO$_4$ and concentrated in vacuo. Purification on silica gel afforded N-(2-cyclohexylethyl)-6-{[({[3-(methylsulfanyl)phenyl](1-methyl-1H-tetrazol-5-yl)methylene}amino)oxy]methyl}pyridin-2-amine as a colourless oil [0.286 g, yield 74%; HPLC/MS: m/z=566 (M+H); logP$_{(HCOOH)}$=6.83].

Preparation of S-butyl {6-[({[(1-methyl-1H-tetrazol-5-yl)(phenyl)methylene]amino}oxy)methyl]pyridin-2-yl}carbamothioate According to Process P3

To a stirred solution of 6-[({[(1-methyl-1H-tetrazol-5-yl)(phenyl)methylene]amino}oxy)methyl]pyridin-2-amine (150.0 mg, 0.485 mmol) in dichloromethane (5 mL), under argon atmosphere, were added pyridine (0.078 mL, 0.97 mmol) and S-butyl carbonochloridothioate (133 mg, 0.87 mmol) at room temperature. After stirring at room temperature overnight, the reaction mixture was diluted with dichloromethane (50 mL), filtered through "Chem Elut" cartridge, washed with dichloromethane (50 mL) and the filtrate was concentrated in vacuo yielding to S-butyl {6-[({[(1-methyl-1H-tetrazol-5-yl)(phenyl)methylene]amino}oxy)methyl]pyridin-2-yl}carbamothioate as a honey [82 mg, yield 38%; HPLC/MS m/z=426 (M+H); logP$_{(HCOOH)}$=4.25].

Preparation of 2,2-dimethyl-N-(6-methyl-1-oxidopyridin-2-yl)propanamide According to Process P13

Step 1

Preparation of 2,2-dimethyl-N-(6-methylpyridin-2-yl)propanamide

To a stirred and cooled (0° C.) solution of 6-methylpyridin-2-amine (25.00 g, 231.17 mmol) in dichloromethane (250 mL), were added triethylamine (41.81 mL, 300 mmol) and pivaloyl chloride (33.45 g, 277.4 mmol). The reaction mixture was allowed to room temperature and stirred for further 5 hrs. The reaction mixture was quenched with 150 mL of saturated solution of sodium bicarbonate, followed by the addition of 100 mL of brine. The organic phase was separated and dried over magnesium sulphate, filtered and concentrated in vacuo yielding to a yellow solid. The crude product was redissolved in 1 L of dichloromethane, to which were added 100 g of silica. The reaction mixture was stirred for 5 mns at room temperature and filtered yielding to 2,2-dimethyl-N-(6-methylpyridin-2-yl)propanamide as a solid [40.9 g, yield 87%; HPLC/MS: m/z=193 (M+H); logP$_{(HCOOH)}$=1.20].

Step 2

Preparation of 2,2-dimethyl-N-(6-methyl-1-oxidopyridin-2-yl)propanamide

To a stirred solution of 2,2-dimethyl-N-(6-methylpyridin-2-yl)propanamide (3.0 g, 15.6 mmol) in dichloromethane (100 mL), was added meta-chloro-perbenzoïc acid (70%, 11.54 g, 46.81 mmol). The reaction mixture was stirred for 10 hrs at room temperature and allowed to stand for further 48 hrs. The reaction mixture was quenched with an aqueous solution (200 mL) of sodium bicarbonate (10 g) and Na$_2$S$_2$O$_3$ (10 g). The organic phase was separated. The aqueous phase was extracted twice with dichloromethane (100 mL). The combined organics were dried over magnesium sulphate, filtered and concentrated in vacuo yielding to a yellow solid. Purification on silica gel afforded 2,2-dimethyl-N-(6-methyl-1-oxidopyridin-2-yl)propanamide [2.53 g, yield 74%; HPLC/MS: m/z=209 (M+H); logP$_{(HCOOH)}$=1.50].

Preparation of N-hexyl-N-(6-methyl-1-oxidopyridin-2-yl)formamide According to Process P13

Step 1

Preparation of N-(6-methylpyridin-2-yl)formamide

To stirred neat formic acid (3.83 mL, 101.7 mmol) was added acetic anhydride (6.98 mL, 74.0 mmol). The reaction mixture was heated under stirring at 70° C. for 2 hrs and allowed to room temperature. A solution of 6-methylpyridin-2-amine (5.00 g, 46.23 mmol) in tetrahydrofurane (30 mL), was added dropwise in order to prevent temperature from rising above 45° C. The reaction mixture was allowed to room temperature and stirred for further 1 hr. The reaction mixture was concentrated in vacuo and the residue was diluted in 100 mL of ethanol. The reaction mixture was stirred for 2 hrs at room temperature concentrated in vacuo, yielding to N-(6-methylpyridin-2-yl)formamide as a yellow solid [2.00 g, yield 32%; HPLC/MS: m/z=137 (M+H); logP$_{(HCOOH)}$=0.45].

Step 2

Preparation of N-hexyl-N-(6-methylpyridin-2-yl)formamide

To a stirred suspension of sodium hydride (60%, 0.176 g, 4.41 mmol) in DMF (dimethyl-formamide) (5 mL), cooled to 0° C. with a brine/ice bath, under argon atmosphere, was added a solution of N-(6-methylpyridin-2-yl)formamide (500 mg, 3.67 mmol) in DMF (10 mL). The mixture was stirred 5 minutes at 0° C. then 1-iodo-2exaneane (0.86 g, 4.04 mmol) was added. After stirring at room temperature for 48 hrs, the reaction mixture was concentrated and diluted with ethyl acetate (20 mL) and water (50 mL). The aqueous phase was extracted with ethyl acetate (20 mL). The combined organics were dried over MgSO$_4$, filtered and concentrated in vacuo. Purification on silica gel afforded N-hexyl-N-(6-methylpyridin-2-yl)formamide as an oil [0.700 g, yield 77%; HPLC/MS: m/z=221 (M+H); logP$_{(HCOOH)}$=3.46].

Step 3

Preparation of N-hexyl-N-(6-methyl-1-oxidopyridin-2-yl)formamide

To a stirred solution of N-hexyl-N-(6-methylpyridin-2-yl)formamide (0.65 g, 2.95 mmol) in dichloromethane (30 mL), was added meta-chloro-perbenzoïc acid (70%, 11.54 g, 46.81 mmol). The reaction mixture was stirred for 10 hrs at room temperature and allowed to stand for further 48 hrs. The reaction mixture was quenched with an aqueous solution (100 mL) of sodium bicarbonate (10 g) and Na$_2$S$_2$O$_3$ (10 g). The organic phase was separated. The aqueous phase was extracted twice with dichloromethane (20 mL). The combined organics were dried over magnesium sulphate, filtered and concentrated in vacuo yielding to a yellow solid. Purification on silica gel afforded N-hexyl-N-(6-methyl-1-oxidopyridin-2-yl)formamide [0.74 g, yield 43%; HPLC/MS: m/z=237 (M+H); logP$_{(HCOOH)}$=1.82].

The invention claimed is:
1. A hydroximoyl-tetrazole compound of formula (I):

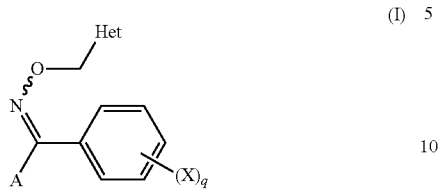

wherein:
A is a member selected from tetrazoyl groups of formula $(A^1)$ and $(A^2)$:

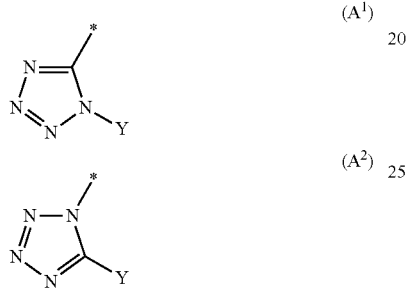

wherein:
Y is an alkyl group;
each X is independently selected from the group consisting of a hydrogen atom, a halogen atom, a nitro group, a hydroxy group, a cyano group, hydroxycarbonyl, $C_1$-$C_8$-alkoxycarbonyl, an amino group, a sulfenyl group, a formyl group, a substituted or non-substituted carbaldehyde O—($C_1$-$C_8$-alkyl)oxime, a formyloxy group, a formylamino group, a carbamoyl group, a N-hydroxycarbamoyl group, a pentafluoro-$\lambda^6$-sulfenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted tri($C_1$-$C_8$-alkyl)silyl-$C_1$-$C_8$-alkyl, substituted or non-substituted $C_3$-$C_8$-cycloalkyl, substituted or non-substituted tri($C_1$-$C_8$-alkyl)silyl-$C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbonyl, substituted or non-substituted N—($C_1$-$C_8$-alkoxy)-$C_1$-$C_8$-alkanimidoyl, substituted or non-substituted N—($C_1$-$C_8$-alkoxy)-$C_1$-$C_8$-halogenoalkanimidoyl having 1 to 5 halogen atoms, substituted or non-substituted $C_1$-$C_8$-halogenoalkylcarbonyl having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl)amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted ($C_1$-$C_8$-alkyl-carbamothioyl)-oxy, substituted or non-substituted (di-$C_1$-$C_8$-alkyl-carbamothioyl)-oxy, substituted or non-substituted $C_1$-$C_8$-alkylsulfinyl, substituted or non-substituted $C_1$-$C_8$-halogenoalkylsulfinyl having 1 to 5 halogen atoms, substituted or non-substituted $C_1$-$C_8$-alkylsulfonyl, substituted or non-substituted $C_1$-$C_8$-halogenoalkylsulfonyl having 1 to 5 halogen atoms, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted aryl-[$C_1$-$C_8$]-alkyl, substituted or non-substituted tri ($C_1$-$C_8$-alkyl)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino) oxy, substituted or non-substituted ($C_1$-$C_6$-alkenylideneamino)oxy, substituted or non-substituted ($C_1$-$C_6$-alkynylideneamino)oxy, substituted or non-substituted (benzylideneamino)oxy, substituted or non-substituted [(arylcarbonyl)amino]-[$C_1$-$C_8$]-alkyl, substituted or non-substituted [{$C_1$-$C_8$-alkyl($C_1$-$C_8$-alkylcarbonyl) amino}]-[$C_1$-$C_8$]-alkyl, substituted or non-substituted [{$C_1$-$C_8$-alkyl(arylcarbonyl)amino}]-[$C_1$-$C_8$]-alkyl, substituted or non-substituted [($C_1$-$C_8$-alkylcarbonyl) amino]-[$C_1$-$C_8$]-alkyl, substituted or non-substituted heterocyclyl, and substituted or non-substituted heterocyclyloxy;

q is 1, 2, 3, 4, or 5, provided that if q is 2, 3, 4, or 5, then each X is independently selected from the group consisting of a hydrogen atom and a halogen atom;

Het is selected from the group consisting of (Het$^1$) and (Het$^3$):

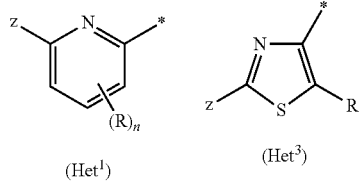

(Het$^1$)        (Het$^3$)

wherein

Z is selected from the group consisting of a halogen atom, a cyano group, a substituted or non-substituted carbaldehyde O—($C_1$-$C_8$-alkyl)oxime, substituted or non-substituted $C_1$-$C_8$-alkoxyamino group, substituted or non-substituted N—$C_1$-$C_8$-alkyl-($C_1$-$C_8$-alkoxy)-amino group, a substituted or non-substituted $C_2$-$C_8$-alkenyl, substituted or non-substituted $C_2$-$C_8$-alkynyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, and substituted or non-substituted $C_1$-$C_8$-halo genoxysulfonylamino having 1 to 5 halogen atoms, each R is independently selected from the group consisting of a hydrogen atom, a halogen atom, a cyano group, an amino group, a substituted or non-substituted carbaldehyde O—($C_1$-$C_8$-alkyl)oxime, a formyloxy group, a formylamino group, a carbamoyl group, an N-hydroxycarbamoyl group, a pentafluoro-$\lambda^6$-sulfenyl group, a formylamino group, substituted or non-substituted $C_1$-$C_8$-alkoxyamino group, substituted or non-substituted N—$C_1$-$C_8$-alkyl-($C_1$-$C_8$-alkoxy)-amino group, substituted or non-substituted ($C_1$-$C_8$-alkylamino)-amino group, substituted or non-substituted N—$C_1$-$C_8$-alkyl-($C_1$-$C_8$-alkylamino)-amino group, a substituted or non-substituted (hydroxyimino)-$C_1$-$C_6$-alkyl group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a substituted or non-substituted $C_2$-$C_8$-alkenyl, substituted or non-substituted $C_2$-$C_8$-alkynyl, substituted or non-substituted $C_1$-$C_8$-alkylamino, substituted or non-substituted di-$C_1$-$C_8$-alkylamino, substituted or non-substituted $C_1$-$C_8$-alkoxy, substituted or non-substituted $C_1$-$C_8$-halogenoalkoxy having 1 to 5 halogen atoms, substituted or non-substituted $C_1$-$C_8$-alkylsulfenyl, substituted or non-substituted $C_1$-$C_8$-halogenoalkylsulfenyl having 1 to 5 halogen atoms, substituted or non-substituted $C_2$-$C_8$-alkenyloxy, substituted or non-substituted $C_2$-$C_8$-halogenoalkenyloxy having 1 to 5 halogen atoms, substituted or non-substituted $C_3$-$C_8$-alkynyloxy, substituted or non-substituted $C_3$-$C_8$-halogenoalkynyloxy having 1 to 5 halogen atoms, substituted or non-substituted $C_1$-$C_8$-alkylcarbamoyl, substituted or non-substituted di-$C_1$-$C_8$-alkylcarbamoyl, substituted or non-substituted N—$C_1$-$C_8$-alkyloxycarbamoyl, substituted or non-substituted $C_1$-$C_8$-alkoxycarbamoyl, substituted or non-substituted N—$C_1$-$C_8$-alkyl-$C_1$-$C_8$-alkoxycarbamoyl, substituted or non-substituted $C_1$-$C_8$-alkoxycarbonyl, substituted or non-substituted $C_1$-$C_8$-halogenoalkoxycarbonyl having 1 to 5 halogen atoms, substituted or non-substituted $C_1$-$C_8$-alkylcarbonyloxy, substituted or non-substituted $C_1$-$C_8$-halogenoalkylcarbonyloxy having 1 to 5 halogen atoms, substituted or non-substituted $C_1$-$C_8$-alkylcarbonylamino, substituted or non-substituted $C_1$-$C_8$-halogenoalkylcarbonylamino having 1 to 5 halogen atoms, substituted or non-substituted $C_1$-$C_8$-alkoxycarbonylamino, substituted or non-substituted $C_1$-$C_8$-halogenoalkoxycarbonylamino having 1 to 5 halogen atoms, substituted or non-substituted $C_1$-$C_8$-alkylcarbamoylamino, substituted or non-substituted $C_1$-$C_8$-halogenoalkylcarbamoylamino having 1 to 5 halogen atoms, substituted or non-substituted di-$C_1$-$C_8$-alkylcarbamoylamino, substituted or non-substituted di-$C_1$-$C_8$-halogenoalkylcarbamoylamino having 1 to 5 halogen atoms, substituted or non-substituted N—$C_1$-$C_8$-alkyl-($C_1$-$C_8$-alkylcarbamoyl) amino, substituted or non-substituted N—$C_1$-$C_8$-alkyl-($C_1$-$C_8$-halogenoalkylcarbamoyl)amino having 1 to 5 halogen atoms, substituted or non-substituted N—$C_1$-$C_8$-alkyl-(di-$C_1$-$C_8$-alkylcarbamoyl)amino, substituted or non-substituted N—$C_1$-$C_8$-alkyl-(di-$C_1$-$C_8$-halogenoalkylcarbamoyl)amino having 1 to 5 halogen atoms, substituted or non-substituted $C_1$-$C_8$-alkylaminocarbonyloxy, substituted or non-substituted di-$C_1$-$C_8$-alkylaminocarbonyloxy, substituted or non-substituted $C_1$-$C_8$-alkylcarbamothioyl, substituted or non-substituted di-$C_1$-$C_8$-alkylcarbamothioyl, substituted or non-substituted N—$C_1$-$C_8$-alkyloxycarbamothioyl, substituted or non-substituted $C_1$-$C_8$-alkoxycarbamothioyl, substituted or non-substituted N—$C_1$-$C_8$-alkyl-$C_1$-$C_8$-alkoxycarbamothioyl, substituted or non-substituted $C_1$-$C_8$-alkylthioylamino, substituted or non-substituted $C_1$-$C_8$-halogenoalkylthioylamino having 1 to 5 halogen atoms, substituted or non-substituted $C_1$-$C_8$-alkylsulfenyl, substituted or non-substituted $C_1$-$C_8$-alkylaminosulfamoyl, substituted or non-substituted di-$C_1$-$C_8$-alkylaminosulfamoyl, substituted or non-substituted ($C_1$-$C_6$-alkoxyimino)-$C_1$-$C_6$-alkyl, substituted or non-substituted ($C_1$-$C_6$-alkenyloxyimino)-$C_1$-$C_6$-alkyl, substituted or non-substituted ($C_1$-$C_6$-alkynyloxyimino)-$C_1$-$C_6$-alkyl, substituted or non-substituted (benzyloxyimino)-$C_1$-$C_6$-alkyl, substituted or non-substituted benzyloxy, substituted or non-substituted benzylsulfenyl, substituted or non-substituted benzylamino, substituted or non-substituted phenoxy, substituted or non-substituted phenylsulfenyl, substituted or non-substituted phenylamino, substituted or non-substituted aryl, substituted or non-substituted heterocyclyl, substituted or non-substituted aryl-($C_1$-$C_8$)-alkyl, substituted or non-substituted tri($C_1$-$C_8$-alkyl)-silyloxy, substituted or non-substituted $C_1$-$C_8$-alkylsulfenylamino, substituted or non-substituted $C_1$-$C_8$-halogenoalkylsulfinylamino having 1 to 5 halogen atoms, substituted or non-substituted $C_1$-$C_8$-alkylsulfonylamino, substituted or non-substituted $C_1$-$C_8$-halogenoalkylsulfonylamino having 1 to 5 halogen atoms, substituted or non-substituted $C_1$-$C_8$-alkoxysulfonylamino, substituted or non-substituted $C_1$-$C_8$-halogenoxysulfonylamino having 1 to 5 halogen atoms, substituted or non-substituted tri($C_1$-$C_8$-alkyl)-silyl, substituted or non-substituted ($C_1$-$C_6$-alkylideneamino)oxy, substituted or non-substituted ($C_1$-$C_6$-alkenylideneamino)oxy, substituted or non-substituted ($C_1$-$C_6$-alkynylideneamino)oxy, and substituted or non-substituted (benzylideneamino)oxy;

n is 0, 1, 2 or 3; and

R' is selected from the group consisting of a hydrogen atom, a halogen atom, a cyano group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_1$-$C_8$-halogenocycloalkyl having 1 to 5 halogen atoms, a $C_2$-$C_8$-alkenyl, substituted or non-substituted $C_2$-$C_8$-alkynyl, substituted or non-substituted $C_1$-$C_8$-alkoxy, substituted or non-substituted $C_1$-$C_8$-halogenoalkoxy having 1 to 5 halogen atoms, substituted or non-substituted aryl, and substituted or non-substituted heterocyclyl;

or a salt, N-oxide, metallic complex or metalloidic complex thereof.

2. The compound of claim 1 wherein Y is selected from the group consisting of a methyl group, an ethyl group, an n-propyl group and an isopropyl group.

3. The compound of claim 1 wherein each X is selected from the group consisting of a hydrogen atom; a chlorine atom; a fluorine atom; an alkyl group having 1 to 4 carbon atoms; an alkoxy group having 1 to 3 carbon atoms; a phenyl group; a 4-methylphenyl group; a 4-chlorophenyl group; and a substituted or non-substituted $C_1$-$C_8$-alkylsulfenyl.

4. The compound of claim 1 wherein q is 1 or 2.

5. The compound of claim 1 wherein each R is independently selected from the group consisting of a hydrogen atom, a halogen atom, a cyano group, a substituted or non-substituted carbaldehyde O—($C_1$-$C_8$-alkyl)oxime, a formylamino group, substituted or non-substituted $C_1$-$C_8$-alkyl, substituted or non-substituted $C_3$-$C_8$-cycloalkyl, substituted or non-substituted $C_1$-$C_8$-halogenoalkyl having 1 to 5 halogen atoms, substituted or non-substituted $C_2$-$C_8$-alkynyl, substituted or non-substituted $C_1$-$C_8$-alkoxy, and a substituted or non-substituted $C_3$-$C_8$-alkynyloxy.

6. The compound of claim 1 wherein n is 0 or 1.

7. The compound of claim 1 wherein R' is selected from the group consisting of a hydrogen atom, a halogen atom, a cyano group, substituted or non-substituted $C_1$-$C_8$-alkyl, and substituted or non-substituted $C_1$-$C_8$-halogenoalkyl having 1 to 5 halogen atoms.

8. A method for controlling the phytopathogenic fungi or damaging insects of plants, crops or seeds comprising applying an agronomically effective and substantially non-phytotoxic quantity of the compound of claim 1 as seed treatment, foliar application, stem application, drench or drip application or chemigation to the seed, the plant or to the fruit of the plant or to soil or to inert substrate, Pumice, Pyroclastic materials or stuff, synthetic organic substrates organic substrates or to a liquid substrate wherein the plant is growing or wherein it is desired to grow.

* * * * *

UNITED STATES PATENT AND TRADEMARK OFFICE
CERTIFICATE OF CORRECTION

PATENT NO. : 8,466,176 B2  Page 1 of 1
APPLICATION NO. : 12/933276
DATED : June 18, 2013
INVENTOR(S) : Beier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 274 days.

Signed and Sealed this
Eighth Day of September, 2015

Michelle K. Lee
*Director of the United States Patent and Trademark Office*